US009163246B2

(12) United States Patent
Barnes

(10) Patent No.: US 9,163,246 B2
(45) Date of Patent: Oct. 20, 2015

(54) T7 EXPRESSION SYSTEM

(76) Inventor: Wayne Barnes, University City, MO (US)

( * ) Notice: Subject to any disclaimer, the term of this patent is extended or adjusted under 35 U.S.C. 154(b) by 1561 days.

(21) Appl. No.: 12/672,606

(22) PCT Filed: Aug. 8, 2008

(86) PCT No.: PCT/US2008/072644
§ 371 (c)(1),
(2), (4) Date: Aug. 9, 2011

(87) PCT Pub. No.: WO2009/021191
PCT Pub. Date: Feb. 12, 2009

(65) Prior Publication Data
US 2011/0300576 A1 Dec. 8, 2011

Related U.S. Application Data

(60) Provisional application No. 60/954,788, filed on Aug. 8, 2007.

(51) Int. Cl.
*C07H 21/04* (2006.01)
*C12N 9/00* (2006.01)
*C12N 15/63* (2006.01)
*C12N 15/70* (2006.01)

(52) U.S. Cl.
CPC ................ *C12N 15/63* (2013.01); *C12N 15/70* (2013.01)

(58) Field of Classification Search
None
See application file for complete search history.

(56) References Cited

U.S. PATENT DOCUMENTS

| | | | |
|---|---|---|---|
| 4,425,437 | A | 1/1984 | Riggs |
| 4,952,496 | A | 8/1990 | Studier et al. |
| 5,498,532 | A | 3/1996 | Katsumata et al. |
| 5,693,489 | A | 12/1997 | Studier et al. |
| 5,824,528 | A | 10/1998 | Studier et al. |
| 5,830,694 | A | 11/1998 | Studier et al. |
| 5,869,320 | A | 2/1999 | Studier et al. |
| 6,180,391 | B1 | 1/2001 | Brown |
| 2005/0202544 | A1 | 9/2005 | Retallack et al. |
| 2007/0117112 | A1 | 5/2007 | Diener et al. |

OTHER PUBLICATIONS

Studier et al., Use of bacteriophage T7 RNA polymerase to direct selective high-level expression of cloned genes, Journal of Molecular Biology vol. 189, Issue 1, May 5, 1986, pp. 113-130.*
Grossman et al., Spontaneous cAMP-dependent derepression of gene expression in stationary phase plays a role in recombinant expression instability, Gene, 1998, 209(1-2):95-103.
Wang et al., Efficient production of recombinant proteins in *Escherichia coli* using an improved I-arabinose-inducible T7 expression system, Process Biochemistry, 2005, 40(9):3137-3142.
Supplementary European Search Report issued on Sep. 22, 2010, in the related application No. 08797506.6.

(Continued)

*Primary Examiner* — Reza Ghafoorian
(74) *Attorney, Agent, or Firm* — Dentons US LLP

(57) ABSTRACT

The present invention provides an improved prokaryotic cell expression system employing a tightly controlled host strain construct that controls uninduced, leaky expression of proteins while still auto-inducing well. Various aspects of the present invention address and overcome the problem of uninduced basal expression by providing a host strain that comprises a T7 polymerase gene, and mutants thereof, inserted between lac Z and lac Y of the lac operon (a "ZRY" construct), downstream of an otherwise wild-type lac operon control region.

23 Claims, 12 Drawing Sheets

(56) References Cited

OTHER PUBLICATIONS

International Search Report and Written Opinion in the related application PCT/US08/72644 issued on Feb. 12, 2009.
Arditti et al., The nature of mutants in the lac promoter region, J Mol. Biol. 1968 38(3):421-6.
Awano et al., Effect of cysteine desulfhydrase gene disruption on L-cysteine overproduction in *Escherichia coli*, Appl Microbiol Biotechnol, 2003 62(2-3):239-43.
Barnes, Variable patterns of expression of luciferase in transgenic tobacco leaves, Proc Natl Acad Sci U S A, 1990, 87(23):9183-7.
Bevis and Glick, Rapidly maturing variants of the Discosoma red fluorescent protein (DsRed), Nat Biotechnol. 2002, 20(1):83-7.
Datsenko and Wanner, One-step inactivation of chromosomal genes in *Escherichia coli* K-12 using PCR products, Proc Natl Acad Sci U S A. 2000, 97(12):6640-5.
Dickson et al., Nucleotide sequence changes produced by mutations in the lac promoter of *Escherichia coli*, J Mol Bio, 1977, 111(1):65-75.
Dickson et al., Protein composition of the tail and contracted sheath of bacteriophage T4, Virology, 1974, 59(1):123-38.
Flashner and Gralla, Dual mechanism of repression at a distance in the lac operon, Proc Natl Acad Sci U S A, 1988, 85(23):8968-72. 1988.
Ghadessy et al. Directed evolution of polymerase function by compartmentalized self-replication, Proc Natl Acad Sci USA, 2001, 98(8):4552-4557.
Ippen et al. New controlling element in the Lac operon of *E. coli*, Nature, 1968, 217(5131):825-7.
Landick and Yanofsky, Stability of an RNA secondary structure affects in vitro transcription pausing in the trp operon leader region, J Biol Chem, 1984, 259(18):11550-5.
Link et al., Beyond toothpicks: new methods for isolating mutant bacteria, Nature Reviews, 2007, 5(9):680-688.
Miroux and Walker, Over-production of proteins in *Escherichia coli*: mutant hosts that allow synthesis of some membrane proteins and globular proteins at high levels, J Mol Biol, 1996, 260(3):289-98.
Oehler et al., Characterization of the v-myb DNA binding domain, Nucleic Acids Res., 1990, 18(7):1703-10.
Posfai et al., Emergent properties of reduced-genome *Escherichia coli*, Science, 2006, 312(5776):1044-6.
Sagner et al., Rapid filter assay for the detection of DNA polymerase activity: direct identification of the gene for the DNA polymerase from *Thermus aquaticus*, Gene, 1991, 97(1):119-123 (Abstract only).
Schultz et al., Crystal structure of a CAP-DNA complex: the DNA is bent by 90 degrees, Science, 1991, 253(5023):1001-7.
Silverstone et al. Catabolite-insensitive revertants of lac promoter mutants, Proc Natl Acad Sci U S A, 1970, 66(3):773-9.
Studier et al., Use of bacteriophage T7 lysozyme to improve an inducible T7 expression system, J Mol Biol, 1991, 219(1):37-44.
Studier, Protein production by auto-induction in high density shaking cultures, Protein Expr Purif, 2005, 41(1):207-234.
Tabor and Richardson, A bacteriophage T7 RNA polymerase/promoter system for controlled exclusive expression of specific genes, PNAS USA, 1985, 82:1074-1078.
Tomalski et al., The location, sequence, transcription, and regulation of a baculovirus DNA polymerase gene, Virology, 1988, 167(2):591-600.
Yakhnin et al., Green fluorescent protein purification by organic extraction, Protein Expr Purif, 1998, 14(3):382-6.
Yanofsky, Attenuation in the control of expression of bacterial operons, Nature, 1981, 289(5800):751-8.
Yanofsky, Transcription attenuation: once viewed as a novel regulatory strategy, J Bacteriol, 2000, 182(1):1-8.
Barnes and Tuley, DNA sequence changes of mutations in the histidine operon control region that decrease attenuation, J Mol Biol, 1983, 165:443-459.
Dickson et al., Genetic Regulation: The Lac Control Region, 1975, Science, 187:27-35.
Barnes, DNA sequence from the histidine operon control region: Seven histidine codons in a row, PNAS, 1978, 75:4281-4285.
Kermekchiev et al., Mutants of Taq DNA polymerase resistant to PCR inhibitors allow DNA amplification from whole blood and crude soil samples, Nucleic Acids Res., 2008, 14 pages (pre-publication print).
Barnes, Sequencing DNA with Dideoxyribonucleotides as Chain Terminators: Hints and Strategies for Big Projects, Meth. Enzym., 1987, 152:538-556.
Kermekchiev et al., Cold-sensitive mutants of Taq DNA polymerase provide a hot start for PCR, Nucleic Acids Res., 2003, 31:6139-6147.
Barnes et al., Kilo-Sequencing: Creation of an ordered nest of asymmetric deletions across a large target sequence carried on phage M13, Methods Enzym., 1983, 101:98-122.
Korolev et al., Crystal structure of the large fragment of *Thermus aquaticus* DNA polymerase I at 2.5 (angstrom) resolution: Structural basis for thermostability, PNAS USA, 1995, 92:9264-9268.
Barnes, PCR amplification of up to 35-kb DNA with high fidelity and high yield from (lambda) bacteriophage templates, PNAS USA, 1994, 91:2216-2220.
Barnes, Ribocloning: DNA cloning and gene construction using PCR primers terminated with a ribonucleotide, PCR Primer, second edition, 2003, Ed. Dieffenbach. pp. 441-449 (prepublication print).
Zhang et al., Direct DNA amplification from crude clinical samples using a PCR enhancer cocktail and novel mutants of Taq, J Mol. Diagnostics, 2010, 12:152-161.
Barnes, The fidelity of Taq polymerase catalyzing PCR is improved by an N-terminal deletion, Gene 1992, 112:29-35.
Tunitskaya et al., Structural-functional analysis of bacteriophage T7 RNA polymerase, Biochemistry, 2002, pp. 1124-1135, vol. 67, No. 10.

* cited by examiner

```
3240      3250      3260      3270      3280
  TGGTGTCAAAAATAACTGGAAGAGGCACTAAATGAACACGATT
  TrpCysGlnLys***             MetAsnThrIle
         Lac Z                T7 RNA Polymerase (2.5 kb)
               ...............................
  ---------------

5910      5920      5930      5940      5950
TTCGCGTTCGCGTAAGGAAATCCATTATGTACTATTTAAAAAAC
PheAlaPheAla***           MetTyrTyrLeuLysAsn
T7 RNA polymerase         Lac Y
...............
```

..... indicates T7 phage DNA homology

----- indicates E. coli genome homology

T7 EXPRESSION SYSTEM

CROSS-REFERENCE TO RELATED APPLICATIONS

This application is a national stage application under 35 U.S.C. §371 claiming priority to PCT/US2008/72644, filed Aug. 8, 2008, which in turn claims priority to U.S. Provisional Application Ser. No. 60/954,788, filed Aug. 8, 2007, each of which is incorporated herein by reference in its entirety.

INCORPORATION-BY-REFERENCE OF MATERIAL SUBMITTED IN COMPUTER READABLE FORM

The Sequence Listing, which is a part of the present disclosure, includes a computer readable form comprising nucleotide and/or amino acid sequences of the present invention. The subject matter of the Sequence Listing is incorporated herein by reference in its entirety.

FIELD

The present invention generally relates to a system for expressing genes to proteins in *E. coli.*

BACKGROUND

T7 promoters have been used to achieve control of the expression of exogenous genes in *E. coli*, since their expression can be turned on by controlling the presence and expression of the T7 gene 1 (SEQ ID NO: 1) for T7 RNA polymerase (SEQ ID NO: 2) (Studier & Moffat, 1986; Studier et al., 1990; Tabor & Richardson, 1985). Phage T7 RNA polymerase does not recognize *E. coli* promoters, and vice versa (i.e., *E. coli* RNA polymerase does not recognize T7 promoters, except for the special "*E. coli*" one that transcribes gene 1).

The *E. coli* lac operon has been characterized (see e.g., Dickson et al, 1974; Schultz, Shields, & Steitz, 1991; Oehler, et al. 1990; Flashner & Gralla, 1988). The polycistronic lac operon mRNA molecule encodes three genes: Lac Z, Lac Y and Lac A. The product of the Lac Z coding region functions as a β-galactosidase; this function is required for the metabolism of lactose into glucose and galactose. The product of the Lac Y coding region functions as a lactose permease, which is a membrane-bound transport protein that allows lactose to enter the cell. Lac A is a β-galactosidase transacetylase, and does not appear to be strictly required for lactose metabolism.

The lactose operon genetic control region contains binding sites for 3 control proteins: CAP, RNA polymerase, and lac repressor (Dickson et al, 1974). Mutation L8 (a.k.a. L37) is a G to A transition (Dickson et al., 1977) in the CAP site, which eliminates the possibility of binding or activation by CAP protein when glucose is absent. Since binding by CAP protein activates the lac promoter 16-fold by introducing a 90° bend (Schultz, Shields, & Steitz, 1991), the L8 mutation results in a decreased level of transcription (e.g., to 6%). The phenotype is slightly Lac+ but melibiose negative at 42° C. (Ippen et al. 1968). During genetic analysis of the lac operon, second-site Lac+ (i.e., raffinose+) revertants of this CAP site mutant were selected after UV mutagenesis (Arditti et al, 1968; Silverstone et al. 1970), with the UV5 mutant consisting of a further change of two adjacent base pairs in the RNA polymerase binding site. The resulting promoter region, with a total of 3 base-pair changes, produced a promoter that is stronger than lac wild-type and oblivious to glucose repression, yet is still under control of lac repressor. The resultant L8-UV5 has been widely useful as a model promoter for basic transcription studies. As for the repressor, it is a tetrameric dimer-of-dimers and must bind at least two operators to achieve its full level of repression: Part of the binding of, and control by, the lac repressor depends on operator O2, some 400 bp into the lacZ gene (Oehler, et al. 1990; Flashner & Gralla, 1988). Operator O3, in the I gene, overlaps the CAP site so nearly that it has been proposed to 'repress' by interfering with CAP binding (Oehler et al, 1990); in parallel, it may serve to auto-repress the I gene.

Studier (2005) has recently formulated a mixture of sugars consisting of 0.5% glycerol, 0.05% glucose, and 0.2% lactose (ZYM-5052; herein "5052") to replace the manual addition of inducer IPTG, achieving effective and convenient "auto-induction" of cultures for the purpose of exogenous protein production in *E. coli*. The host strain for this system is BL21 (DE3), a lysogen of phage lambda DE3 carrying the T7 gene 1 (SEQ ID NO: 1) under the control of the lac L8-UV5 promoter.

Auto-induction polypeptide expression systems rely on the principle that an inducer can induce production of target protein but is prevented from doing so by compounds that can be depleted during growth. This allows use of media in which target protein is produced automatically, without the need to monitor growth and add inducer at the proper time. Ideal auto-induction systems allow the host strain to grow in auto-inducing medium without expressing target protein until rather high density, when depletion of inhibitory factors would allow the inducer present in the medium to induce expression, thus producing high concentrations of target protein. For example, glucose in the medium can prevent the uptake and utilization of lactose inducer but when glucose is depleted, the lactose inducer can effectively induce expression of the target protein. Auto-induction is generally preferred over IPTG induction for increased simplicity (e.g., no need to follow culture growth or add inducer at the proper time), increased culture density, and increased concentration of target protein per volume of culture.

But, like all known inducible promoter systems, auto-induction polypeptide expression systems have a residual level of activity or "leakiness", which leads to the inappropriate transcription and expression of the gene being cloned under the control of the promoter.

The auto-inducing expression system of Studier (2005) is widely used in the industry. Additionally, there exist several modifications to the system. For example, some researchers have inserted the T7 RNA polymerase (gene I) into lacZ (e.g., New England Biolabs), which is reported to provide better control but at the expense of auto-induction (because auto-induction requires lacZ (beta-galactosidase) to make the inducer allolactose). As another example, some researchers have aligned T7 RNA polymerase gene I with the arabinose promoter (e.g., Invitrogen), but one must include arabinose in addition to 5052 sugar mixture for auto-induction. The inventor has observed that the auto-induced level is not as high with this strain, and it has a leaky background in Studier's recommended non-inducing medium. As another example, strains have been selected as resistant to several families of toxic proteins (e.g., Miroux & Walker, 1996; Lucigen). As another example, the gene for T7 lysozyme, a natural inhibitor of T7 RNA polymerase, has been included on another (chloramphenicol-resistant) plasmid (Studier 1991). Further examples include plasmid copy-number control for the T7 expression vector (e.g., pETcoco, Novagen), and the addition of another lac operator (although it now has O1 and O3) to the pET vector series.

Thus there exists a need for improvements to the auto-induction expression system in which the T7 gene 1 is under control of the lac L8-UV5 promoter, especially with regard to reducing the uninduced leaky level of expression.

SUMMARY

The present invention provides an improved T7 expression system using, in part, the *E. coli* wild-type lac promoter-operator region, resulting in a tightly controlled host strain construct that can control uninduced, leaky expression of proteins while still auto-inducing well. The present teachings address and overcome the problem of promoter leakiness by providing a host strain that comprises a T7 polymerase gene inserted between lac Z and lac Y of the lac operon (a “ZRY strain”), downstream of an otherwise wild-type lac operon control region. Embodiments of the present invention to the host genome can be transparently compatible with, and additive to, various existing genomic and/or plasmid improvements.

One aspect of the invention provides an isolated ZRY construct. A first polynucleotide sequence (R) comprises one of: (a) an isolated polynucleotide comprising a nucleotide sequence encoding the polypeptide of SEQ ID NO: 2; (b) an isolated polynucleotide comprising SEQ ID NO: 1 encoding a T7 RNA polymerase; (c) an isolated polynucleotide comprising a nucleotide sequence which has at least 95% identity to that of SEQ ID NO: 1 over the entire length thereof and which encodes a polypeptide having RNA polymerase activity; (d) an isolated polynucleotide that hybridizes under stringent conditions to SEQ ID NO: 1 over the entire length of SEQ ID NO: 1; said stringent conditions comprising incubation at 65° C. in a solution comprising 6×SSC (0.9 M sodium chloride and 0.09 M sodium citrate); and which encodes a polypeptide having RNA polymerase activity; or (e) an isolated polynucleotide complementary to the polynucleotide sequence of (a), (b), (c), or (d). Z is a lac Z polynucleotide sequence encoding β-galactosidase. Y is a lac Y polynucleotide sequence encoding a β-galactoside permease. The isolated construct also comprises a wild-type lac control region (C) comprising a CAP binding site, a promoter, an operator, and a ribosome binding site. The polynucleotide encoding T7 RNA polymerase or mutant T7 RNA polymerase is located between lac Z and lac Y. ZRY is downstream of the wild-type lac control region. The promoter of the wild-type lac control region is a lac-inducible and catabolite-repressible promoter recognized by a host cell polymerase. And the polynucleotide encoding the T7 RNA polymerase or mutant T7 RNA polymerase is under the control of the lac-inducible and catabolite-repressible promoter.

Another aspect of the invention provides an expression system for producing a target polypeptide in a host cell. The expression system comprises an isolated DNA construct, as described above. The expression system also comprises a target promoter polynucleotide sequence recognized by the encoded T7 RNA polymerase of ZRY. The expression system also comprises a polynucleotide sequence encoding a target polypeptide. The polynucleotide sequence encoding a target target polypeptide is under control of the target promoter polynucleotide sequence.

Another aspect of the invention provides a transformed prokaryotic cell. The transformed prokaryotic cell comprises an isolated ZRY construct, as described above. Or the transformed prokaryotic cell comprises a ZRY expression system, as described above. Or the transformed prokaryotic cell comprises a polynucleotide sequence (R) encoding a T7 RNA polymerase or mutant T7 RNA polymerase selected from: (a) a isolated polynucleotide comprising a nucleotide sequence encoding the polypeptide of SEQ ID NO: 2; (b) an isolated polynucleotide comprising SEQ ID NO: 1 encoding a T7 RNA polymerase; (c) an isolated polynucleotide comprising a nucleotide sequence which has at least 95% identity to that of SEQ ID NO: 1 over the entire length thereof and which encodes a polypeptide having RNA polymerase activity; (d) an isolated polynucleotide that hybridizes under stringent conditions to SEQ ID NO: 1 over the entire length of SEQ ID NO: 1; said stringent conditions comprising incubation at 65° C. in a solution comprising 6×SSC (0.9 M sodium chloride and 0.09 M sodium citrate); and which encodes a polypeptide having RNA polymerase activity; or (e) an isolated polynucleotide complementary to the polynucleotide sequence of (a), (b), (c), or (d). The polynucleotide encoding T7 RNA polymerase or mutant T7 RNA polymerase is located between lac Z and lac Y. ZRY is downstream of the wild-type lac control region. And the polynucleotide encoding the T7 RNA polymerase or mutant T7 RNA polymerase is under the control of the lac-inducible and catabolite-repressible promoter. In various embodiments, one of both of lac Z and lac Y can be endogenous to the host cell.

Another aspect of the invention provides a method for producing a target polypeptide in a host cell. The method comprises providing an isolated ZRY construct, as described above; or providing a polynucleotide sequence (R) encoding a T7 RNA polymerase or a mutant T7 RNA polymerase, as described above. The method also comprises providing a polynucleotide sequence encoding a target polypeptide under control of a target promoter polynucleotide sequence, which is recognized by the encoded T7 RNA polymerase or mutant T7 RNA polymerase. The method further comprises introducing the ZRY construct into the host cell, or introducing the polynucleotide sequence encoding the T7 RNA polymerase or mutant T7 RNA polymerase between lac Z and lac Y of the host cell, where ZRY is downstream of a wild-type lac control region; and the polynucleotide sequence (R) is under control of a lac-inducible and catabolite-repressible promoter of the wild-type lac control region. The method further comprises introducing into the host cell the polynucleotide sequence encoding the target polypeptide under control of the target promoter. The method further comprises incubating the host cell under conditions appropriate for expression of a T7 RNA polymerase encoded by the first polynucleotide sequence (R) and expression of the target polypeptide from the target polynucleotide sequence.

In various embodiments, the host cell further comprises a polynucleotide encoding a colorometric positive indicator of T7 RNA polymerase expression. In some embodiments, the colorometric positive indicator is DsRed.T3.

In various embodiments, the host cell is an *E. coli* cell. In some embodiments, the host cell is an *E. coli* strain selected from the group consisting BL21, C2566, DH1, DH4I, DH5, DH5I, DH5IF', DH5IMCR, DH10B, DH10B/p3, DH11S, C600, HB101, JM101, JM105, JM109, JM110, K38, MG1655, RR1, Y1088, Y1089, CSH18, ER1451, and ER1647. In some embodiments, the host cell is *E. coli* strain BL21.

In various embodiments, the transformed cell is *E. coli* strain WB456.7, *E. coli* strain WB466.15, *E. coli* strain WB478e, or *E. coli* strain WB477f.

In various embodiments, the first polynucleotide sequence (R) comprises an isolated nucleotide sequence having at least 95% identity to SEQ ID NO: 1 over the entire length thereof and encoding a polypeptide having T7 RNA polymerase activity.

In various embodiments, the first polynucleotide sequence (R) comprises a nucleotide sequence that: has at least 95% identity to SEQ ID NO: 1 over the entire length thereof; has at least one mutation selected from the group consisting of: a mutation at base 251 of CGC to CAC; a mutation at base 1240 of ATC to GTC; a mutation at base 1958 of GAT to GGT; a mutation at base 2092 from TGG to GGG; and a mutation at base 2203 from GTG to ATG; and encodes a polypeptide having RNA polymerase activity. In some embodiments, the first polynucleotide sequence (R) comprises a nucleotide sequence selected from the group consisting of SEQ ID NO: 3; SEQ ID NO: 5; SEQ ID NO: 7; SEQ ID NO: 9; and SEQ ID NO: 11. In some embodiments, the first polynucleotide sequence (R) comprises a nucleotide sequence that encodes an amino acid sequence selected from the group consisting of SEQ ID NO: 4; SEQ ID NO: 6; SEQ ID NO: 8; SEQ ID NO: 10; and SEQ ID NO: 12.

In various embodiments, the first polynucleotide sequence (R) comprises a nucleotide sequence that: has at least 95% identity to SEQ ID NO: 1 over the entire length thereof; has at least two mutations selected from the group consisting of: a mutation at base 251 of CGC to CAC; a mutation at base 1240 of ATC to GTC; a mutation at base 1958 of GAT to GGT; a mutation at base 2092 from TGG to GGG; and a mutation at base 2203 from GTG to ATG; and encodes a polypeptide having RNA polymerase activity. In some embodiments, the first polynucleotide sequence (R) comprises a nucleotide sequence selected from the group consisting of SEQ ID NO: 13; SEQ ID NO: 15; SEQ ID NO: 17; SEQ ID NO: 19; and SEQ ID NO: 21; SEQ ID NO: 23; SEQ ID NO: 25; SEQ ID NO: 27; SEQ ID NO: 29; and SEQ ID NO: 31. In some embodiments, the first polynucleotide sequence (R) comprises a nucleotide sequence of SEQ ID NO: 31. In some embodiments, the first polynucleotide sequence (R) comprises a nucleotide sequence that encodes an amino acid sequence selected from the group consisting of SEQ ID NO: 14; SEQ ID NO: 16; SEQ ID NO: 18; SEQ ID NO: 20; SEQ ID NO: 22; SEQ ID NO: 24; SEQ ID NO: 26; SEQ ID NO: 28; SEQ ID NO: 30; and SEQ ID NO: 32. In some embodiments, the first polynucleotide sequence (R) comprises a nucleotide sequence that encodes an amino acid sequence of SEQ ID NO: 32.

In various embodiments, the first polynucleotide sequence (R) comprises a nucleotide sequence that: has at least 95% identity to SEQ ID NO: 1 over the entire length thereof; has at least three mutations selected from the group consisting of: a mutation at base 251 of CGC to CAC; a mutation at base 1240 of ATC to GTC; a mutation at base 1958 of GAT to GGT; a mutation at base 2092 from TGG to GGG; and a mutation at base 2203 from GTG to ATG; and encodes a polypeptide having RNA polymerase activity. In some embodiments, the first polynucleotide sequence (R) comprises a nucleotide sequence selected from the group consisting of SEQ ID NO: 33; SEQ ID NO: 35; SEQ ID NO: 37; SEQ ID NO: 39; and SEQ ID NO: 41; SEQ ID NO: 43; SEQ ID NO: 45; SEQ ID NO: 47; SEQ ID NO: 49; and SEQ ID NO: 51. In some embodiments, the first polynucleotide sequence (R) comprises a nucleotide sequence of SEQ ID NO: 49. In some embodiments, the first polynucleotide sequence (R) comprises a nucleotide sequence that encodes an amino acid sequence selected from the group consisting of SEQ ID NO: 34; SEQ ID NO: 36; SEQ ID NO: 38; SEQ ID NO: 40; and SEQ ID NO: 42; SEQ ID NO: 44; SEQ ID NO: 46; SEQ ID NO: 48; SEQ ID NO: 50; and SEQ ID NO: 52. In some embodiments, the first polynucleotide sequence (R) comprises a nucleotide sequence that encodes an amino acid sequence of SEQ ID NO: 50.

In various embodiments, the first polynucleotide sequence (R) comprises a nucleotide sequence that: has at least 95% identity to SEQ ID NO: 1 over the entire length thereof; has at least four mutations selected from the group consisting of: a mutation at base 251 of CGC to CAC; a mutation at base 1240 of ATC to GTC; a mutation at base 1958 of GAT to GGT; a mutation at base 2092 from TGG to GGG; and a mutation at base 2203 from GTG to ATG; and encodes a polypeptide having RNA polymerase activity. In some embodiments, the first polynucleotide sequence (R) comprises a nucleotide sequence selected from the group consisting of SEQ ID NO: 53; SEQ ID NO: 55; SEQ ID NO: 57; and SEQ ID NO: 59. In some embodiments, the first polynucleotide sequence (R) comprises a nucleotide sequence of SEQ ID NO: 53. In some embodiments, the first polynucleotide sequence (R) comprises a nucleotide sequence that encodes an amino acid sequence selected from the group consisting of SEQ ID NO: 54; SEQ ID NO: 56; SEQ ID NO: 58; and SEQ ID NO: 60. In some embodiments, the first polynucleotide sequence (R) comprises a nucleotide sequence that encodes an amino acid sequence of SEQ ID NO: 54.

In various embodiments, the first polynucleotide sequence (R) comprises a nucleotide sequence that: has at least 95% identity to SEQ ID NO: 1 over the entire length thereof; has at least five mutations of: a mutation at base 251 of CGC to CAC; a mutation at base 1240 of ATC to GTC; a mutation at base 1958 of GAT to GGT; a mutation at base 2092 from TGG to GGG; and a mutation at base 2203 from GTG to ATG; and encodes a polypeptide having RNA polymerase activity. In some embodiments, the first polynucleotide sequence (R) comprises a nucleotide sequence of SEQ ID NO: 61. In some embodiments, the first polynucleotide sequence (R) comprises a nucleotide sequence that encodes an amino acid sequence of SEQ ID NO: 62.

In various embodiments, the lac Z polynucleotide (Z) comprises: a nucleotide sequence selected from group consisting of SEQ ID NO: 63 and SEQ ID NO: 65, or a variant having at least 95% identity thereof encoding a polypeptide having β-galactosidase activity; or a nucleotide sequence encoding a polypeptide having an amino acid sequence selected from the group consisting of SEQ ID NO: 64 and SEQ ID NO: 66 and β-galactosidase activity, or a variant having at least 95% identity thereof and β-galactosidase activity. In some embodiments, the lac Z polynucleotide (Z) comprises a lac Z polynucleotide from *E. coli* strain BL21.

In various embodiments, the lac Y polynucleotide (Y) comprises: a nucleotide sequence selected from group consisting of SEQ ID NO: 67 and SEQ ID NO: 69, or a variant having at least 95% identity thereof encoding a polypeptide having β-galactoside permease activity; or a nucleotide sequence encoding a polypeptide having an amino acid sequence selected from the group consisting of SEQ ID NO: 68 and SEQ ID NO: 70 and β-galactoside permease activity, or a variant having at least 95% identity thereof and having β-galactoside permease activity. In some embodiments, the lac Y polynucleotide (Y) comprises a lac Y polynucleotide from *E. coli* strain BL21.

In various embodiments, the wild-type lac control region (C) comprises a nucleotide sequence selected from the group consisting of SEQ ID NO: 71 and SEQ ID NO: 72, or a variant having at least 95% identity thereof having a functional CAP binding site, promoter, operator, and ribosome binding site.

In various embodiments, the first polynucleotide sequence (R) encodes a temperature-sensitive T7 RNA polymerase. In some embodiments, T7 promoter activation does not occur at about 37° C. but does occur at about 30° C.

Another aspect of the invention provides a mutant T7 RNA polymerase as an isolated polypeptide.

In various embodiments, the isolated polypeptide comprises a variant of a polypeptide of SEQ ID NO: 2 wherein, the variant polypeptide is at least 95% identical to SEQ ID NO: 2 over the entire length thereof; the variant polypeptide has at least two mutations at an amino acid residue position corresponding to SEQ ID NO: 2 selected from the group consisting of: amino acid residue 84, Arg to His; amino acid residue 414, Ile to Val; amino acid residue 653, Asp to Gly; amino acid residue 698, Trp to Gly; and amino acid residue 735, Val to Met; the variant polypeptide has RNA polymerase activity; the variant polypeptide has reduced rates of uninduced expression in a T7 expression system compared to a T7 RNA polymerase of SEQ ID NO: 2; and the variant polypeptide has about the same or greater rates of induced expression in a T7 expression system compared to a T7 RNA polymerase of SEQ ID NO: 2. In some embodiments, the isolated polypeptide comprises an amino acid sequence selected from the group consisting of SEQ ID NO: 14; SEQ ID NO: 16; SEQ ID NO: 18; SEQ ID NO: 20; SEQ ID NO: 22; SEQ ID NO: 24; SEQ ID NO: 26; SEQ ID NO: 28; SEQ ID NO: 30; and SEQ ID NO: 32. In some embodiments, the isolated polypeptide comprises an amino acid sequence of SEQ ID NO: 32.

In some embodiments, the isolated polypeptide has at least three mutations at an amino acid residue position corresponding to SEQ ID NO: 2 selected from the group consisting of: amino acid residue 84, Arg to His; amino acid residue 414, Ile to Val; amino acid residue 653, Asp to Gly; amino acid residue 698, Trp to Gly; and amino acid residue 735, Val to Met. In some embodiments, the isolated polypeptide comprises an amino acid sequence selected from the group consisting of: SEQ ID NO: 34; SEQ ID NO: 36; SEQ ID NO: 38; SEQ ID NO: 40; and SEQ ID NO: 42; SEQ ID NO: 44; SEQ ID NO: 46; SEQ ID NO: 48; SEQ ID NO: 50; and SEQ ID NO: 52. In some embodiments, the isolated polypeptide comprises an amino acid sequence of SEQ ID NO: 50.

In some embodiments, the isolated polypeptide has at least four mutations at an amino acid residue position corresponding to SEQ ID NO: 2 selected from the group consisting of: amino acid residue 84, Arg to His; amino acid residue 414, Ile to Val; amino acid residue 653, Asp to Gly; amino acid residue 698, Trp to Gly; and amino acid residue 735, Val to Met. In some embodiments, the isolated polypeptide comprises an amino acid sequence selected from the group consisting of: SEQ ID NO: 54; SEQ ID NO: 56; SEQ ID NO: 58; and SEQ ID NO: 60. In some embodiments, the isolated polypeptide comprises an amino acid sequence of SEQ ID NO: 54.

In some embodiments, the isolated polypeptide has at least five mutations at an amino acid residue positions corresponding to SEQ ID NO: 2 of: amino acid residue 84, Arg to His; amino acid residue 414, Ile to Val; amino acid residue 653, Asp to Gly; amino acid residue 698, Trp to Gly; and amino acid residue 735, Val to Met. In some embodiments, the isolated polypeptide comprises an amino acid sequence selected from the group consisting of: SEQ ID NO: 62.

Another aspect of the invention provides an isolated nucleic acid encoding an isolated polypeptide described above.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 4A shows Medium PG (Studier, 2005; phosphate salts, glucose as carbon source). The +/−Ser experiment visible on the label showed no difference. Tube 3 in FIG. 4A is a negative control with no T7 RNA polymerase gene. Tubes 2, 6, and 8 in FIG. 4A represent unsatisfactory constitutive constructs. Tube 7 in FIG. 4A is strain pWB456.7. The tube on the right of FIG. 4A is BL21(DE3). All strains shown in FIG. 4A harbor pWB536. FIG. 4B shows Medium MGD, Studier's recommended uninduced medium, after overnight culture. Tubes in FIG. 4B are as described in FIG. 4A. Again, WB456.7 has lower leakiness than BL21(DE3). For details regarding methodology, see Example 3.

FIG. 4 demonstrates that strain WB456.7 has a lower background expression on rich plates than BL21 (DE3) carrying the same expression plasmid pWB536. For details regarding methodology, see Example 3.

FIG. 10 depicts the designed intergenic regions of the BL21-ZRY genome. Numbering is that of the transforming PCR-product DNA. All lac operon sequence not shown was intended to be wild-type, but strain WB466.15 may have silent and/or beneficial mutations. Dotted lines indicate T7 phage homology while dashed lines indicate *E. coli* genome homology. The T7 phage DNA also has unplanned mutations, which may be silent or beneficial.

FIG. 11 also contains a bar graph presenting quantified results (intensity of red indicator protein as red/green ratio) of the photograph pictured above it.

DETAILED DESCRIPTION

Figure 1:
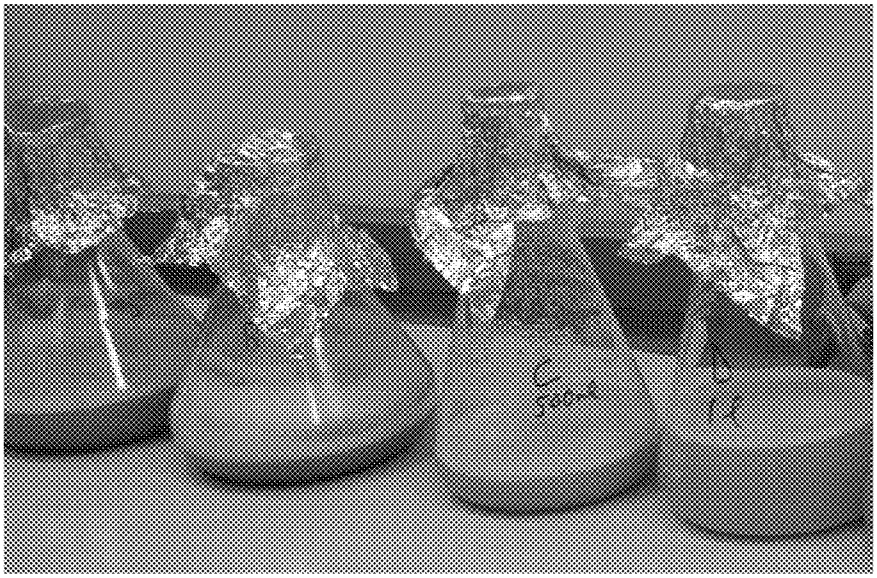
FIG. 1 is a photograph showing colored protein indicator resulting from plasmid pWB536, which expresses the fast-maturing T3 form of DsRed (Bevis & Glick, 2002) on the vector plasmid pET11. Four flasks, of different shapes and containing different volumes of media, were incubated under equivalent conditions. For details regarding methodology, see Example 1.

The present inventors have developed, in various aspects of the present teachings, a variant of the T7 expression system that is extremely tight (i.e., low levels of "leaky" basal non-induced expression), and yet, still auto-inducible.

The present invention is based, at least in part, on mechanistic information about the catabolite-insensitivity of the lac L8-UV5 promoter used for the T7 RNA polymerase gene. By providing a wild-type lac operon control region, and by inserting a polynucleotide encoding a T7 polymerase between lac Z and lac Y of the lac operon (i.e., a "ZRY" construct), full sensitivity to catabolite repression can be preserved and leakiness of the expression system (i.e., a "ZRY strain") can be reduced. A prokaryotic expression system utilizing a ZRY strain can be fully sensitive to catabolite repression and provides reduced leakiness and superior performance as compared to, for example, an expression system employing a T7 RNA polymerase under the control of the mutant lac L8-UV5 promoter. This high level of repression can be utilized, for example, to allow overproduction of proteins, including toxic proteins that were previously not tolerated, in *E. coli.*

Full expression of a target gene from an expression clone with a T7lac promoter requires both induction of T7 RNA polymerase and release of the lac repressor from its binding site in the T7lac promoter. Both events can be triggered by release of the lac repressor by, for example, addition of IPTG or by the presence of lactose in the medium. But, like other prior art inducible promoter systems, auto-induction T7lac polypeptide expression systems have a residual level of activity or "leakiness", which can lead to the inappropriate transcription and expression of the gene being cloned under the control of the promoter. A significant fraction of gene products (proteins), especially eukaryotic gene products, which may be worthy subjects of molecular and medical research, are in fact toxic to a bacterial cell which has not evolved to tolerate these exogenous proteins. Inappropriate early expression of gene products (proteins) which are toxic to the *E. coli* cell can prevent the study of these proteins using the T7 expression system.

It has now been discovered that at least a part of the leakiness of the widely-used BL21(DE3) expression system is due to the catabolite-insensitive lac L8-UV5 promoter used for the T7 RNA polymerase gene (SEQ ID NO.: 72).

Provided herein is a variant of the T7 expression system, in which a polynucleotide encoding a T7 RNA polymerase is inserted between lac Z and lac Y of the lac operon (i.e., a "ZRY" construct). Thus is provided full sensitivity to catabolite repression and reduced leakiness of a system for expression of a target polypeptide. Also described herein is a method for producing a selected gene product in a host cell employing a ZRY construct. Such a system can be even further improved through incorporation of a polynucleotide encoding a mutant T7 RNA polymerase. Mutant T7 RNA polymerase polypeptides, and encoding polynucleotides, are also provided herein. Various embodiments of the mutant T7 RNA polymerase can further reduce uninduced levels of expression and/or achieve as good or better levels of induced expression, as compared to a wild type T7 RNA polymerase. Also provided herein are host prokaryotic cells comprising a ZRY construct (i.e., a "ZRY strain"). Such ZRY strains can comprise wild-type T7 RNA polymerase or mutant T7 RNA polymerases.

One aspect described herein is a T7 RNA polymerase mutant polypeptide, and polynucleotides encoding such. In some embodiments, the mutant T7 RNA polymerase provides for reduced rates of uninduced expression in a T7 expression system compared to a wild type T7 RNA polymerase. In some embodiments, the mutant T7 RNA polymerase provides for comparable rates of induced expression in a T7 expression system compared to a wild type T7 RNA polymerase. In some embodiments, the mutant T7 RNA polymerase provides for both reduced rates of uninduced expression and comparable rates of induced expression in a T7 expression system compared to a wild type T7 RNA polymerase. As an example, uninduced and/or induced rates of expression of the mutant T7 RNA polymerase can be compared to a wild type T7 RNA polymerase of SEQ ID NO: 2.

Mutant T7 RNA polymerase described herein can be used in ZRY constructs, transformed host cells, and expression systems also described herein. These mutant T7 RNA polymerases can further reduce rates of uninduced expression in ZRY expression systems as compared to those using a wild type T7 RNA polymerase. These mutant T7 RNA polymerases can provide comparable, or increased, rates of induced expression in ZRY systems as compared to those using a wild type T7 RNA polymerase.

Design, generation, and testing of the variant nucleotides, and/or their encoded polypeptides, having the above required percent identities to polynucleotide SEQ ID NO: 1 or polypeptide SEQ ID NO: 2 and retaining the required polymerase activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the sequences T7 polymerase described herein and screen such for activity according to methods routine in the art. Generally, conservative substitutions can be made at any position so long as the required activity is retained.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[$Na^+$])+0.41 (fraction G/C content)−0.63(% formamide)−(600/l). Furthermore, the $T_m$, of a DNA:DNA hybrid is decreased by 1-1.5° C. for every 1% decrease in nucleotide identity (see e.g., Sambrook and Russel, 2006). In some embodiments, a mutant T7 RNA polymerase polynucleotide hybridizes under highly stringent conditions to a polynucleotide of SEQ ID NO: 1.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Various embodiments provide mutant T7 RNA polymerase having at least about 80% identity to a wild type T7 RNA polymerase, such as the polypeptide of SEQ ID NO: 2, encoded by the polynucleotide of SEQ ID NO: 1. For example, a mutant T7 RNA polymerase can have at least about 85%, at least about 90%, at least about 95%, at least about 96%, at least about 97%, at least about 98%, or at least about 99% identity to a wild type T7 RNA polymerase. Preferably, a mutant T7 RNA polymerase polypeptide has at least about 95% identity to polypeptide SEQ ID NO: 2. Preferably, a polynucleotide encoding a mutant T7 RNA polymerase has at least about 95% identity to polynucleotide SEQ ID NO: 1. The mutant T7 RNA polymerase retains RNA polymerase activity. In some embodiments, the mutant T7 RNA polymerase has reduced rates of uninduced expression and/or about the same or greater rates of induced expression in a T7 expression system compared to a T7 RNA polymerase of SEQ ID NO: 2.

Some embodiments of the mutant T7 RNA polymerase comprise at least one mutation at base 251, codon 84 (CGC to CAC, and Arg to His, respectively); at base 1240, codon 414 (ATC to GTC, and Ile to Val, respectively); at base 1958, codon 653 (GAT to GGT, and Asp to Gly, respectively); at base 2092, codon 698 (TGG to GGG, and Trp to Gly, respectively); or at base 2203, codon 735 (GTG to ATG, and Val to Met, respectively). For example, a mutant T7 RNA polymerase can comprise at least one mutationat base 251, codon 84 (CGC to CAC, and Arg to His, respectively) (e.g., SEQ ID NO: 3; SEQ ID NO: 4). As another example, a mutant T7 RNA polymerase can comprise at least one mutationat base 1240, codon 414 (ATC to GTC, and Ile to Val, respectively) (e.g., SEQ ID NO: 5; SEQ ID NO: 6). As another example, a mutant T7 RNA polymerase can comprise at least one mutationat base 1958, codon 653 (GAT to GGT, and Asp to Gly, respectively) (e.g., SEQ ID NO: 7; SEQ ID NO: 8). As another example, a mutant T7 RNA polymerase can comprise at least one mutationat base 2092, codon 698 (TGG to GGG, and Trp to Gly, respectively) (e.g., SEQ ID NO: 9; SEQ ID NO: 10). As another example, a mutant T7 RNA polymerase can comprise at least one mutationat base 2203, codon 735 (GTG to ATG, and Val to Met, respectively) (e.g., SEQ ID NO: 11; SEQ ID NO: 12).

Further embodiments of the mutant T7 RNA polymerase comprise at least two mutations at base 251, codon 84 (CGC to CAC, and Arg to His, respectively); at base 1240, codon 414 (ATC to GTC, and Ile to Val, respectively); at base 1958, codon 653 (GAT to GGT, and Asp to Gly, respectively); at base 2092, codon 698 (TGG to GGG, and Trp to Gly, respectively); or at base 2203, codon 735 (GTG to ATG, and Val to Met, respectively). It is understood that various embodiments can contain different combinations of the above mutations.

As an example, a mutant T7 RNA polymerase can include at least two mutations at base 251, codon 84 (CGC to CAC, and Arg to His, respectively) and base 1240, codon 414 (ATC to GTC, and Ile to Val, respectively) (e.g., SEQ ID NO: 13; SEQ ID NO: 14). As another example, a mutant T7 RNA polymerase can include at least two mutations at base 251, codon 84 (CGC to CAC, and Arg to His, respectively) and base 1958, codon 653 (GAT to GGT, and Asp to Gly, respectively) (e.g., SEQ ID NO: 15; SEQ ID NO: 16). As another example, a mutant T7 RNA polymerase can include at least two mutations at base 251, codon 84 (CGC to CAC, and Arg to His, respectively) and base 2092, codon 698 (TGG to GGG, and Trp to Gly, respectively) (e.g., SEQ ID NO: 17; SEQ ID NO: 18). As another example, a mutant T7 RNA polymerase can include at least two mutations at base 251, codon 84 (CGC to CAC, and Arg to His, respectively) and base 2203, codon 735 (GTG to ATG, and Val to Met, respectively) (e.g., SEQ ID NO: 19; SEQ ID NO: 20).

As another example, a mutant T7 RNA polymerase can include at least two mutations at base 1240, codon 414 (ATC to GTC, and Ile to Val, respectively) and base 1958, codon 653 (GAT to GGT, and Asp to Gly, respectively) (e.g., SEQ ID NO: 21; SEQ ID NO: 22). As another example, a mutant T7 RNA polymerase can include at least two mutations at base 1240, codon 414 (ATC to GTC, and Ile to Val, respectively) and base 2092, codon 698 (TGG to GGG, and Trp to Gly, respectively) (e.g., SEQ ID NO: 23; SEQ ID NO: 24). As another example, a mutant T7 RNA polymerase can include at least two mutations at base 1240, codon 414 (ATC to GTC, and Ile to Val, respectively) and base 2203, codon 735 (GTG to ATG, and Val to Met, respectively) (e.g., SEQ ID NO: 25; SEQ ID NO: 26).

As another example, a mutant T7 RNA polymerase can include at least two mutations at base 1958, codon 653 (GAT to GGT, and Asp to Gly, respectively) and base 2092, codon 698 (TGG to GGG, and Trp to Gly, respectively) (e.g., SEQ ID NO: 27; SEQ ID NO: 28). As another example, a mutant T7 RNA polymerase can include at least two mutations at base 1958, codon 653 (GAT to GGT, and Asp to Gly, respectively) and base 2203, codon 735 (GTG to ATG, and Val to Met, respectively) (e.g., SEQ ID NO: 29; SEQ ID NO: 30).

As another example, a mutant T7 RNA polymerase can include at least two mutations at base 2092, codon 698 (TGG to GGG, and Trp to Gly, respectively) and base 2203, codon 735 (GTG to ATG, and Val to Met, respectively) (e.g., SEQ ID NO: 31; SEQ ID NO: 32).

Further embodiments of the mutant T7 RNA polymerase comprise at least three mutations at base 251, codon 84 (CGC to CAC, and Arg to His, respectively); at base 1240, codon 414 (ATC to GTC, and Ile to Val, respectively); at base 1958, codon 653 (GAT to GGT, and Asp to Gly, respectively); at base 2092, codon 698 (TGG to GGG, and Trp to Gly, respectively); or at base 2203, codon 735 (GTG to ATG, and Val to Met, respectively). It is understood that various embodiments can contain different combinations of the above mutations.

As an example, a mutant T7 RNA polymerase can include at least three mutations at base 251, codon 84 (CGC to CAC, and Arg to His, respectively); base 1240, codon 414 (ATC to GTC, and Ile to Val, respectively); and base 1958, codon 653 (GAT to GGT, and Asp to Gly, respectively) (e.g., SEQ ID NO: 33; SEQ ID NO: 34). As another example, a mutant T7 RNA polymerase can include at least three mutations at base 251, codon 84 (CGC to CAC, and Arg to His, respectively); base 1240, codon 414 (ATC to GTC, and Ile to Val, respectively); and base 2092, codon 698 (TGG to GGG, and Trp to Gly, respectively) (e.g., SEQ ID NO: 35; SEQ ID NO: 36). As another example, a mutant T7 RNA polymerase can include at least three mutations at base 251, codon 84 (CGC to CAC, and Arg to His, respectively); base 1240, codon 414 (ATC to GTC, and Ile to Val, respectively); and base 2092, codon 698 (TGG to GGG, and Trp to Gly, respectively) (e.g., SEQ ID NO: 37; SEQ ID NO: 38).

As another example, a mutant T7 RNA polymerase can include at least three mutations at base 251, codon 84 (CGC to CAC, and Arg to His, respectively); base 1958, codon 653 (GAT to GGT, and Asp to Gly, respectively); and base 2092, codon 698 (TGG to GGG, and Trp to Gly, respectively) (e.g., SEQ ID NO: 39; SEQ ID NO: 40). As another example, a mutant T7 RNA polymerase can include at least three mutations at base 251, codon 84 (CGC to CAC, and Arg to His, respectively); base 1958, codon 653 (GAT to GGT, and Asp to Gly, respectively); and base 2203, codon 735 (GTG to ATG, and Val to Met, respectively) (e.g., SEQ ID NO: 41; SEQ ID NO: 42).

As another example, a mutant T7 RNA polymerase can include at least three mutations at base 251, codon 84 (CGC to CAC, and Arg to His, respectively); base 2092, codon 698 (TGG to GGG, and Trp to Gly, respectively); and base 2203, codon 735 (GTG to ATG, and Val to Met, respectively) (e.g., SEQ ID NO: 43; SEQ ID NO: 44).

As another example, a mutant T7 RNA polymerase can include at least three mutations at base 1240, codon 414 (ATC to GTC, and Ile to Val, respectively); base 1958, codon 653 (GAT to GGT, and Asp to Gly, respectively); and base 2092, codon 698 (TGG to GGG, and Trp to Gly, respectively) (e.g., SEQ ID NO: 45; SEQ ID NO: 46). As another example, a mutant T7 RNA polymerase can include at least three mutations at base 1240, codon 414 (ATC to GTC, and Ile to Val, respectively); base 1958, codon 653 (GAT to GGT, and Asp to Gly, respectively); and base 2203, codon 735 (GTG to ATG, and Val to Met, respectively) (e.g., SEQ ID NO: 47; SEQ ID NO: 48).

As another example, a mutant T7 RNA polymerase can include at least three mutations at base 1240, codon 414 (ATC to GTC, and Ile to Val, respectively); base 2092, codon 698 (TGG to GGG, and Trp to Gly, respectively); and base 2203, codon 735 (GTG to ATG, and Val to Met, respectively) (e.g., SEQ ID NO: 49; SEQ ID NO: 50).

As another example, a mutant T7 RNA polymerase can include at least three mutations at base 1958, codon 653 (GAT to GGT, and Asp to Gly, respectively); base 2092, codon 698 (TGG to GGG, and Trp to Gly, respectively); and base 2203, codon 735 (GTG to ATG, and Val to Met, respectively) (e.g., SEQ ID NO: 51; SEQ ID NO: 52).

Further embodiments of the mutant T7 RNA polymerase comprise at least four mutations at base 251, codon 84 (CGC to CAC, and Arg to His, respectively); at base 1240, codon 414 (ATC to GTC, and Ile to Val, respectively); at base 1958, codon 653 (GAT to GGT, and Asp to Gly, respectively); at base 2092, codon 698 (TGG to GGG, and Trp to Gly, respectively); or at base 2203, codon 735 (GTG to ATG, and Val to Met, respectively). It is understood that various embodiments can contain different combinations of the above mutations.

As an example, a mutant T7 RNA polymerase can include at least four mutations at base 251, codon 84 (CGC to CAC, and Arg to His, respectively); base 1240, codon 414 (ATC to GTC, and Ile to Val, respectively); base 1958, codon 653 (GAT to GGT, and Asp to Gly, respectively); and base 2092, codon 698 (TGG to GGG, and Trp to Gly, respectively) (e.g., SEQ ID NO: 53; SEQ ID NO: 54). As another example, a mutant T7 RNA polymerase can include at least four mutations at base 251, codon 84 (CGC to CAC, and Arg to His, respectively); base 1240, codon 414 (ATC to GTC, and Ile to Val, respectively); base 1958, codon 653 (GAT to GGT, and Asp to Gly, respectively); and base 2203, codon 735 (GTG to ATG, and Val to Met, respectively) (e.g., SEQ ID NO: 55; SEQ ID NO: 56). As another example, a mutant T7 RNA polymerase can include at least four mutations at base 251, codon 84 (CGC to CAC, and Arg to His, respectively); base 1240, codon 414 (ATC to GTC, and Ile to Val, respectively); base 2092, codon 698 (TGG to GGG, and Trp to Gly, respectively); and base 2203, codon 735 (GTG to ATG, and Val to Met, respectively) (e.g., SEQ ID NO: 57; SEQ ID NO: 58). As another example, a mutant T7 RNA polymerase can include at least four mutations at base 251, codon 84 (CGC to CAC, and Arg to His, respectively); base 1958, codon 653 (GAT to GGT, and Asp to Gly, respectively); base 2092, codon 698 (TGG to GGG, and Trp to Gly, respectively); and base 2203, codon 735 (GTG to ATG, and Val to Met, respectively) (e.g., SEQ ID NO: 59; SEQ ID NO: 60).

Further embodiments of the mutant T7 RNA polymerase comprise at least five mutations at base 251, codon 84 (CGC to CAC, and Arg to His, respectively); at base 1240, codon 414 (ATC to GTC, and Ile to Val, respectively); at base 1958, codon 653 (GAT to GGT, and Asp to Gly, respectively); at base 2092, codon 698 (TGG to GGG, and Trp to Gly, respectively); and at base 2203, codon 735 (GTG to ATG, and Val to Met, respectively). (e.g., SEQ ID NO: 61; SEQ ID NO: 62).

Figure 12:
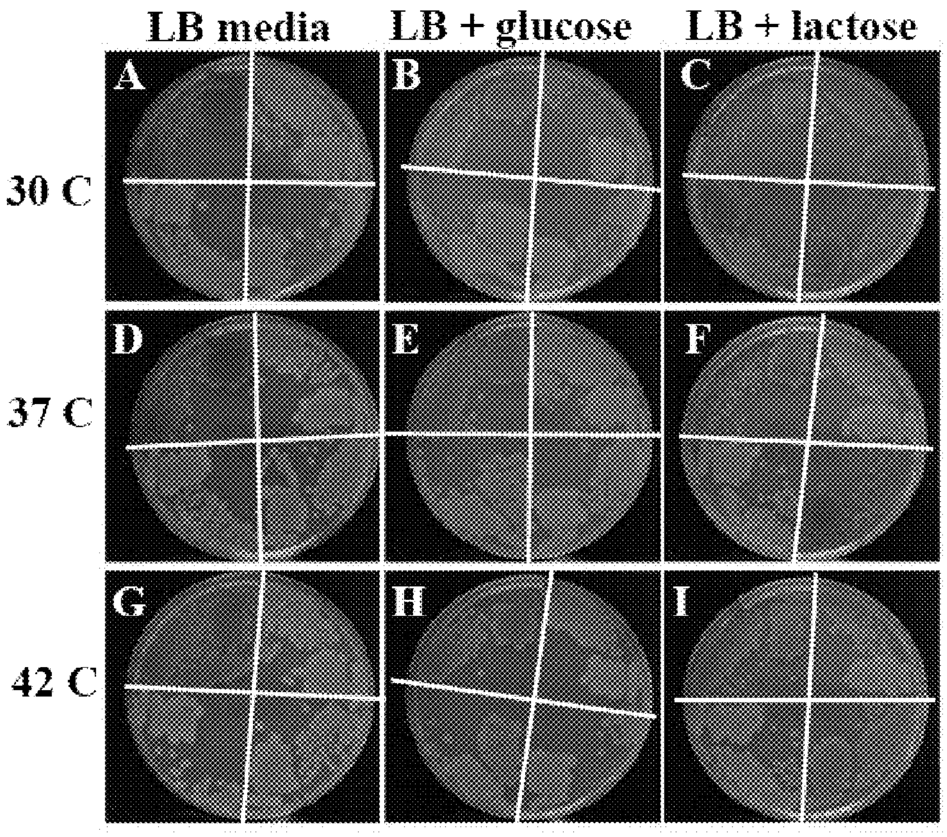
FIG. 12 shows photographs of four bacterial strains grown on three different types of solid agar media plates and at three different growth temperatures. The top row shows plates that were incubated at 30° Celsius, the middle row at 37 Celsius, and the bottom row at 42° Celcius. The different growth media are arranged by column. The first column shows bacteria growing on LB media, the second column shows bacteria growing on LB media supplemented with 0.2% glucose, the third column shows bacteria growing on LB media supplemented with 0.2% lactose. In all photographs, BL21 (DE3) is in the top left quadrant, strain WB466.15 is in the top right quadrant, strain WB478e is in the bottom left quadrant, and WB477f is in the bottom right quadrant. For details regarding methodology, see Example 10.

In some embodiments, the mutant T7 RNA polymerase is temperature-sensitive. In one embodiment, the mutant T7 RNA polymerase does not express a target polynucleotide sequence under control of a T7 promoter when grown at 37° Celsius, but the can express a target polynucleotide under the control of a T7 promoter when grown at 30° Celsius. This temperature-sensitive control of expression from the T7 promoter can be a desirable trait, and can allow increased control of the expression of genes regulated by the T7 promoter (see Example 10; Table 3; FIG. 12).

In some embodiments, the mutant T7 RNA polymerase is not a temperature-sensitive strain. In one embodiment, the mutant T7 RNA polymerase is capable of expressing a target polynucleotide under control of a T7 promoter when *E. coli* are grown at 37° Celsius. In another embodiment, mutant T7 RNA polymerase is capable of expressing a target polynucleotide under control of a T7 promoter when *E. coli* are grown at 42° Celsius. In another embodiment, the mutant T7 RNA polymerase is capable of expressing a target polynucleotide under control of a T7 promoter when *E. coli* are grown at 37° or 42° Celsius. The ability of a mutant T7 RNA polymerase to express a target polynucleotide from a T7 promoter when grown at the temperature at which *E. coli* are normally grown can be a desirable trait (see Example 10; Table 3).

polymerase binds the DNA to begin transcription of the polycistronic lac mRNA. Immediately downstream (towards Lac Z) of the promoter is the operator region. This operator can be bound by Lac I to prevent transcription of the polycistronic lac mRNA. Lac I is constitutively present at low levels in the bacterial cell, and, in the absence of lactose, constitutively bound to the operator in the lac regulatory region. When lactose is present in the cell, Lac I preferentially binds the lactose, which causes a conformational change in the Lac I protein and the consequent release of Lac I from the lac regulatory region.

Figure 9:
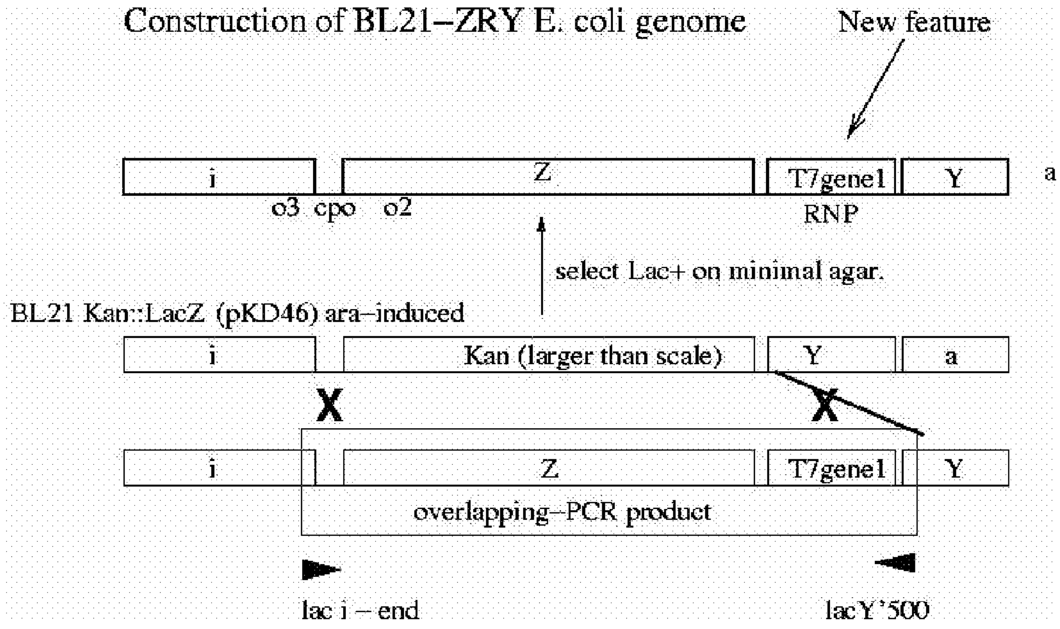
FIG. 9 is a diagram depicting recombination results in insertion of the T7 RNA polymerase gene between Z and Y, while leaving the lac control region unchanged.

A polynucleotide encoding a T7 RNA polymerase (e.g., T7 gene 1, SEQ ID NO: 1) or a mutant T7 RNA polymerase (as described above) can be inserted between the lac Z and lac Y of the lac operon by a variety of means known to the art (see e.g., FIG. 9). For example, design and construction of a ZRY strain can be according to the gene transplacement method of Datsenko and Wanner (2000) (see e.g., Example 3). Other suitable methods will be known to those skilled in the art.

In some embodiments, the lac control region is a wild-type lac control region. The wild-type lac operon control region

TABLE 1

T7 polymerase nucleotides and polypeptide residues at specified position corresponding to SEQ ID NO: 1 and SEQ ID NO: 2, respectively, for various strains

| | 251/84<br>251/84 | 1240/414<br>1240/414 | 1958/653<br>1958/653 | 2092/698<br>2092/698 | 2203/735<br>2203/735 |
|---|---|---|---|---|---|
| Wild type | CGC<br>Arg | ATC<br>Ile | GAT<br>Asp | TGG<br>Trp | GTG<br>Val |
| WB466.15 | (WT) | GTC<br>Val | (WT) | GGG<br>Gly | ATG<br>Met |
| WB477f | CAC<br>His | GTC<br>Val | GGT<br>Gly | GGG<br>Gly | (WT) |
| WB478e | (WT) | (WT) | (WT) | GGG<br>Gly | ATG<br>Met |

Another aspect is a ZRY construct in which a polynucleotide encoding a T7 RNA polymerase or mutant T7 RNA polymerase occurs between a lac Z polynucleotide sequence encoding β-galactosidase and a lac Y polynucleotide sequence (Y) encoding a β-galactoside permease, forming ZRY. ZRY is downstream of a wild-type lac control region. In various embodiments, the lac control region comprises a CAP binding site, a promoter, an operator, and a ribosome binding site. In various embodiments, the promoter of the lac control region is a lac-inducible and catabolite-repressible promoter recognized by a host cell polymerase. In various embodiments, the polynucleotide encoding the T7 RNA polymerase or mutant T7 RNA polymerase is under the control of the lac-inducible and catabolite-repressible promoter of the lac control region.

Upstream of the coding region, there are sequences that regulate the expression of the polycistronic lac mRNA. The lac control region, or regulatory region, (see e.g., SEQ ID NO.: 71, SEQ ID NO.: 72) comprises a CAP binding site, a promoter, and an operator (O1). The lac control region also comprises a ribosome binding site (i.e., a Shine-Delgarno sequence). Furthest upstream from the Lac Z gene is the CAP binding site. The CAP binding site binds CAP protein and recruites *E. coli*'s endogenous RNA polymerase to the lac promoter. The promoter is downstream (towards Lac Z) of the CAP binding site. The promoter is the site at which the RNA can reduce uninduced basal expression levels in the expression system. In some embodiments, the lac control region has a nucleotide sequence of SEQ ID NO: 71 or SEQ ID NO: 72. In some embodiments, the lac control region is a variant of SEQ ID NO: 71 or SEQ ID NO: 72 having at least 95% identity thereof having a functional CAP binding site, a promoter, an operator, and a ribosome binding site. In some embodiments, the lac control region comprises a the lac control region from *E. coli* strain BL21.

Strain BL21(DE3) was found in the present invention to have a non-canonical substitution within the lac regulatory region, at −1 of the transcription initiation site (see Example 3; SEQ ID NO. 72). In other *E. coli* strains in which this region has been sequenced, e.g. K12, this substitution does not exist (SEQ ID NO.: 71). In some embodiments, the substitution can be repaired, and thus is provided an improved regulation of expression of the lac operon (see Example 3; SEQ ID NO.: 71).

The Lac Z portion of the polycistronic lac mRNA encodes a β-galactosidase. Lac Z has been completely sequenced in many *E. coli* strains, including K12 (SEQ ID NO.: 63) and O157:H7 (SEQ ID NO.: 65). These nucleotide sequences encode polypeptides of SEQ ID NO.: 64 and SEQ ID NO.: 66, respectively.

In some embodiments, the lac Z polynucleotide comprises a nucleotide sequence of SEQ ID NO: 63 or SEQ ID NO: 65.

In some embodiments, the lac Z polynucleotide comprises a variant of SEQ ID NO: 63 or SEQ ID NO: 65 having at least 95% identity thereof encoding a polypeptide having β-galactosidase activity. In some embodiments, the lac Z polynucleotide comprises a nucleotide sequence encoding a polypeptide having an amino acid sequence of SEQ ID NO: 64 or SEQ ID NO: 65 and β-galactosidase activity, or a variant having at least 95% identity thereof and β-galactosidase activity. In some embodiments, the lac Z polynucleotide comprises a lac Z polynucleotide from *E. coli* strain BL21.

The Lac Y portion of the polycistronic lac mRNA encodes a β-galactoside permease. The Lac Y portion of the lac mRNA has been completely sequenced in many *E. coli* strains, including K12 (SEQ ID NO.: 67) and O157:H7 (SEQ ID NO.: 69). These polynucleotides encode proteins of SEQ ID NO.: 68 and SEQ ID NO.: 70, respectively.

In some embodiments, the lac Y polynucleotide comprises a nucleotide sequence of SEQ ID NO: 67 or SEQ ID NO: 69. In some embodiments, the lac Y polynucleotide comprises a variant of SEQ ID NO: 67 or SEQ ID NO: 69 having at least 95% identity thereof encoding a polypeptide having β-galactoside permease activity. In some embodiments, the lac Y polynucleotide comprises a nucleotide sequence encoding a polypeptide having an amino acid sequence of SEQ ID NO: 68 or SEQ ID NO: 70 and β-galactosidase activity, or a variant having at least 95% identity thereof and β-galactosidase activity. In some embodiments, the lac Y polynucleotide comprises a lac Y polynucleotide from *E. coli* strain BL21.

One aspect provides an expression system for producing a target polypeptide in a host cell. The expression system can comprise a T7 RNA polymerase or a mutant T7 RNA polymerase inserted between lac Z and lac Y, as described above. The expression system can further comprise a target promoter polynucleotide sequence recognized by the encoded T7 RNA polymerase, or mutant T7 RNA polymerase, of ZRY. The expression system can further comprise a target polynucleotide sequence encoding a target polypeptide, where the target polynucleotide sequence is under the control of the target promoter.

One aspect provides a prokaryotic host cell engineered to comprise a ZRY expression system. ZRY can be inserted into the host genome as an exogenous construct. Alternatively, ZRY can be engineered in the host genome from exogenous R and endogenous Z and/or Y elements.

The present invention can be used with a variety of suitable prokaryotic hosts. The ZRY portion can be genetically transferred to the host genome using, for example, the well-known method of P1 transduction. In some embodiments, the prokaryotic host is an *E. coli*. For example, suitable prokaryotic hosts include, but are not limited to, *E. coli* strains of BL21, C2566, DH1, DH4I, DH5, DH5I, DH5IF', DH5IMCR, DH10B, DH10B/p3, DH11S, C600, HB101, JM101, JM105, JM109, JM110, K38, MG1655, RR1, Y1088, Y1089, CSH18, ER1451, and ER1647. Other suitable hosts are known in the art (see e.g., Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253). Preferably, the host is a BL21 *E. coli* strain.

Expression vectors can be introduced into host cells using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253). For example, host strains can be conveniently tested for degree of control, leakiness of expression, and auto-induction capacity using a colorometric positive indicator, such as DsRed.T3 (see e.g., Examples 3, 5, 10). Furthermore, a colorometric positive indicator, such as DsRed.T3, can be employed to monitor auto-induction protocols employing strains described herein. As another example, luciferase can be used as an indicator (see Barnes, 1990). An advantage of luciferase is that no protein purification and concentration is necessary, and it can be assayed very sensitively (e.g., down to about one molecule per cell).

In one embodiment, the ZRY strain is WB456.7, which comprises a wild-type lac promoter and T7 polymerase gene 1 (SEQ ID NO: 1) inserted between lac Z and lac Y of the lac operon. Strain WB456.7 is privately deposited (available on request).

In one embodiment, the ZRY strain is WB466.15, which comprises a wild-type lac promoter and a mutant T7 polymerase gene (SEQ ID NO: 49) inserted between lac Z and lac Y of the lac operon. Strain WB466.15 is privately deposited (available on request). ZRY strain WB466.15 contains mutations at base 1240, codon 414 (ATC to GTC, and Ile to Val, respectively); at base 2092, codon 698 (TGG to GGG, and Trp to Gly, respectively); and at base 2203, codon 735 (GTG to ATG, and Val to Met, respectively) (SEQ ID NO: 49, SEQ ID NO: 50, respectively) (see Table 1).

In one embodiment of the invention, the ZRY strain is WB478e, which comprises a wild-type lac promoter and a mutant T7 polymerase gene (SEQ ID NO: 31) inserted between lac Z and lac Y of the lac operon. Strain WB478e is privately deposited (available upon request). ZRY strain WB478e contains mutations at base 2092, codon 698 (TGG to GGG, and Trp to Gly, respectively); and at base 2203, codon 735 (GTG to ATG, and Val to Met, respectively) (SEQ ID NO: 31, SEQ ID NO: 32, respectively) (see Table 1).

In one embodiment of the invention, the ZRY strain is WB477f, which comprises a wild-type lac promoter and mutant T7 polymerase gene (SEQ ID NO: 53) inserted between lac Z and lac Y of the lac operon. Strain WB477f is privately deposited (available upon request). Numbering from the first base of the ATG start codon of T7 gene 1 (SEQ ID NO: 1) which codes for T7 RNA polymerase (SEQ ID NO: 2), ZRY strain WB477f contains mutations at base 251, codon 84 (CGC to CAC, and Arg to His, respectively); at base 1240, codon 414 (ATC to GTC, and Ile to Val, respectively); at base 1958, codon 653 (GAT to GGT, and Asp to Gly, respectively); and at base 2092, codon 698 (TGG to GGG, and Trp to Gly, respectively) (SEQ ID NO: 53, SEQ ID NO: 54, respectively) (see Table 1).

In some embodiments, the ZRY strain is a temperature-sensitive strain. In one embodiment, the strain does not express a gene under control of the T7 promoter when grown at 37° Celsius, but the strain can express a gene under the control of the T7 promoter when grown at 30° Celsius. This temperature-sensitive control of expression from the T7 promoter can be a desirable trait, and can allow increased control of the expression of genes regulated by the T7 promoter (see Example 10; Table 3; FIG. 12).

In some embodiments, the ZRY strain is not a temperature-sensitive strain. In one embodiment, the strain is capable of expressing genes under control of the T7 promoter when *E. coli* are grown at 37° Celsius. In another embodiment, the strain is capable of expressing genes under control of the T7 promoter when *E. coli* are grown at 42° Celsius. In another embodiment, the strain is capable of expressing genes under control of the T7 promoter when *E. coli* are grown at 37° or 42° Celsius. The ability of a strain to express genes from the T7 promoter when grown at the temperature at which *E. coli* are normally grown can be a desirable trait (see Example 10; Table 3).

A ZRY strain can be utilized with a manual induction and/or auto-induction. An example of a manual induction system includes, but is not limited to, an expression system induced by the addition of IPTG. Preferably, the ZRY strain is utilized with an auto-induction expression system.

One aspect provides a method for producing a selected gene product in a host cell comprising a ZRY expression system. The ZRY construct, expression system, and host cell strain are as described above. The ZRY strain is engineered to express a target polypeptide of interest under control of a T7 promoter. As described above, a T7 RNA polymerase or mutant T7 RNA polymerase is inserted between lac Z and lac Y, and ZRY is downstream of a wild-type lac control region. The polynucleotide encoding the T7 RNA polymerase or mutant T7 RNA polymerase is under control of a lac-inducible and catabolite-repressible promoter of the wild-type lac control region. A target polynucleotide sequence encoding the target polypeptide is introduced into the host cell. The host cell comprising ZRY and the polynucleotide encoding the target polypeptide is incubated under conditions appropriate for expression of the T7 RNA polymerase and expression of the target polypeptide from the target polynucleotide sequence.

Protein production by auto-induction processes are well known in the art (see e.g., Studier (2005) Protein Expr Purif. 41(1), 207-234, incorporated herein by reference). Except as otherwise noted herein, therefore, the processes of the present invention can be carried out in accordance with such processes. Preferably, the auto-induction system utilizes the 5052 medium of Studier (2005) but a variety of other mediums known to the art can be utilized. For example, the medium need not contain any NZ amine nor yeast extract, for auto-induction in minimal medium, which allows more efficient labelling by special isotopes.

The improvements described herein are compatible with, and can therefore extend the anti-leak protection of, a variety of existing modifications to T7lac expression systems. For example, the various ZRY strain embodiments can be used with toxicity-resistant strains (e.g., Miroux & Walker, 1996; Lucigen); plasmid copy-number control for the T7 expression vector (e.g., pETcoco, Novagen); and additional lac operators to the pET vector series. As another example, a ZRY strain embodying comprising the wild-type T7 RNA polymerase can be used with coded inhibitors of the T7 RNA polymerase, such as T7 lysozymes (e.g., ancillary plasmids pLysS and pLysE).

Methods for expressing proteins in prokaryotic hosts are well-known to those of skill in the art (see e.g., Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253). One skilled in the art can adapt known methods for expressing proteins in prokaryotic hosts so as to incorporate aspects of the present invention. Generally, the expression method utilizes a T7 RNA polymerase and a T7lac promoter for control thereof. For example, the expression method can utilize a T7 RNA polymerase of SEQ ID NO: 2, encoded by SEQ ID NO: 1, or a variant thereof. As another example, the expression method can utilize a mutant T7 RNA polymerase, as described above.

Since some protein can be inactivated and/or insoluble in inclusion bodies at high, post-induction times, levels of protein at higher levels can be assessed in parallel on (total) protein gels to determine if they agree with the colorimetric or enzyme assays.

Isolation of expressed polypeptides can be according to methods known in the art (see e.g., Yakhnin et al., 1998). Polypeptides expressed in bacteria such as *E. coli* may be retained in the cytoplasm, typically as insoluble granules, or directed to the periplasmic space by a bacterial secretion sequence. Granules can be recovered when the cells are lysed and denatured using, for example, guanidine isothiocyanate or urea. Denatured polypeptide can then be refolded and dimerized by diluting the denaturant, such as by dialysis against a solution of urea and a combination of reduced and oxidized glutathione, followed by dialysis against a buffered saline solution. Polypeptide can be recovered from the periplasmic space in a soluble and functional form by disrupting the cells (e.g., sonication or osmotic shock) to release the contents of the periplasmic space and recovering the protein.

As an example, proteins can be isolated and purified using ethanol M extraction in the presence of ammonium sulfate. This method can be employed with a colorimetric indicator, such as DsRed.T3 protein, by lysing the cells with lysozyme and detergent rather than sonication. Also, at lower salt, the protein precipitates with ethanol without changing its spectral characteristics, providing an easy means to concentrate it.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Colored Protein Indicator

As a convenient and sensitive indicator of uninduced and induced expression levels, the plasmid pWB536 was constructed. Plasmid pWB536 expresses the fast-maturing T3 form of DsRed (Bevis & Glick, 2002) on the vector plasmid pET11 (Studier (1990)). A parallel control in a separate flask does not however ensure that a target protein culture is proceeding at the same pace, since some target proteins may compromise the metabolism of the cells when the expressed enzyme begins to appear. A single-copy indicator gene would more accurately reflect conditions inside the production cells, and would not excessively contaminate the preparation (compared to the target protein on a multi-copy plasmid).

Protein DsRed.T3 is fast-maturing (Bevis & Glick, 2002) and requires no additives; but fast-maturing as it is, it may be a lagging indicator, and/or it may have an odd dependence on the metabolism of the cell for proper maturation, which requires an oxidation step. Therefore, also tested was bacterial proteorhodopsin (which requires the addition of retinal for color maturation) as an alternate indicator. The clone was in a pET27b vector.

For current use of the DsRed indicator, the routine inoculation of an extra 500 ml flask with the expression strain carrying pWB536 is useful, with the same aeration (volume and shaking speed) as the flasks inoculated to express a research subject protein(s).

Figure 2:
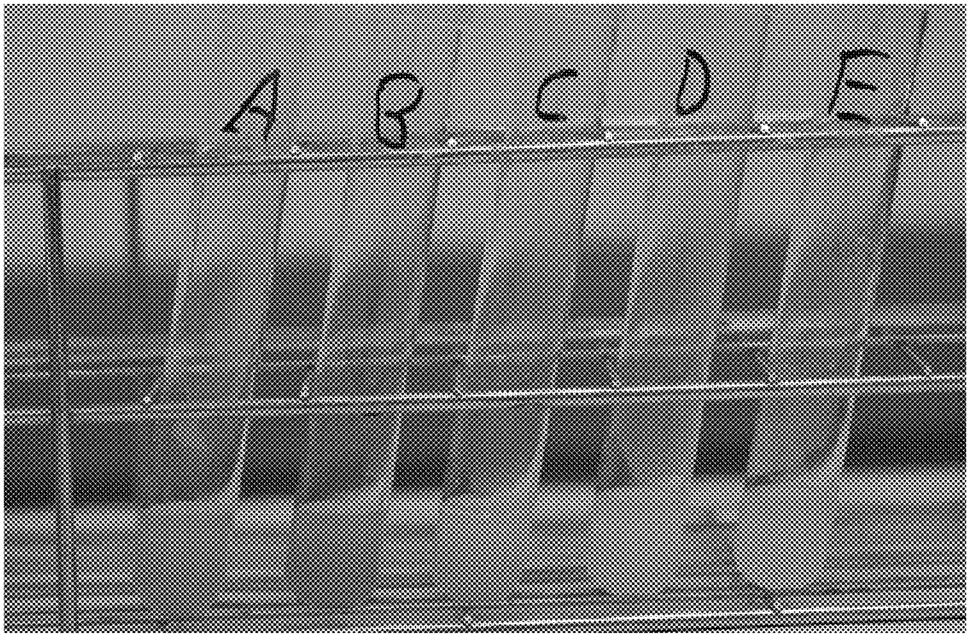
FIG. 2 is a photograph of 5 ml samples from the flasks shown in FIG. 1, where the intensity of the red coloring is an indicator of expression level. For details regarding methodology, see Example 1.

Even as a parallel culture in a separate flask, it was found that DsRed production by pWB536 is an illuminating control of whether conditions of time, temperature and aeration (culture volume) are adequate for good auto-induction. Studier (2005) did demonstrate and recommend workable flasks sizes (2.8 liter Fernbock), volume (500 ml), and shaking speed (350 rpm) and temperature (30° Celsius). But it has been found in the experiments described herein reasonable conditions that do not support auto-induction (e.g., 500 ml, 2 liter Erlynmeyer), where a ready color indicator is useful (see e.g., FIG. 2).

Demonstration of the use of this indicator gene is shown in FIG. 1. Four flasks (and a fifth not shown) were incubated under identical conditions (250 rpm, 30° C.) except for the shape of the flasks and the volume of auto-induction medium inoculated with pWB536/BL21(DE3). Flask A was 2.8 L Fernbach flask containing 1 L of medium; B was a 2.8 L Fernbach flask containing 500 ml of medium; C was a 2 L Erlynmeyer flask containing 500 ml of medium; D was a 2 L Erlynmeyer flask containing 1 L of medium; E was a 2 L Erlynmeyer flask with baffles containing 1 L of medium (see e.g., FIG. 1). The best expression level was the geometry recommended by Studier (2005) except no baffles (i.e., flask B) (see e.g., FIG. 2).

The bulk, visible-light color of the DsRed indicator can be used to assess expression levels. DsRed is also fluorescent, with excitation at both UV and 500 nm. A single rogue transcription event may allow the translation of several molecules of T7 RNA polymerase, resulting in perhaps hundreds of DsRed protein molecules being made. Therefore, when the expression system "leaks", some cells may be very fluorescent, and most will be dark. The "pop" of expression can then be diluted out as the cells divide. Single cells can be examined under a fluorescent microscope. Leakiness can be scored as fluorescent cells per thousand, or per 10,000.

Example 2

T7-Promoter/DsRed Gene

A T7-promoter/DsRed gene located near the lac operon is constructed and evaluated. The pT7-DsRed gene in inserted upstream of the lac operon, reading away from lacI (clockwise on the *E. coli* genome after 366734). The T7 terminator sequence from Studier's pET11 vector is included in an attempt to not disrupt the adjacent genes for propionate metabolism, only 77 bp away.

Example 3

Construction OF BL21-ZRY

Using BL21 DNA as a source of wild-type lac operon, a strain was constructed with map order Z,R,Y. The strain number is WB456. Unexpectedly, DNA sequence confirmation of two independent constructs (WB456.7 and WB456.12) revealed an uncharacterized mutation (Gaatt to Aaatt) at the base right before the start of mRNA transcription from the lac promoter. Additional DNA sequencing of DNA of parent strains determined that this mutation is present in the parental BL21. This mutation represents a potential contributor to the uninduced background in the standard Studier system using BL21(DE3). Another source of lac DNA (λplac5) was used to repeat the construction to see if the resulting strain exhibits noticeably tighter regulation.

Construction of BL21-ZRY proceeded in 2 phases, each using the gene transplacement method of Datsenko and Wanner (2000). This method uses PCR products with only ~40 bp of spanning homology on either side, but carrying a selectable marker. In brief, target bacteria carry plasmid pKD46 which has a Ts-replicon (therefore easily curable at 42 deg.) and which carries the recombination genes of phage lambda under arabinose control. Target bacteria are induced with 1 mM arabinose before they are made electrocompetent for transformation, so they can recombine with PCR product as shown in, for example, FIG. 9. The new DNA junction sequences are shown in, for example, FIG. 10. More detailed methodology is as follows.

Phase 1 of the construction of BL21-ZRY replaced the lacZ codons with a promoter and gene for kanamycin resistance, leaving intact the lac promoter and lacY,A. The donor kanR PCR product had 47 bp of lac operon target DNA homology on the left (promoter) side, up to 2 bases before the lacZ start codon. On the downstream side of the lacZ gene, the donor KanR PCR product had 52 bases of homology with lacY codons. It was amplified in 100 μl from 2 ng pKD4 (Datsenko and Wanner) plasmid DNA as template using overlapping primers NotZKD4 (1 pmole) and LacZnot1 (20 pmoles) on the left, and unZKD4' (1 pmole) and LacZnot-100 (20 pmoles) on the right. The resulting strain was designated WB448, was made lysogenic for P1CmClr100, and the temperature-induced P1 lysate was used and plated with citrate (Miller, 1970) to transduce BL21 to the phenotype of KanR and lac- to make the strain designated WB453.

Figure 3:
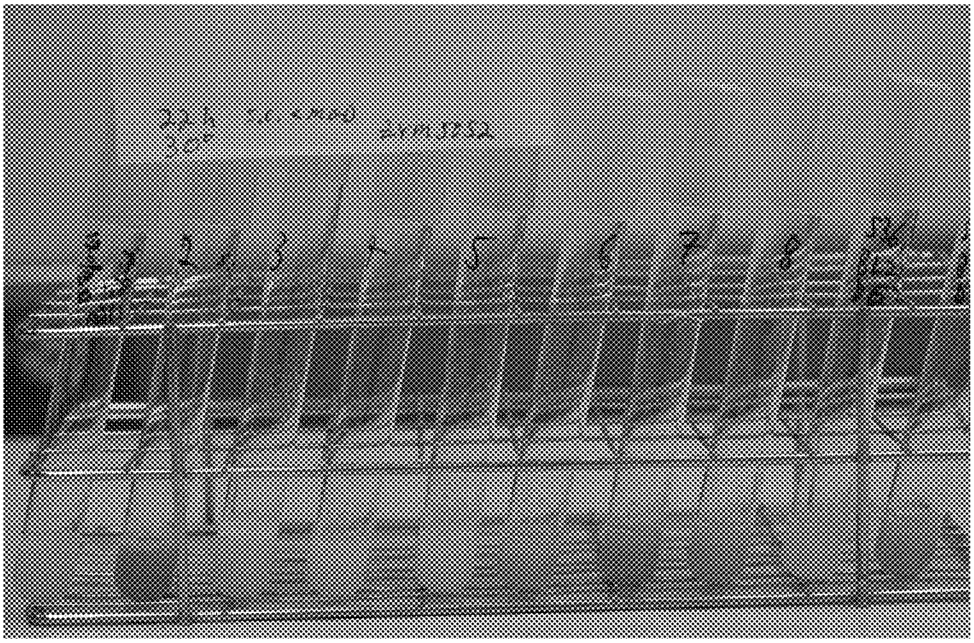
FIG. 3 is a photograph showing initial screen of genomic constructs transformed with pWB536 in an experiment to determine if they are auto-inducible. The two tubes on the right are negative and positive controls. The last tube on the right is the standard strain BL21(DE3)(pWB536). Strain/tube number 3, found by PCR to have no RNA polymerase gene, also serves as a negative control. Tube number 7 is BL21-ZRY strain pWB456.7. For details regarding methodology, see Example 3.
Figure 4:
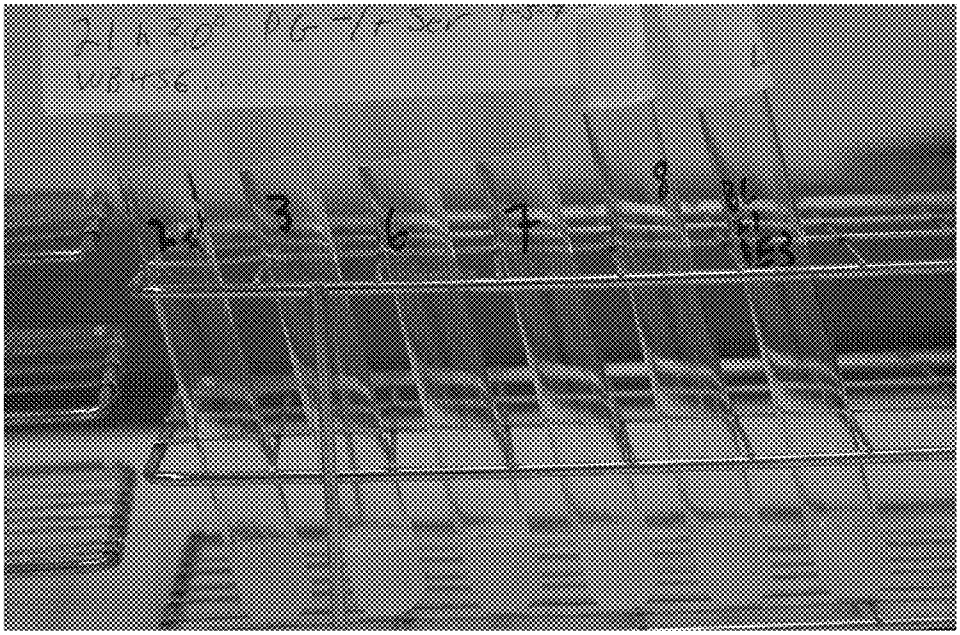
FIG. 4 is a series of photographs showing uninduced (leaky) levels of expression, providing a comparison of WB456.7 ("tube 7") vs. BL21(DE3).
Figure 4:
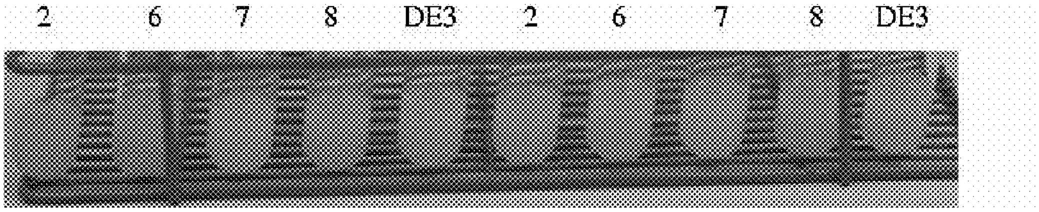
Figure 5:
FIG. 5 is a photograph showing expression levels. The top quadrant of the plate contains strain BL21-Al (Invitrogen). The left quadrant of the plate contains strain pWB456.7. The right quadrant of the plate contains BL21(DE3). The bottom quadrant of the plate contains unsatisfactory construct. Medium is LB agar using NZamine and yeast extract; 100 ug/ml Ticarcillin.

Phase 2 of the construction of BL21-ZRY used selection for growth on lactose as a carbon source to return lacZ to the operon in BL21, but now adjacent to T7 gene 1 (RNP) (SEQ ID NO: 1). The Z-RNP-Y amplicon was produced by overlapping PCR from 3 individual PCR products. Amplicon 1 carried lacZ with the p-o region on the left, and 33 bp of T7 gene 1 DNA on the right; amplicon 2 was the T7 gene 1 (SEQ ID NO: 1) with 33 bases of lacZ DNA on the left and 33 bases of lacY on the right; amplicon 3 was 501 bases of lacY with 33 bases of T7 gene 1 (SEQ ID NO: 1) on the left. Each gene was designed to have or retain Shine-Dalgarno sequences and start and stop codons, with minimal intergenic regions (see e.g., FIG. 10). These amplicons were precipitated with PEG to remove PCR primers. The overlapping PCR assembly step employed primer lacI-end on the left and primer lacY'500 on the right, with all 3 amplicons (approximately 2 ng each) as template, and KlentaqLA as the catalyzing DNA polymerase mixture (Barnes, 1994) at pH 7.9 to improve fidelity. The assembly (overlapping-) PCR exhibited a prominent product of the expected size (6.4 kb) in addition to several minor products. The whole PCR reaction was precipitated with PEG and approximately 200 ng of DNA was used for transformation without further purification. After transformation of WB453 (pKD46) previously induced with 1 mM arabinose (Datsenko and Wanner, 2000), and plating on lactose minimal (ML) plates, eight of 22 Lac+colonies (WB456.1-WB456.8) were picked for evaluation, and after purification these candidate strains were transformed with pWB536 to assess the presence of an inducible gene for T7 RNA polymerase. Four of the eight host strains could turn red after auto-induction in medium 5052 (see e.g., FIG. 3). One of these, WB456.7, exhibited the desired phenotype of lower expression than BL21(DE3) and BL21-Al on non-inducing media MG and MGD (see e.g., FIG. 4). Negative clone WB456.3, which was found (by whole-cell analytical PCR) to have no T7 RNP gene at all, was retained as a negative control.

The new strain, WB356.7, exhibits less leakiness in Studier's "uninducing" MGD medium compared to BL21(DE3), but the uninduced level is still detectable. The auto-induced level is at least, or greater than, that of BL21(DE3).

Example 4

Correction of BL21 SNP at Position-1 and Generation and Phenotype of WB466.15

As described above, the WB456.7 construct inherited from BL21 a non-canonical variant at position-1, right before the start of transcription at the lac promoter.

Figure 6:
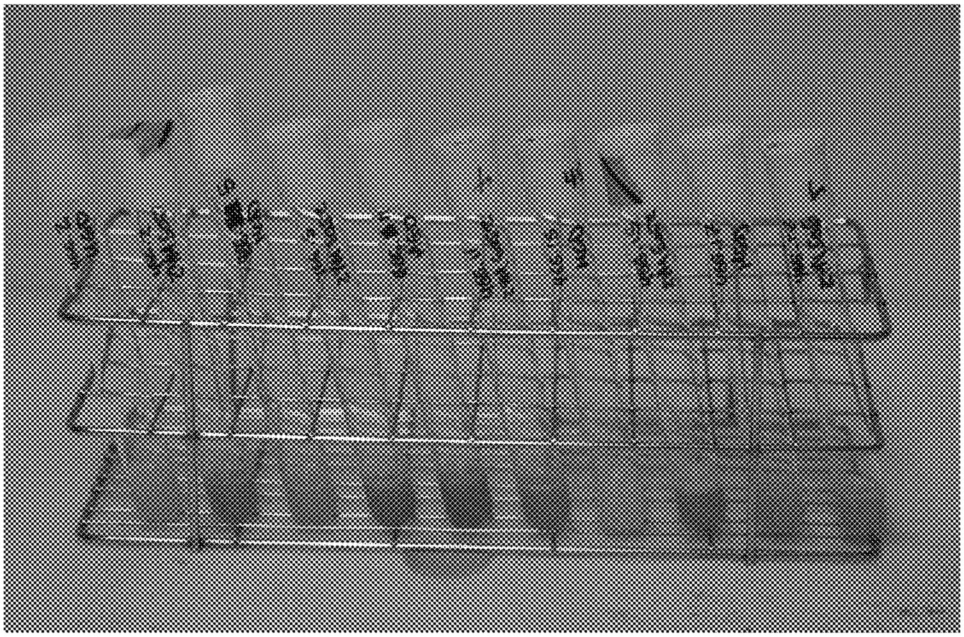
FIG. 6 is a photograph showing pairs of tubes labeled with their strain numbers WB466.nn. Odd tubes are uninduced (MGD medium). Even tubes are auto-induced (5052 medium). Outstanding performance is unexpectedly delivered by WB466.15, appearing as the seventh (uninduced) and eighth (auto-induced) tubes from the left. For details regarding methodology, see Example 4.

The construction was repeated using λplac5 as the source of lac control region and lacZ to make WB466. FIG. 6 shows pairs of cultures, MGD (non-inducing) and 5052 (auto-inducing). DNA sequencing shows that each of these strains had corrected the non-canonical base in the lac control region. But most still leaked in MGD. Although a BL21(DE3) and WB456.7 controls are not shown, it is thought that the non-canonical mutation is silent.

Figure 7:
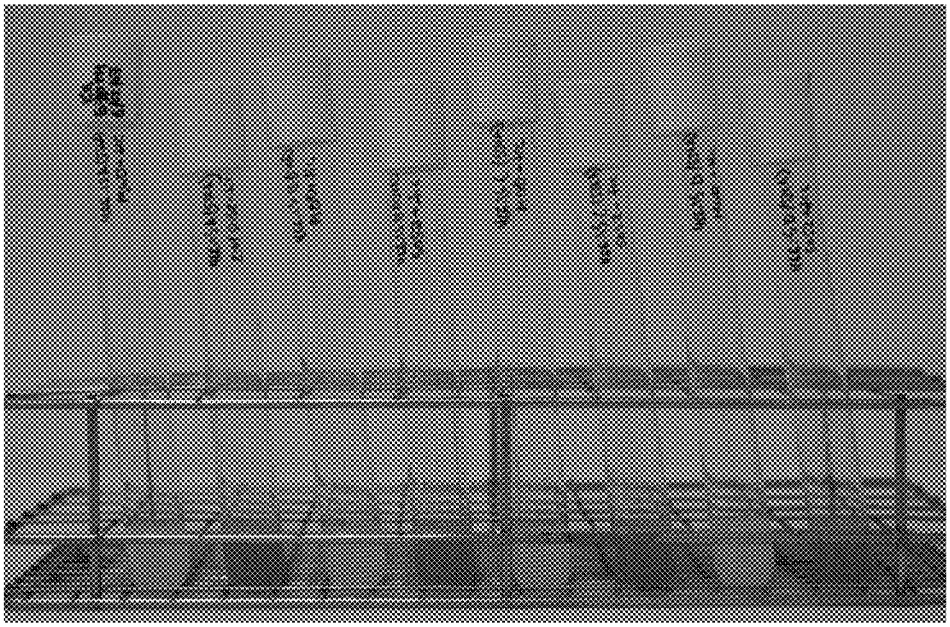
FIG. 7 is a photograph showing cured and then retransformed strain WB466.15. Odd numbered tubes (light-gray in color) are MGD medium, while dark-gray colored tubes are 5052 auto-induction medium. As shown in this figure, strain WB466.15 repeatably exhibits surprisingly tight control. As such, the initial result was not a mutant of the plasmid, and the new phenotype is stable. For details regarding methodology, see Example 4.

FIG. 6 also demonstrates that strain WB466.15 is off in MGD yet induces in 5052 medium. The plasmid was cured from WB466.14 (pWB536) and reintroduced (i.e., retransformed), and 4/4 transformants behave in the same desirable way (see e.g., FIG. 7). Curing the strain was straightforward as it grows as red colonies on LB+lactose agar (or lactose+ glucose minimal agar) without antibiotic, yet about 1% of the colonies are colorless, and prove to be cured and retransformable to the same phenotype. Simple replica plating of bacteria grown without antibiotic gives rise to the same frequency of cured WB466.15. The left 2 strains in FIG. 7 were cured by the latter method, and the right 2 strains were cured by the lactose agar method.

These results show that the initial result was not a mutant of the plasmid, and that the new WB466.15 phenotype is stable.

Figure 8:
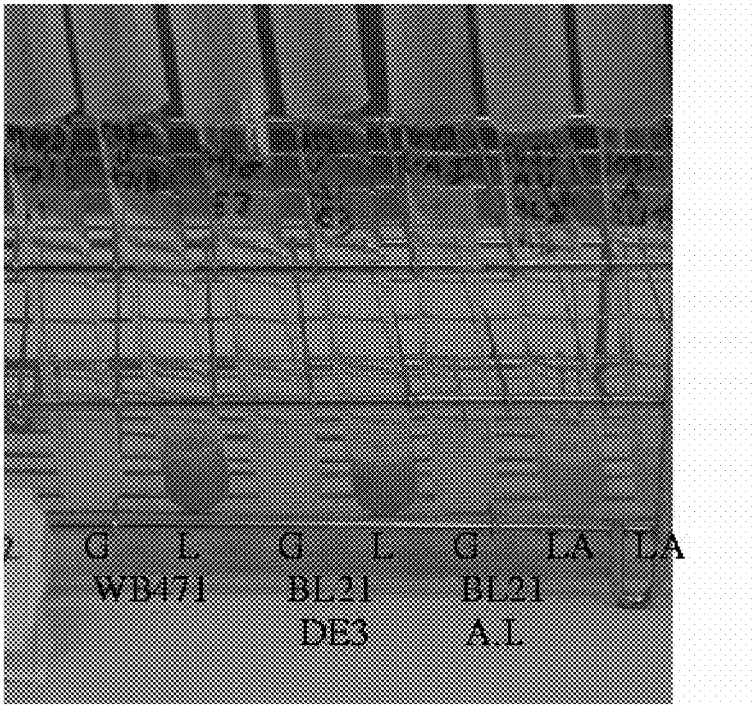
FIG. 8 is a photograph that compares the host construct ZRY transductant (P1.466.15/WB453) to the closest competing host, IBL21-Al (arabinose inducible) (Invitrogen) and to the standard BL21(DE3). G=MGD medium. L=5052 auto-induction medium. LA=5052+0.2% arabinose also to induce BL21-Al, as recommended by Invitrogen. For details regarding methodology, see Example 4.

FIG. 8 compares the host construct to the closest competing host, BL21-Al (arabinose inducible) (Invitrogen) and to the standard BL21(DE3). Surprisingly, BL21-Al reproducibly shows leaky expression in Studier's non-inducing MGD medium, almost to the extent of BL21(DE3). WB471 is the first P1 transductant.

WB446.15 shows temperature-sensitive expression of T7-DsRed (construct described in Example 2). WB446.15 does not express DsRed from the pT7-DsRed construct when grown at 37° Celsius, but does induce its expression at 30° Celsius.

It is thought that the performance phenotype maps close to the ZRY operon.

Example 5

Mapping of WB466.15

Mutant strain WB466.15 was generated as described above.

Strain WB466.15 is mapped first by P1 transduction which determines whether the advantageous phenotype is linked to the ZRY operon. The PCR recombination/transduction is repeated using WB466.15 DNA (SEQ ID NO: 49) as template, to answer whether the mutant(s) map to the 6433 bp of the PCR construct. The 6.4 kb construct is sequenced, beginning with the T7 gene 1 portion. If one or more non-canonical changes are found, each are re-introduced one at a time into the ZRY background. As described above, these genomic modifications of 6.4 kb are by application of the Datsenko & Wanner method, using strain WB453(pKD46), which could as well be named BL21(kan::ΔlacZ)(pKD46), as host recipient for the transduction/recombination.

On identification of mutability of the T7 RNA polymerase, additional forward mutations are created by using mutagenic PCR. While the least mutagenic conditions were used for the construction shown in FIG. 9, it required 30 cycles to amplify the T7 gene 1, then 18 more for the overlapping PCR assembly step, so that gene 1 underwent 48 cycles of PCR in total.

To screen for more mutations, a replica plating strategy can be employed. It has been observed that, surprisingly, there is not any deleterious growth effect, or selection, against cells which are expressing the indicator DsRed from the plasmid pWB536, in strain WB466.15 growing in the presence of lactose. The strains can even grow on lactose minimal medium with less than 1% segregation. In contrast, on lac minimal medium, BL21(DE3) segregates (loses the plasmid) at much higher frequency. Therefore the recombination in FIG. 9 is carried out in a background that already contains pWB536 (and also pKD119, a tetR version of pKD46). It is expected that not only will the recombinants be Lac+, they will be red. But on rich plates without glucose nor lactose that are left for 5 days, WB466.15(pWB536) cells refuse to turn red, yet hosts BL21(DE3) and even, 2 days later, WB456.7, do turn some color. New mutants in the class of WB455.15 are expected to be easy to screen for by replica plating.

If the mutation for very low leakiness is not linked to the ZRY operon, it is possible that a chromosomal rearrangement such as an inversion is responsible, since inversions occur in cultures of *E. coli* and *Salmonella* at high frequency (Schmid & Roth, 1983). The latter reference provides guidance for mapping an inversion.

Example 6

Assessment of Performance Compared to Other Expression Systems

Measurement of the control ratio over the time of auto-induction can assess the effectiveness of the various T7-expression systems versus the improvements described herein as well as those employed by others. The expression at a culture "time" of OD=1 or 2, during the glucose-utilizing phase before auto-induction, may be the most relevant to measure, vs. the final target protein level.

To increase our sensitivity and precision of detection of DsRed from uninduced cultures and auto-induction time points, the protein is purified, concentrated as necessary, and the absorbance read with a spectrophotometer or, more sensitively, the fluorescence with a fluorimeter. A ready purification method (shown for GFP by Yakhnin et al., 1998) involves ethanol extraction in the presence of 2.8 M ammonium sulfate. This method has been used effectively on DsRed.T3 protein, lysing the cells with lysozyme and detergent instead of the sonication used by Yakhnin et al. Also, at lower salt, the protein precipitates with ethanol without changing its spectral characteristics, providing an easy means to concentrate it.

As an alternate enzyme activity to assay precisely, β-galactosidase, as others have used for an analogous study (Setkas & Szybalski), is not used because β-galactosidase is used as part of auto-induction, upstream of the expression to be measured. CAT is avoided, because of the possibility of including the chloramphenicol-resistant plasmids pLysS and pLysE in these studies. Luciferase can be used (see Barnes, 1990). The advantage of luciferase is that no protein purification and concentration is necessary, and it can be assayed very sensitively (down to one molecule per cell at least).

Example 7

Generation and Phenotype of WB477f

The following example describes generation of WB477f and the resultant phenotype. Methods are according to those described in Examples 1-4, unless indicated otherwise. WB477f contains wild-type sequence upstream of the lac coding region.

Figure 11:
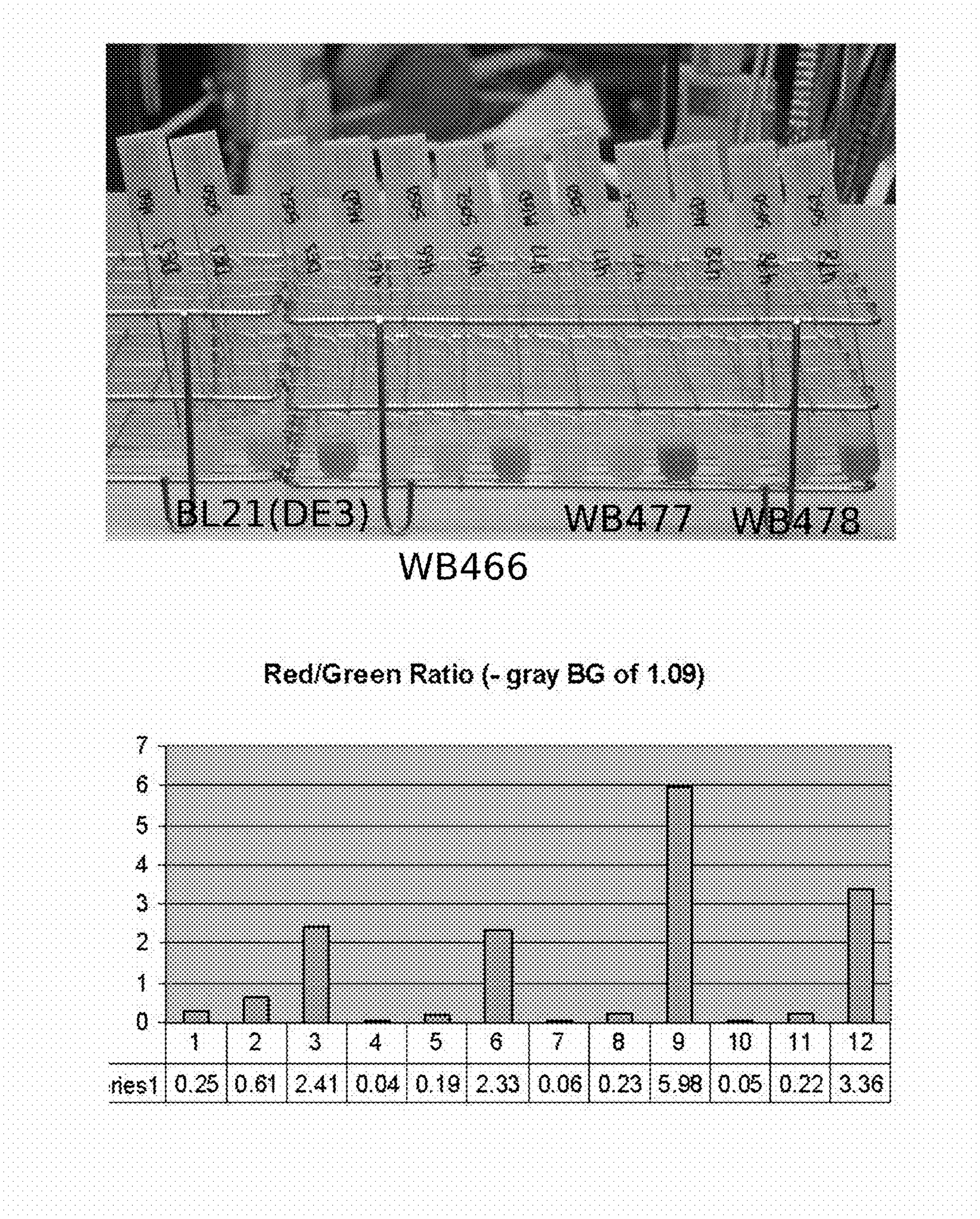
FIG. 11 is a photograph that demonstrates the behavior of the strain BL21(DE) in comparison to the improved behavior of ZRY strains WB466.15, WB477f and WB478e. Each strain is shown after growth in 3 different liquid media. The order of the media in each group is: MGD (non-inducing, Studier, 2005), 5050 (non-inducing) and 5052 (auto-inducing, Studier, 2005). For 5050 and 5052 media, the first "5" refers to 0.5% glycerol, the "05" refers to 0.05% glucose. The last digit in 5052 media refers to 0.2% lactose; in 5050 media there is no lactose, therefore the last digit is "0".

Four bacterial strains were each grown in three different culture media (see e.g., FIG. 11). The culture media are MGD (non-inducing), 5050 (non-inducing) and 5052 (auto-inducing) (see e.g., FIG. 11, from left to right, respectively). BL21 (DE) (see e.g., left-most tube in FIG. 11) shows leakiness in both of the non-inducing media (first and second tube on the left, evidenced by the light and medium gray color of the cultures), and robust induction in the auto-inducing medium (evidenced by the darker gray color of the culture). The second set of three cultures shows WB466.15 (fourth, fifth and sixth tubes from the left, see e.g., Example 4), which shows excellent repression in non-inducing media and robust induction in auto-inducing media. The third set of cultures (seventh, eighth and ninth tubes from the left) demonstrates that WB477f shows no induction of the T7 promoter in MGD and 5050 non-inducing media and robust auto-induction in 5052 media. The dark gray color seen in the culture of WB477f grown in 5052 media (ninth tube from the left) shows that the newly invented strain WB477f performs as well or better in auto-inducing media than BL21(DE).

WB477f also shows tight control of auto-induction when grown on agar media. When WB477f is grown on standard LB-agar growth medium with ticarcillin, there is no induction of DsRed.T3 even after days of growth. In contrast, BL21 (DE) shows induction of DsRed.T3 after only two days of growth (data not shown).

WB477f shows robust auto-induction at temperatures up to 42° Celsius.

It is thought that the performance phenotype described in this example maps close to the ZRY operon.

Example 8

Generation and Phenotype of WB478e

The following example describes generation of WB478e and the resultant phenotype. Methods are according to those described in Examples 1, 2, 3 and 4, unless indicated otherwise.

The bacterial strains were grown as follows: strain WB478e grown in MGD (non-inducing), 5050 (non-inducing), and 5052 (auto-inducing) media (right-most three cultures) (see e.g., FIG. 11). Results showed that strain WB478e represses expression from the T7 promoter in non-inducing media and induces T7-driven expression of DsRed.T3 in auto-inducing medium (see e.g., FIG. 11).

As described in Example 6, BL21(DE) shows a leaky phenotype in both of the non-inducing media and robust induction in the auto-inducing medium (first three tubes from the left in FIG. 11). The dark gray color of WB478e grown in auto-inducing medium demonstrates that this newly invented strain performs as good or better in these culture conditions than strain BL21(DE).

WB478e also shows tight control of auto-induction when grown on agar media. When WB478e is grown on standard LB-agar growth medium with ticarcillin, there is no induction of DsRed.T3 even after days of growth. In contrast, BL21 (DE) does show induction of DsRed.T3 after only two days of growth (data not shown).

WB478e shows temperature-sensitive expression of pT7-DsRed (construct described in Example 2). WB487e does not express DsRed from the pT7-DsRed construct when grown at 37° Celsius, but does induce its expression at 30° Celsius (data not shown).

It is thought that this performance phenotype maps close to the ZRY operon.

Example 9

Objective Analysis of Amount of DsRed in Various Strains Grown in Various Liquid Culture Conditions Described below is analysis of amount Of DsRed in various strains grown liquid culture conditions. Use of DsRed results in colorometric indications of expression level. Calculation of a red/green ratio from this data allows quantitative comparison of the amount of the red indicator protein DsRed.T3 (see e.g., FIG. 11).

To calculate the red/green ratio, a 21×21 square of pixels from the approximate center of an image of a culture was chosen. This image was evaluated by first scoring the red or green value of each individual pixel (range from 0 to 255). Then it was determined whether each pixel had a color value in the selected channel (either red or green) that was within ±5 of each of the other 440 pixels in the selected area. If the pixel being evaluated was within ±5 of this pixel for red, green and blue, it had a point added to its "similarity score." The same protocol was repeated for the evaluation of that pixel in reference to each of the other 440 pixels in the selected area. This evaluation was then repeated for each pixel in reference to every other pixel in the selected area for both color channels. After this evaluation, the pixel with the highest similarity score in each color channel was selected, and used as the representative red or green color of the selected area. Then all pixels with color scores within ±5 of that value were averaged to find the average red and green values in the selected area.

The red/green ratio for each selection was calculated by dividing the average calculated red value by the average calculated green value. To remove background noise from the calculation, a gray area in the upper right of the photo was chosen, and its red/green ratio was calculated. The red/green ratio of the background area was 1.09. That value was subtracted from the ratio that was calculated for the selection from each culture.

Example 10

Objective Analysis of the Amount of DsRed in Various Culture Strains Grown on Various Solid Media Almost every bacterial strain used in laboratory research is at some point propagated by growth in a culture plate that contains solidified agar medium. Strains BL21(DE3), WB466.15, WB477f, and WB478e were grown on three types of solid media and evaluated for the amount of DsRed.T3 that they express. Both inducing and non-inducing conditions were used. The strains were grown on regular LB medium, a standard *E. coli* growth medium. This medium should not induce expression of DsRed.T3. The strains were also grown on LB+0.2% glucose. This also should be a non-inducing medium. Further, the strains were grown on LB+0.2% lactose; this is the only culture condition which should induce transcription of the T7 polymerase gene 1 and therefore expression of DsRed.T3. The amount of DsRed.T3 expression was evaluated by the same calculation as described in Example 9, except that the subtracted background color value for this data was 1.079.

Results showed that strain BL21(DE3) has a significant amount of leaky induction when grown in LB medium, but the mutant strains show a very low level of expression of DsRed.T3 (see e.g., Table 2).

TABLE 2

Induction of strains at 30°, 37°, and 42° C. on non-inducing LB media

| LB media (non-inducing) | BL21(DE3) | WB466.15 | WB477f | WB478e |
|---|---|---|---|---|
| 30 Celsius | 3.41 | 0.08 | 0.15 | 0.15 |
| 37 Celsius | 3.63 | 0.09 | 0.06 | 0.13 |
| 42 Celsius | 2.03 | 0.09 | 0.09 | 0.14 |

Results also showed a similar result when the strains were grown in LB+0.2% glucose media (see e.g., Table 3). This medium should not induce expression of DsRed.T3; yet strain BL21(DE3) shows robust red color, whereas the mutant strains have significantly less expression of DsRed.T3.

TABLE 3

Induction of strains at 30°, 37°, and 42° C. on non-inducing media with glucose

| Media with glucose (non-inducing) | BL21(DE3) | WB466.15 | WB477f | WB478e |
|---|---|---|---|---|
| 30 Celsius | 1.04 | 0.03 | 0.13 | 0.07 |
| 37 Celsius | 1.46 | 0.08 | 0.12 | 0.12 |
| 42 Celsius | 1.45 | 0.08 | 0.1 | 0.13 |

Results also showed that strain BL21(DE) exhibited expected induction of DsRed.T3 expression when bacteria are grown on LB+0.2% lactose medium (see e.g., Table 4). Similarly, strains WB466.15, WB477f and WB478e also show robust induction of DsRed.T3 expression when grown on media in these conditions (see e.g., Table 4).

TABLE 4

Induction of strains at 30°, 37°, and 42° C. on inducing media with lactose

| Media with lactose (inducing) | BL21(DE3) | WB466.15 | WB477f | WB478e |
|---|---|---|---|---|
| 30 Celsius | 0.46 | 1.54 | 2.19 | 2.52 |
| 37 Celsius | 1.18 | 0.11 | 3.02 | 0.21 |
| 42 Celsius | 0.76 | 0.13 | 0.63 | 0.19 |

Taken together, these results show that bacterial strains comprising the mutant T7 polymerase genes described herein show a tighter regulation of the expression of DsRed.T3 from the pT7-DsRed construct than the BL21(DE3) strain.

Also shown is that expression of DsRed.T3 in strains WB466.15 and WB478e is further able to be controlled by the temperature at which the strains are grown (see e.g., Table 3). Even when these strains are grown in inducing medium (i.e., with lactose), if the strains are grown at temperatures above 30 Celsius, there is essentially no expression of DsRed.T3. This data shows the expression of proteins in a pT7 construct can be even more tightly controlled through the use of these temperature sensitive variants.

FIG. 12 shows the experimental data from which Tables 2-4 were derived. FIG. 12 shows the photographs of four bacterial strains grown on three different types of solid agar media plates and at three different growth temperatures. The top row shows plates that were incubated at 30° Celsius, the middle row at 37 Celsius, and the bottom row at 42 Celcius. The different growth media are arranged by column. In all photographs, BL21(DE3) is in the top left quadrant, strain WB466.15 is in the top right quadrant, strain WB478e is in the bottom left quadrant, and WB477f is in the bottom right quadrant. Panel I of FIG. 12 has a technical error in the streaking of cells, where the upper half of the top right quadrant is actually BL21(DE3) cells, and therefore is red and appears induced. But the red indication in the upper half of the top right quadrant is a result of contamination from the top left quadrant of the plate.

Results showed that, when grown on LB or LB+glucose agar media plates, strain BL21(DE3) shows an extremely red phenotype, i.e., that T7 RNA polymerase expression is not adequately repressed in this strain on non-inducing conditions. In contrast, strains WB466.15, WB478e, and WB477f show very little (if any) red color when grown on either LB or LB+glucose media (first or second columns, non-inducing conditions). Nevertheless, when these strains are grown on LB+lactose media (third column, inducing condition), at 30° Celsius (panel C), they all show a robust red phenotype, indicating expression of T7 RNA polymerase gene 1 and consequent expression of DsRed.T3.

Panels F and I of FIG. 12 also demonstrate that strains WB466.15 and WB478e show temperature-sensitivity in their ability to transcribe T7 RNA polymerase gene 1, i.e., these two strains do not acquire a red color when grown at 37° Celsius or 42° Celsius. Strain WB477f is able to transcribe T7 RNA polymerase gene 1 at both 37 Celsius and 42 Celsius, demonstrating that it is not temperature sensitive in the regulation of this gene's expression.

What is claimed is:

1. An isolated T7 RNA polymerase polypeptide comprising a variant of a polypeptide of SEQ ID NO: 2 wherein,
 the variant polypeptide is at least 95% identical to SEQ ID NO: 2 over the entire length thereof;
 the variant polypeptide having at least two mutations in SEQ ID NO: 2 independently selected from two or more of the amino acid residues consisting of:
 (i) 84, Arg to His (R84H);
 (ii) 414, Ile to Val (V414I);
 (iii) 653, Asp to Gly (D653G);
 (iv) 698, Trp to Gly (W698G); and
 (v) 735, Val to Met (V735M);
 the variant polypeptide has RNA polymerase activity; and
 the variant polypeptide has reduced rates of uninduced expression in a T7 expression system compared to a T7 RNA polymerase of SEQ ID NO: 2.

2. The isolated polypeptide of claim 1, wherein the variant polypeptide has about the same or greater rates of induced expression in a T7 expression system compared to a T7 RNA polymerase of SEQ ID NO: 2.

3. The isolated polypeptide of claim 1, wherein the variant polypeptide has lower rates of expression in a T7 expression system with non-inducing medium comprising 0.2% glucose media compared to a T7 RNA polymerase of SEQ ID NO: 2.

4. The isolated polypeptide of claim 1, wherein the variant polypeptide has a temperature sensitive phenotype, wherein the temperature sensitive phenotype comprises non-expression of a target polynucleotide sequence under control of a T7 promoter when grown at 37° Celsius; and expression of a target polynucleotide under the control of a T7 promoter when grown at 30° Celsius.

5. The isolated polypeptide of claim 1, wherein the variant polypeptide has a temperature non-sensitive phenotype, wherein the temperature non-sensitive phenotype comprises expression of a target polynucleotide under the control of a T7 promoter when grown at 37° Celsius.

6. The isolated polypeptide of claim 5, wherein the temperature non-sensitive phenotype comprises expression of a target polynucleotide under the control of a T7 promoter when grown at 42° Celsius.

7. The isolated polypeptide of claim 1, wherein the variant polypeptide
 (a) has at least two mutations selected from the group consisting of R84H, V4141, D653G, W698G, and V735M and (i) comprises an amino acid sequence selected from the group consisting of SEQ ID NO: 14; SEQ ID NO: 16; SEQ ID NO: 18; SEQ ID NO: 20; SEQ ID NO: 22; SEQ ID NO: 24; SEQ ID NO: 26; SEQ ID NO: 28; SEQ ID NO: 30; and SEQ ID NO: 32; or (ii) is encoded by a polynucleic acid comprising a nucleic acid sequence selected from the group consisting of SEQ ID NO: 13; SEQ ID NO: 15; SEQ ID NO: 17; SEQ ID NO: 19; and SEQ ID NO: 21; SEQ ID NO: 23; SEQ ID NO: 25; SEQ ID NO: 27; SEQ ID NO: 29; or SEQ ID NO: 31;
 (b) has at least three mutations selected from the group consisting of R84H, V4141, D653G, W698G, and V735M and (i) comprises an amino acid sequence selected from the group consisting of SEQ ID NO: 34; SEQ ID NO: 36; SEQ ID NO: 38; SEQ ID NO: 40; and SEQ ID NO: 42; SEQ ID NO: 44; SEQ ID NO: 46; SEQ ID NO: 48; SEQ ID NO: 50; and SEQ ID NO: 52; or (ii) is encoded by a polynucleic acid comprising a nucleic acid sequence selected from the group consisting of SEQ ID NO: 33; SEQ ID NO: 35; SEQ ID NO: 37; SEQ ID NO: 39; and SEQ ID NO: 41; SEQ ID NO: 43; SEQ ID NO: 45; SEQ ID NO: 47; SEQ ID NO: 49; and SEQ ID NO: 51;
 (c) has at least four mutations selected from the group consisting of R84H, V4141, D653G, W698G, and V735M and (i) comprises an amino acid sequence selected from the group consisting of SEQ ID NO: 54; SEQ ID NO: 56; SEQ ID NO: 58; and SEQ ID NO: 60; or (ii) is encoded by a polynucleic acid comprising a nucleic acid sequence selected from the group consisting of SEQ ID NO: 53; SEQ ID NO: 55; SEQ ID NO: 57; and SEQ ID NO: 59; or
 (d) has at least five mutations of R84H, V4141, D653G, W698G, and V735M and (i) comprises an amino acid sequence of SEQ ID NO: 62 or (ii) is encoded by a polynucleic acid comprising a nucleic acid sequence SEQ ID NO: 61.

8. The isolated polypeptide of claim 1, wherein the variant polypeptide (i) comprises an amino acid sequence selected from the group consisting of SEQ ID NO: 32; SEQ ID NO: 50; and SEQ ID NO: 54; or (ii) is encoded by a polynucleic acid comprising a nucleic acid sequence selected from the group consisting of SEQ ID NO: 31; SEQ ID NO: 49; and SEQ ID NO: 53.

9. The isolated polypeptide of claim 1, wherein the variant polypeptide comprises the R84H mutation.

10. The isolated polypeptide of claim 1, wherein the variant polypeptide comprises the D653G mutation.

11. The isolated polypeptide of claim 1, wherein the variant polypeptide comprises the W698G mutation.

12. The isolated polypeptide of claim 1, wherein the variant polypeptide comprises the V735M mutation.

13. The isolated polypeptide of claim 1, encoded by a nucleic acid sequence having at least 95% identity to that of SEQ ID NO: 1 and at least one mutation selected from the group consisting of:
 (i) a mutation at base 251 of CGC to CAC;
 (ii) a mutation at base 1240 of ATC to GTC;
 (iii) a mutation at base 1958 of GAT to GGT;
 (iv) a mutation at base 2092 of TGG to GGG; and
 (iii) a mutation at base 2203 of GTG to ATG.

14. An isolated polynucleic acid comprising a nucleic acid sequence having at least 95% identity to that of SEQ ID NO: 1 and at least one mutation selected from the group consisting of:
 (i) a mutation at base 251 of CGC to CAC;
 (ii) a mutation at base 1240 of ATC to GTC;
 (iii) a mutation at base 1958 of GAT to GGT;
 (iv) a mutation at base 2092 of TGG to GGG; and
 (iii) a mutation at base 2203 of GTG to ATG;
 wherein the isolated polynucleic encodes a polypeptide having T7 RNA polymerase activity.

15. An expression system for producing a target polypeptide in a prokaryotic host cell, the expression system comprising an isolated nucleic acid construct, the isolated nucleic acid construct comprising:

(i) a first polynucleotide sequence (R) comprising a sequence encoding the T7 RNA polymerase polypeptide of claim 1;
(ii) a lac Z polynucleotide sequence (Z) encoding β-galactosidase;
(iii) a lac Y polynucleotide sequence (Y) encoding a β-galactoside permease; and
(iv) a wild-type lac control region (C) comprising a CAP binding site, a promoter, an operator, and a ribosome binding site;
wherein (R) is located between (Z) and (Y), and ZRY is downstream of the wild-type lac control region (C); the promoter of (C) is a lac-inducible and catabolite-repressible promoter recognized by a prokaryotic host cell polymerase; and the polynucleotide sequence of (i), (ii), (iii), or (iv) is under the control of the lac-inducible and catabolite-repressible promoter.

16. The expression system of claim 15, wherein R further comprises a nucleotide sequence having at least 95% identity to that of SEQ ID NO: 1 and at least two mutations selected from the group consisting of (i) a mutation at base 1240 of ATC to GTC; (ii) a mutation at base 2092 of TGG to GGG; (iii) a mutation at base 2203 of GTG to ATG; (iv) a mutation at base 251 of CGC to CAC; and (v) a mutation at base 1958 of GAT to GGT; and the nucleotide sequence encodes the polypeptide of claim 1.

17. The expression system of claim 15, wherein
(a) the lac Z polynucleotide (Z) comprises
(i) a nucleotide sequence selected from group consisting of SEQ ID NO: 63 and SEQ ID NO: 65, or a variant having at least 95% identity thereof encoding a polypeptide having β-galactosidase activity;
(ii) a nucleotide sequence encoding a polypeptide having an amino acid sequence selected from the group consisting of SEQ ID NO: 64 and SEQ ID NO: 66 and β-galactosidase activity, or a variant having at least 95% identity thereof and β-galactosidase activity; or
(iii) a lac Z polynucleotide from *E. coli* strain BL21;
(b) the lac Y polynucleotide (Y) comprises
(i) a nucleotide sequence selected from group consisting of SEQ ID NO: 67 and SEQ ID NO: 69, or a variant having at least 95% identity thereof encoding a polypeptide having β-galactoside permease activity;
(ii) a nucleotide sequence encoding a polypeptide having an amino acid sequence selected from the group consisting of SEQ ID NO: 68 and SEQ ID NO: 70 and β-galactoside permease activity, or a variant having at least 95% identity thereof and having β-galactoside permease activity; or
(iii) a lac Y polynucleotide from *E. coli* strain BL21; or
(c) the wild-type lac control region (C) comprises a nucleotide sequence selected from the group consisting of SEQ ID NO: 71 and SEQ ID NO: 72, or a variant having at least 95% identity thereof having a functional CAP binding site, promoter, operator, and ribosome binding site.

18. The system of claim 15, further comprising a second polynucleotide sequence, the second polynucleotide sequence comprising
a target promoter polynucleotide sequence recognized by the encoded T7 RNA polymerase of the isolated nucleic acid construct; and
a target polynucleotide sequence encoding a target polypeptide;
wherein the target polynucleotide sequence is under the control of the target promoter polynucleotide sequence.

19. The system of claim 15, further comprising a host cell, wherein the host cell comprises the isolated nucleic acid construct; and optionally, one or more of the following conditions:
(a) the host cell further comprises a polynucleotide encoding a colorimetric positive indicator of T7 RNA polymerase expression;
(b) the host cell further comprises a polynucleotide encoding a DsRed.T3. colorimetric positive indicator of T7 RNA polymerase expression;
(c) the host cell is an *E. coli* cell;
(d) the host cell is an *E. coli* strain selected from the group consisting BL21, C2566, DH1, DH4I, DH5, DH5I, DH5IF', DH5IMCR, DH10B, DH10B/p3, DH11S, C600, HB101, JM101, JM105, JM109, JM110, K38, MG1655, RR1, Y1088, Y1089, CSH18, ER1451, and ER1647;
(e) wherein the host cell is *E. coli* strain BL21; or
(f) wherein the host cell is selected from the group consisting of *E. coli* strain WB456.7, *E. coli* strain WB466.15, *E. coli* strain WB478e, and *E. coli* strain WB477f.

20. A method for producing a target polypeptide in a host cell, the method comprising:
(a) introducing into a host cell the expression system of claim 15;
(b) introducing into the host cell a second polynucleotide sequence comprising
(i) a target polynucleotide sequence encoding a target polypeptide; and
(ii) a target promoter polynucleotide sequence recognized by the encoded T7 RNA polymerase of (R) of the expression system;
wherein the target polynucleotide sequence is under the control of the target promoter polynucleotide sequence;
(c) incubating the host cell under conditions appropriate for expression of a T7 RNA polymerase encoded by the first polynucleotide sequence (R) and expression of the target polypeptide from the target polynucleotide sequence.

21. An isolated T7 RNA polymerase polypeptide comprising a variant of a polypeptide of SEQ ID NO: 2 wherein,
the variant polypeptide is at least 95% identical to SEQ ID NO: 2 over the entire length thereof;
the variant polypeptide has a mutation in SEQ ID NO: 2 at amino acid residue 698, Trp to Gly (W698G);
the variant polypeptide has at least one additional mutation in SEQ ID NO: 2 at amino acid residue positions selected from the group consisting of:
(i) amino acid residue 84, Arg to His (R84H);
(ii) amino acid residue 414, Ile to Val (V414I);
(iii) amino acid residue 653, Asp to Gly (D653G); and
(iv) amino acid residue 735, Val to Met (V735M);
the variant polypeptide has RNA polymerase activity; and
the variant polypeptide has reduced rates of uninduced expression in a T7 expression system compared to a T7 RNA polymerase of SEQ ID NO: 2.

22. The isolated T7 RNA polymerase polypeptide of claim 21, wherein
the variant polypeptide comprises mutations selected from the group consisting of:
(i) amino acid residue 414, Ile to Val (V414I), amino acid residue 698, Trp to Gly (W698G), and amino acid residue 735, Val to Met (V735M);
(ii) amino acid residue 698, Trp to Gly (W698G) and amino acid residue 735, Val to Met (V735M); or (iii) amino acid residue 84, Arg to His (R84H), amino acid residue 414, Ile to Val (V414I), amino acid residue 653, Asp to Gly (D653G), and amino acid residue 698, Trp to Gly (W698G);

the variant polypeptide has RNA polymerase activity; and the variant polypeptide has reduced rates of uninduced expression in a T7 expression system compared to a T7 RNA polymerase of SEQ ID NO: 2.

23. The isolated T7 RNA polymerase polypeptide of claim 21, wherein the variant polypeptide comprises mutations selected from the group consisting of:

(i) amino acid residue 414, Ile to Val (V414I), amino acid residue 698, Trp to Gly (W698G), and amino acid residue 735, Val to Met (V735M); or (ii) amino acid residue 698, Trp to Gly (W698G) and amino acid residue 735, Val to Met (V735M);

the variant polypeptide has RNA polymerase activity;

the variant polypeptide has reduced rates of uninduced expression in a T7 expression system compared to a T7 RNA polymerase of SEQ ID NO: 2; and the variant polypeptide has temperature sensitivity in a T7 expression system compared to a T7 RNA polymerase of SEQ ID NO: 2.

* * * * *

SEQUENCE LISTING

<160> NUMBER OF SEQ ID NOS: 72

<210> SEQ ID NO 1
<211> LENGTH: 2652
<212> TYPE: DNA
<213> ORGANISM: T7 bacteriophage

<400> SEQUENCE: 1
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860

```
ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

```
<210> SEQ ID NO 2
<211> LENGTH: 883
<212> TYPE: PRT
<213> ORGANISM: T7 bacteriophage

<400> SEQUENCE: 2

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

-continued

```
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
```

-continued

```
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 3
<211> LENGTH: 2652
<212> TYPE: DNA
<213> ORGANISM: T7 bacteriophage

<400> SEQUENCE: 3

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac acatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780
```

```
ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

```
<210> SEQ ID NO 4
<211> LENGTH: 883
<212> TYPE: PRT
<213> ORGANISM: T7 bacteriophage

<400> SEQUENCE: 4

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30
```

-continued

```
Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
```

-continued

```
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880
```

-continued

Ala Phe Ala

<210> SEQ ID NO 5
<211> LENGTH: 2652
<212> TYPE: DNA
<213> ORGANISM: T7 bacteriophage

<400> SEQUENCE: 5
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggccg tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagcgttcag tcatgacgct ggcttacggg 1920
tccaaagagt tcggcttccg tcaacaagtg ctggaagata ccattcagcc agctattgat 1980
tccggcaagg gtctgatgtt cactcagccg aatcaggctg ctggatacat ggctaagctg 2040

-continued atttgggaat ctgtgagcgt gacggtggta gctgcggttg aagcaatgaa ctggcttaag 2100
tctgctgcta agctgctggc tgctgaggtc aaagataaga agactggaga gattcttcgc 2160
aagcgttgcg ctgtgcattg ggtaactcct gatggtttcc ctgtgtggca ggaatacaag 2220
aagcctattc agacgcgctt gaacctgatg ttcctcggtc agttccgctt acagcctacc 2280
attaacacca acaaagatag cgagattgat gcacacaaac aggagtctgg tatcgctcct 2340
aactttgtac acagccaaga cggtagccac cttcgtaaga ctgtagtgtg ggcacacgag 2400
aagtacggaa tcgaatcttt tgcactgatt cacgactcct tcggtaccat tccggctgac 2460
gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 6
<211> LENGTH: 883
<212> TYPE: PRT
<213> ORGANISM: T7 bacteriophage

<400> SEQUENCE: 6

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val

-continued

```
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685
```

-continued

```
Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 7
<211> LENGTH: 2652
<212> TYPE: DNA
<213> ORGANISM: T7 bacteriophage

<400> SEQUENCE: 7

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac gcatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960
```

-continued

```
aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

```
<210> SEQ ID NO 8
<211> LENGTH: 883
<212> TYPE: PRT
<213> ORGANISM: T7 bacteriophage

<400> SEQUENCE: 8

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
```

-continued

```
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495
```

```
Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 9
<211> LENGTH: 2652
<212> TYPE: DNA

-continued

<213> ORGANISM: T7 bacteriophage

<400> SEQUENCE: 9

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
```

```
attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

<210> SEQ ID NO 10
<211> LENGTH: 883
<212> TYPE: PRT
<213> ORGANISM: T7 bacteriophage

<400> SEQUENCE: 10

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300
```

-continued

```
Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720
```

-continued

```
Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 11
<211> LENGTH: 2652
<212> TYPE: DNA
<213> ORGANISM: T7 bacteriophage

<400> SEQUENCE: 11

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac gcatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780

ctggctggca tctctccgat gttccaacct tgcgtagttc ctcctaagcc gtggactggc     840

attactggtg gtggctattg ggctaacggt cgtcgtcctc tggcgctggt gcgtactcac     900

agtaagaaag cactgatgcg ctacgaagac gtttacatgc ctgaggtgta caaagcgatt     960

aacattgcgc aaaacaccgc atggaaaatc aacaagaaag tcctagcggt cgccaacgta    1020

atcaccaagt ggaagcattg tccggtcgag gacatccctg cgattgagcg tgaagaactc    1080

ccgatgaaac cggaagacat cgacatgaat cctgaggctc tcaccgcgtg gaaacgtgct    1140

gccgctgctg tgtaccgcaa ggacaaggct cgcaagtctc gccgtatcag ccttgagttc    1200
```

```
atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 12
<211> LENGTH: 883
<212> TYPE: PRT
<213> ORGANISM: T7 bacteriophage

<400> SEQUENCE: 12

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110
```

```
Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525
```

```
Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 13
<211> LENGTH: 2652
<212> TYPE: DNA
<213> ORGANISM: T7 bacteriophage

<400> SEQUENCE: 13

```
atgaacacga ttaacatcgc taagaacgac ttctctgaca tcgaactggc tgctatcccg     60

ttcaacactc tggctgacca ttacggtgag cgtttagctc gcgaacagtt ggcccttgag    120
```

```
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac acatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggccg tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
```

-continued gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 14
<211> LENGTH: 883
<212> TYPE: PRT
<213> ORGANISM: T7 bacteriophage

<400> SEQUENCE: 14

Met Asn Thr Ile Asn Ile Ala Lys Asn Asp Phe Ser Asp Ile Glu Leu
1 5 10 15

Ala Ala Ile Pro Phe Asn Thr Leu Ala Asp His Tyr Gly Glu Arg Leu
20 25 30

Ala Arg Glu Gln Leu Ala Leu Glu His Glu Ser Tyr Glu Met Gly Glu
35 40 45

Ala Arg Phe Arg Lys Met Phe Glu Arg Gln Leu Lys Ala Gly Glu Val
50 55 60

Ala Asp Asn Ala Ala Ala Lys Pro Leu Ile Thr Thr Leu Leu Pro Lys
65 70 75 80

Met Ile Ala His Ile Asn Asp Trp Phe Glu Glu Val Lys Ala Lys Arg
85 90 95

Gly Lys Arg Pro Thr Ala Phe Gln Phe Leu Gln Glu Ile Lys Pro Glu
100 105 110

Ala Val Ala Tyr Ile Thr Ile Lys Thr Thr Leu Ala Cys Leu Thr Ser
115 120 125

Ala Asp Asn Thr Thr Val Gln Ala Val Ala Ser Ala Ile Gly Arg Ala
130 135 140

Ile Glu Asp Glu Ala Arg Phe Gly Arg Ile Arg Asp Leu Glu Ala Lys
145 150 155 160

His Phe Lys Lys Asn Val Glu Glu Gln Leu Asn Lys Arg Val Gly His
165 170 175

Val Tyr Lys Lys Ala Phe Met Gln Val Val Glu Ala Asp Met Leu Ser
180 185 190

Lys Gly Leu Leu Gly Gly Glu Ala Trp Ser Ser Trp His Lys Glu Asp
195 200 205

Ser Ile His Val Gly Val Arg Cys Ile Glu Met Leu Ile Glu Ser Thr
210 215 220

Gly Met Val Ser Leu His Arg Gln Asn Ala Gly Val Val Gly Gln Asp
225 230 235 240

Ser Glu Thr Ile Glu Leu Ala Pro Glu Tyr Ala Glu Ala Ile Ala Thr
245 250 255

Arg Ala Gly Ala Leu Ala Gly Ile Ser Pro Met Phe Gln Pro Cys Val
260 265 270

Val Pro Pro Lys Pro Trp Thr Gly Ile Thr Gly Gly Gly Tyr Trp Ala
275 280 285

Asn Gly Arg Arg Pro Leu Ala Leu Val Arg Thr His Ser Lys Lys Ala
290 295 300

Leu Met Arg Tyr Glu Asp Val Tyr Met Pro Glu Val Tyr Lys Ala Ile
305 310 315 320

Asn Ile Ala Gln Asn Thr Ala Trp Lys Ile Asn Lys Lys Val Leu Ala
325 330 335

-continued

```
Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
```

-continued

```
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 15
<211> LENGTH: 2652
<212> TYPE: DNA
<213> ORGANISM: T7 bacteriophage

<400> SEQUENCE: 15

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac acatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380
```

-continued

```
aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

```
<210> SEQ ID NO 16
<211> LENGTH: 883
<212> TYPE: PRT
<213> ORGANISM: T7 bacteriophage

<400> SEQUENCE: 16

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140
```

-continued

```
Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
```

```
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 17
<211> LENGTH: 2652
<212> TYPE: DNA
<213> ORGANISM: T7 bacteriophage

<400> SEQUENCE: 17

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac acatcaacga ctggtttgag gaagtgaaag ctaagcgcgg caagcgcccg     300
```

-continued

```
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652
```

<210> SEQ ID NO 18
<211> LENGTH: 883
<212> TYPE: PRT
<213> ORGANISM: T7 bacteriophage

<400> SEQUENCE: 18

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
```

-continued

```
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800
```

```
Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 19
<211> LENGTH: 2652
<212> TYPE: DNA
<213> ORGANISM: T7 bacteriophage

<400> SEQUENCE: 19

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac acatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620
```

-continued

```
tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 20
<211> LENGTH: 883
<212> TYPE: PRT
<213> ORGANISM: T7 bacteriophage

<400> SEQUENCE: 20

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
```

-continued

```
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605
```

```
Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 21
<211> LENGTH: 2652
<212> TYPE: DNA
<213> ORGANISM: T7 bacteriophage

<400> SEQUENCE: 21

```
atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac gcatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540
```

-continued

```
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggccg tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaaggta ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652
```

<210> SEQ ID NO 22
<211> LENGTH: 883
<212> TYPE: PRT
<213> ORGANISM: T7 bacteriophage

<400> SEQUENCE: 22

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415
```

-continued

```
Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830
```

-continued

```
Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 23
<211> LENGTH: 2652
<212> TYPE: DNA
<213> ORGANISM: T7 bacteriophage

<400> SEQUENCE: 23

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac gcatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggccg tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800
```

-continued

```
aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa cgggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652


<210> SEQ ID NO 24
<211> LENGTH: 883
<212> TYPE: PRT
<213> ORGANISM: T7 bacteriophage

<400> SEQUENCE: 24

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

-continued

```
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640
```

```
Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 25
<211> LENGTH: 2652
<212> TYPE: DNA
<213> ORGANISM: T7 bacteriophage

<400> SEQUENCE: 25

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac gcatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720
```

-continued

```
tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggccg tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

<210> SEQ ID NO 26
<211> LENGTH: 883
<212> TYPE: PRT
<213> ORGANISM: T7 bacteriophage

<400> SEQUENCE: 26

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30
```

-continued

```
Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445
```

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe

-continued 865 870 875 880

Ala Phe Ala

<210> SEQ ID NO 27
<211> LENGTH: 2652
<212> TYPE: DNA
<213> ORGANISM: T7 bacteriophage

<400> SEQUENCE: 27
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagcgttcag tcatgacgct ggcttacggg 1920
tccaaagagt tcggcttccg tcaacaagtg ctggaaggta ccattcagcc agctattgat 1980
tccggcaagg gtctgatgtt cactcagccg aatcaggctg ctggatacat ggctaagctg 2040

```
atttgggaat ctgtgagcgt gacggtggta gctgcggttg aagcaatgaa cgggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 28
<211> LENGTH: 883
<212> TYPE: PRT
<213> ORGANISM: T7 bacteriophage

<400> SEQUENCE: 28

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255
```

-continued

```
Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
```

-continued

```
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 29
<211> LENGTH: 2652
<212> TYPE: DNA
<213> ORGANISM: T7 bacteriophage

<400> SEQUENCE: 29

```
atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac gcatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960
```

```
aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

<210> SEQ ID NO 30
<211> LENGTH: 883
<212> TYPE: PRT
<213> ORGANISM: T7 bacteriophage

<400> SEQUENCE: 30

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60
```

```
Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
```

-continued

```
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 31
<211> LENGTH: 2652

<212> TYPE: DNA
<213> ORGANISM: T7 bacteriophage

<400> SEQUENCE: 31

```
atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac gcatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780

ctggctggca tctctccgat gttccaacct tgcgtagttc ctcctaagcc gtggactggc     840

attactggtg gtggctattg ggctaacggt cgtcgtcctc tggcgctggt gcgtactcac     900

agtaagaaag cactgatgcg ctacgaagac gtttacatgc ctgaggtgta caaagcgatt     960

aacattgcgc aaaacaccgc atggaaaatc aacaagaaag tcctagcggt cgccaacgta    1020

atcaccaagt ggaagcattg tccggtcgag gacatccctg cgattgagcg tgaagaactc    1080

ccgatgaaac cggaagacat cgacatgaat cctgaggctc tcaccgcgtg gaaacgtgct    1140

gccgctgctg tgtaccgcaa ggacaaggct cgcaagtctc gccgtatcag ccttgagttc    1200

atgcttgagc aagccaataa gtttgctaac cataaggcca tctggttccc ttacaacatg    1260

gactggcgcg gtcgtgttta cgctgtgtca atgttcaacc cgcaaggtaa cgatatgacc    1320

aaaggactgc ttacgctggc gaaaggtaaa ccaatcggta aggaaggtta ctactggctg    1380

aaaatccacg gtgcaaactg tgcgggtgtc gataaggttc cgttccctga gcgcatcaag    1440

ttcattgagg aaaaccacga gaacatcatg gcttgcgcta agtctccact ggagaacact    1500

tggtgggctg agcaagattc tccgttctgc ttccttgcgt tctgctttga gtacgctggg    1560

gtacagcacc acggcctgag ctataactgc tcccttccgc tggcgtttga cgggtcttgc    1620

tctggcatcc agcacttctc cgcgatgctc cgagatgagg taggtggtcg cgcggttaac    1680

ttgcttccta gtgaaaccgt tcaggacatc tacgggattg ttgctaagaa agtcaacgag    1740

attctacaag cagacgcaat caatgggacc gataacgaag tagttaccgt gaccgatgag    1800

aacactggtg aaatctctga gaaagtcaag ctgggcacta aggcactggc tggtcaatgg    1860

ctggcttacg gtgttactcg cagtgtgact aagcgttcag tcatgacgct ggcttacggg    1920

tccaaagagt tcggcttccg tcaacaagtg ctggaagata ccattcagcc agctattgat    1980

tccggcaagg gtctgatgtt cactcagccg aatcaggctg ctggatacat ggctaagctg    2040

atttgggaat ctgtgagcgt gacggtggta gctgcggttg aagcaatgaa cgggcttaag    2100

tctgctgcta agctgctggc tgctgaggtc aaagataaga agactggaga gattcttcgc    2160

aagcgttgcg ctgtgcattg ggtaactcct gatggtttcc ctatgtggca ggaatacaag    2220
```

-continued

```
aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

```
<210> SEQ ID NO 32
<211> LENGTH: 883
<212> TYPE: PRT
<213> ORGANISM: T7 bacteriophage

<400> SEQUENCE: 32

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
```

```
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720
```

-continued

```
Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 33
<211> LENGTH: 2652
<212> TYPE: DNA
<213> ORGANISM: T7 bacteriophage

<400> SEQUENCE: 33

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac acatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140
```

```
gccgctgctg tgtaccgcaa ggacaaggct cgcaagtctc gccgtatcag ccttgagttc   1200

atgcttgagc aagccaataa gtttgctaac cataaggccg tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

<210> SEQ ID NO 34
<211> LENGTH: 883
<212> TYPE: PRT
<213> ORGANISM: T7 bacteriophage

<400> SEQUENCE: 34

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
```

-continued

```
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525
```

```
Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 35
<211> LENGTH: 2652
<212> TYPE: DNA
<213> ORGANISM: T7 bacteriophage

<400> SEQUENCE: 35

```
atgaacacga ttaacatcgc taagaacgac ttctctgaca tcgaactggc tgctatcccg      60
```

-continued

```
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac acatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggccg tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
```

```
gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652


<210> SEQ ID NO 36
<211> LENGTH: 883
<212> TYPE: PRT
<213> ORGANISM: T7 bacteriophage

<400> SEQUENCE: 36

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335
```

Val Ala Asn Val Ile Thr Lys Trp Lys His Cys Pro Val Glu Asp Ile
340 345 350

Pro Ala Ile Glu Arg Glu Glu Leu Pro Met Lys Pro Glu Asp Ile Asp
355 360 365

Met Asn Pro Glu Ala Leu Thr Ala Trp Lys Arg Ala Ala Ala Ala Val
370 375 380

Tyr Arg Lys Asp Lys Ala Arg Lys Ser Arg Arg Ile Ser Leu Glu Phe
385 390 395 400

Met Leu Glu Gln Ala Asn Lys Phe Ala Asn His Lys Ala Val Trp Phe
405 410 415

Pro Tyr Asn Met Asp Trp Arg Gly Arg Val Tyr Ala Val Ser Met Phe
420 425 430

Asn Pro Gln Gly Asn Asp Met Thr Lys Gly Leu Leu Thr Leu Ala Lys
435 440 445

Gly Lys Pro Ile Gly Lys Glu Gly Tyr Tyr Trp Leu Lys Ile His Gly
450 455 460

Ala Asn Cys Ala Gly Val Asp Lys Val Pro Phe Pro Glu Arg Ile Lys
465 470 475 480

Phe Ile Glu Glu Asn His Glu Asn Ile Met Ala Cys Ala Lys Ser Pro
485 490 495

Leu Glu Asn Thr Trp Trp Ala Glu Gln Asp Ser Pro Phe Cys Phe Leu
500 505 510

Ala Phe Cys Phe Glu Tyr Ala Gly Val Gln His His Gly Leu Ser Tyr
515 520 525

Asn Cys Ser Leu Pro Leu Ala Phe Asp Gly Ser Cys Ser Gly Ile Gln
530 535 540

His Phe Ser Ala Met Leu Arg Asp Glu Val Gly Gly Arg Ala Val Asn
545 550 555 560

Leu Leu Pro Ser Glu Thr Val Gln Asp Ile Tyr Gly Ile Val Ala Lys
565 570 575

Lys Val Asn Glu Ile Leu Gln Ala Asp Ala Ile Asn Gly Thr Asp Asn
580 585 590

Glu Val Val Thr Val Thr Asp Glu Asn Thr Gly Glu Ile Ser Glu Lys
595 600 605

Val Lys Leu Gly Thr Lys Ala Leu Ala Gly Gln Trp Leu Ala Tyr Gly
610 615 620

Val Thr Arg Ser Val Thr Lys Arg Ser Val Met Thr Leu Ala Tyr Gly
625 630 635 640

Ser Lys Glu Phe Gly Phe Arg Gln Gln Val Leu Glu Asp Thr Ile Gln
645 650 655

Pro Ala Ile Asp Ser Gly Lys Gly Leu Met Phe Thr Gln Pro Asn Gln
660 665 670

Ala Ala Gly Tyr Met Ala Lys Leu Ile Trp Glu Ser Val Ser Val Thr
675 680 685

Val Val Ala Ala Val Glu Ala Met Asn Gly Leu Lys Ser Ala Ala Lys
690 695 700

Leu Leu Ala Ala Glu Val Lys Asp Lys Lys Thr Gly Glu Ile Leu Arg
705 710 715 720

Lys Arg Cys Ala Val His Trp Val Thr Pro Asp Gly Phe Pro Val Trp
725 730 735

Gln Glu Tyr Lys Lys Pro Ile Gln Thr Arg Leu Asn Leu Met Phe Leu
740 745 750

```
Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 37
<211> LENGTH: 2652
<212> TYPE: DNA
<213> ORGANISM: T7 bacteriophage

<400> SEQUENCE: 37

atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac acatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggccg tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380
```

```
aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaagata ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 38
<211> LENGTH: 883
<212> TYPE: PRT
<213> ORGANISM: T7 bacteriophage

<400> SEQUENCE: 38

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140
```

-continued

```
Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560
```

```
Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 39
<211> LENGTH: 2652
<212> TYPE: DNA
<213> ORGANISM: T7 bacteriophage

<400> SEQUENCE: 39

```
atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac acatcaacga ctggtttgag gaagtgaaag ctaagcgcgg caagcgcccg     300
```

```
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgggatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
```

```
gcgttcgcgt aa                                                        2652


<210> SEQ ID NO 40
<211> LENGTH: 883
<212> TYPE: PRT
<213> ORGANISM: T7 bacteriophage

<400> SEQUENCE: 40

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365
```

-continued

```
Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
```

-continued

```
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 41
<211> LENGTH: 2652
<212> TYPE: DNA
<213> ORGANISM: T7 bacteriophage

<400> SEQUENCE: 41

```
atgaacacga ttaacatcgc taagaacgac ttctctgaca tcgaactggc tgctatcccg     60

ttcaacactc tggctgacca ttacggtgag cgtttagctc gcgaacagtt ggcccttgag    120

catgagtctt acgagatggg tgaagcacgc ttccgcaaga tgtttgagcg tcaacttaaa    180

gctggtgagg ttgcggataa cgctgccgcc aagcctctca tcactaccct actccctaag    240

atgattgcac acatcaacga ctggtttgag gaagtgaaag ctaagcgcgg caagcgcccg    300

acagccttcc agttcctgca agaaatcaag ccggaagccg tagcgtacat caccattaag    360

accactctgg cttgcctaac cagtgctgac aatacaaccg ttcaggctgt agcaagcgca    420

atcggtcggg ccattgagga cgaggctcgc ttcggtcgta tccgtgacct tgaagctaag    480

cacttcaaga aaaacgttga ggaacaactc aacaagcgcg tagggcacgt ctacaagaaa    540

gcatttatgc aagttgtcga ggctgacatg ctctctaagg gtctactcgg tggcgaggcg    600

tggtcttcgt ggcataagga agactctatt catgtaggag tacgctgcat cgagatgctc    660

attgagtcaa ccggaatggt tagcttacac cgccaaaatg ctggcgtagt aggtcaagac    720

tctgagacta tcgaactcgc acctgaatac gctgaggcta tcgcaacccg tgcaggtgcg    780

ctggctggca tctctccgat gttccaacct tgcgtagttc ctcctaagcc gtggactggc    840

attactggtg gtggctattg ggctaacggt cgtcgtcctc tggcgctggt gcgtactcac    900

agtaagaaag cactgatgcg ctacgaagac gtttacatgc ctgaggtgta caaagcgatt    960

aacattgcgc aaaacaccgc atggaaaatc aacaagaaag tcctagcggt cgccaacgta   1020

atcaccaagt ggaagcattg tccggtcgag gacatccctg cgattgagcg tgaagaactc   1080

ccgatgaaac cggaagacat cgacatgaat cctgaggctc tcaccgcgtg gaaacgtgct   1140

gccgctgctg tgtaccgcaa ggacaaggct cgcaagtctc gccgtatcag ccttgagttc   1200

atgcttgagc aagccaataa gtttgctaac cataaggcca tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560
```

```
gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 42
<211> LENGTH: 883
<212> TYPE: PRT
<213> ORGANISM: T7 bacteriophage

<400> SEQUENCE: 42

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175
```

-continued

```
Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
```

-continued

```
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 43
<211> LENGTH: 2652
<212> TYPE: DNA
<213> ORGANISM: T7 bacteriophage

<400> SEQUENCE: 43

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac acatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480
```

cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagcgttcag tcatgacgct ggcttacggg 1920
tccaaagagt tcggcttccg tcaacaagtg ctggaagata ccattcagcc agctattgat 1980
tccggcaagg gtctgatgtt cactcagccg aatcaggctg ctggatacat ggctaagctg 2040
atttgggaat ctgtgagcgt gacggtggta gctgcggttg aagcaatgaa cgggcttaag 2100
tctgctgcta agctgctggc tgctgaggtc aaagataaga agactggaga gattcttcgc 2160
aagcgttgcg ctgtgcattg ggtaactcct gatggtttcc ctatgtggca ggaatacaag 2220
aagcctattc agacgcgctt gaacctgatg ttcctcggtc agttccgctt acagcctacc 2280
attaacacca acaaagatag cgagattgat gcacacaaac aggagtctgg tatcgctcct 2340
aactttgtac acagccaaga cggtagccac cttcgtaaga ctgtagtgtg ggcacacgag 2400
aagtacggaa tcgaatcttt tgcactgatt cacgactcct tcggtaccat tccggctgac 2460
gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 44
<211> LENGTH: 883
<212> TYPE: PRT
<213> ORGANISM: T7 bacteriophage

<400> SEQUENCE: 44

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe

-continued

```
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830
```

```
Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 45
<211> LENGTH: 2652
<212> TYPE: DNA
<213> ORGANISM: T7 bacteriophage

<400> SEQUENCE: 45

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac gcatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780

ctggctggca tctctccgat gttccaacct tgcgtagttc ctcctaagcc gtggactggc     840

attactggtg gtggctattg ggctaacggt cgtcgtcctc tggcgctggt gcgtactcac     900

agtaagaaag cactgatgcg ctacgaagac gtttacatgc ctgaggtgta caaagcgatt     960

aacattgcgc aaaacaccgc atggaaaatc aacaagaaag tcctagcggt cgccaacgta    1020

atcaccaagt ggaagcattg tccggtcgag gacatccctg cgattgagcg tgaagaactc    1080

ccgatgaaac cggaagacat cgacatgaat cctgaggctc tcaccgcgtg gaaacgtgct    1140

gccgctgctg tgtaccgcaa ggacaaggct cgcaagtctc gccgtatcag ccttgagttc    1200

atgcttgagc aagccaataa gtttgctaac cataaggccg tctggttccc ttacaacatg    1260

gactggcgcg gtcgtgttta cgctgtgtca atgttcaacc cgcaaggtaa cgatatgacc    1320

aaaggactgc ttacgctggc gaaaggtaaa ccaatcggta aggaaggtta ctactggctg    1380

aaaatccacg gtgcaaactg tgcgggtgtc gataaggttc cgttccctga gcgcatcaag    1440

ttcattgagg aaaaccacga gaacatcatg gcttgcgcta agtctccact ggagaacact    1500

tggtgggctg agcaagattc tccgttctgc ttccttgcgt tctgctttga gtacgctggg    1560

gtacagcacc acggcctgag ctataactgc tcccttccgc tggcgtttga cgggtcttgc    1620

tctggcatcc agcacttctc cgcgatgctc cgagatgagg taggtggtcg cgcggttaac    1680

ttgcttccta gtgaaaccgt tcaggacatc tacgggattg ttgctaagaa agtcaacgag    1740

attctacaag cagacgcaat caatgggacc gataacgaag tagttaccgt gaccgatgag    1800
```

```
aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa cgggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

<210> SEQ ID NO 46
<211> LENGTH: 883
<212> TYPE: PRT
<213> ORGANISM: T7 bacteriophage

<400> SEQUENCE: 46

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
```

-continued

```
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640
```

Ser Lys Glu Phe Gly Phe Arg Gln Gln Val Leu Glu Gly Thr Ile Gln
645 650 655

Pro Ala Ile Asp Ser Gly Lys Gly Leu Met Phe Thr Gln Pro Asn Gln
660 665 670

Ala Ala Gly Tyr Met Ala Lys Leu Ile Trp Glu Ser Val Ser Val Thr
675 680 685

Val Val Ala Ala Val Glu Ala Met Asn Gly Leu Lys Ser Ala Ala Lys
690 695 700

Leu Leu Ala Ala Glu Val Lys Asp Lys Lys Thr Gly Glu Ile Leu Arg
705 710 715 720

Lys Arg Cys Ala Val His Trp Val Thr Pro Asp Gly Phe Pro Val Trp
725 730 735

Gln Glu Tyr Lys Lys Pro Ile Gln Thr Arg Leu Asn Leu Met Phe Leu
740 745 750

Gly Gln Phe Arg Leu Gln Pro Thr Ile Asn Thr Asn Lys Asp Ser Glu
755 760 765

Ile Asp Ala His Lys Gln Glu Ser Gly Ile Ala Pro Asn Phe Val His
770 775 780

Ser Gln Asp Gly Ser His Leu Arg Lys Thr Val Val Trp Ala His Glu
785 790 795 800

Lys Tyr Gly Ile Glu Ser Phe Ala Leu Ile His Asp Ser Phe Gly Thr
805 810 815

Ile Pro Ala Asp Ala Ala Asn Leu Phe Lys Ala Val Arg Glu Thr Met
820 825 830

Val Asp Thr Tyr Glu Ser Cys Asp Val Leu Ala Asp Phe Tyr Asp Gln
835 840 845

Phe Ala Asp Gln Leu His Glu Ser Gln Leu Asp Lys Met Pro Ala Leu
850 855 860

Pro Ala Lys Gly Asn Leu Asn Leu Arg Asp Ile Leu Glu Ser Asp Phe
865 870 875 880

Ala Phe Ala

<210> SEQ ID NO 47
<211> LENGTH: 2652
<212> TYPE: DNA
<213> ORGANISM: T7 bacteriophage

<400> SEQUENCE: 47
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720

```
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggccg tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaaggta ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctatgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652
```

<210> SEQ ID NO 48
<211> LENGTH: 883
<212> TYPE: PRT
<213> ORGANISM: T7 bacteriophage

<400> SEQUENCE: 48

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
```

-continued

```
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445
```

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

-continued

Pro Ala Lys Gly Asn Leu Asn Leu Arg Asp Ile Leu Glu Ser Asp Phe
865 870 875 880

Ala Phe Ala

<210> SEQ ID NO 49
<211> LENGTH: 2652
<212> TYPE: DNA
<213> ORGANISM: T7 bacteriophage

<400> SEQUENCE: 49
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggccg tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagcgttcag tcatgacgct ggcttacggg 1920
tccaaagagt tcggcttccg tcaacaagtg ctggaagata ccattcagcc agctattgat 1980

-continued tccggcaagg gtctgatgtt cactcagccg aatcaggctg ctggatacat ggctaagctg 2040
atttgggaat ctgtgagcgt gacggtggta gctgcggttg aagcaatgaa cgggcttaag 2100
tctgctgcta agctgctggc tgctgaggtc aaagataaga agactggaga gattcttcgc 2160
aagcgttgcg ctgtgcattg ggtaactcct gatggtttcc ctatgtggca ggaatacaag 2220
aagcctattc agacgcgctt gaacctgatg ttcctcggtc agttccgctt acagcctacc 2280
attaacacca acaaagatag cgagattgat gcacacaaac aggagtctgg tatcgctcct 2340
aactttgtac acagccaaga cggtagccac cttcgtaaga ctgtagtgtg ggcacacgag 2400
aagtacggaa tcgaatcttt tgcactgatt cacgactcct tcggtaccat tccggctgac 2460
gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 50
<211> LENGTH: 883
<212> TYPE: PRT
<213> ORGANISM: T7 bacteriophage

<400> SEQUENCE: 50

Met Asn Thr Ile Asn Ile Ala Lys Asn Asp Phe Ser Asp Ile Glu Leu
1 5 10 15

Ala Ala Ile Pro Phe Asn Thr Leu Ala Asp His Tyr Gly Glu Arg Leu
20 25 30

Ala Arg Glu Gln Leu Ala Leu Glu His Glu Ser Tyr Glu Met Gly Glu
35 40 45

Ala Arg Phe Arg Lys Met Phe Glu Arg Gln Leu Lys Ala Gly Glu Val
50 55 60

Ala Asp Asn Ala Ala Ala Lys Pro Leu Ile Thr Thr Leu Leu Pro Lys
65 70 75 80

Met Ile Ala Arg Ile Asn Asp Trp Phe Glu Glu Val Lys Ala Lys Arg
85 90 95

Gly Lys Arg Pro Thr Ala Phe Gln Phe Leu Gln Glu Ile Lys Pro Glu
100 105 110

Ala Val Ala Tyr Ile Thr Ile Lys Thr Thr Leu Ala Cys Leu Thr Ser
115 120 125

Ala Asp Asn Thr Thr Val Gln Ala Val Ala Ser Ala Ile Gly Arg Ala
130 135 140

Ile Glu Asp Glu Ala Arg Phe Gly Arg Ile Arg Asp Leu Glu Ala Lys
145 150 155 160

His Phe Lys Lys Asn Val Glu Glu Gln Leu Asn Lys Arg Val Gly His
165 170 175

Val Tyr Lys Lys Ala Phe Met Gln Val Val Glu Ala Asp Met Leu Ser
180 185 190

Lys Gly Leu Leu Gly Gly Glu Ala Trp Ser Ser Trp His Lys Glu Asp
195 200 205

Ser Ile His Val Gly Val Arg Cys Ile Glu Met Leu Ile Glu Ser Thr
210 215 220

Gly Met Val Ser Leu His Arg Gln Asn Ala Gly Val Val Gly Gln Asp
225 230 235 240

Ser Glu Thr Ile Glu Leu Ala Pro Glu Tyr Ala Glu Ala Ile Ala Thr
245 250 255

```
Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670
```

-continued

```
Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 51
<211> LENGTH: 2652
<212> TYPE: DNA
<213> ORGANISM: T7 bacteriophage

<400> SEQUENCE: 51

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac gcatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780

ctggctggca tctctccgat gttccaacct tgcgtagttc ctcctaagcc gtggactggc     840

attactggtg gtggctattg ggctaacggt cgtcgtcctc tggcgctggt gcgtactcac     900
```

```
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaaggta ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctatgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                        2652
```

<210> SEQ ID NO 52
<211> LENGTH: 883
<212> TYPE: PRT
<213> ORGANISM: T7 bacteriophage

<400> SEQUENCE: 52

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60
```

-continued

```
Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480
```

-continued

```
Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 53

<211> LENGTH: 2652
<212> TYPE: DNA
<213> ORGANISM: T7 bacteriophage

<400> SEQUENCE: 53

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac acatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggccg tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaaggta ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
```

-continued

```
aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652


<210> SEQ ID NO 54
<211> LENGTH: 883
<212> TYPE: PRT
<213> ORGANISM: T7 bacteriophage

<400> SEQUENCE: 54

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285
```

-continued

```
Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
```

```
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 55
<211> LENGTH: 2652
<212> TYPE: DNA
<213> ORGANISM: T7 bacteriophage

<400> SEQUENCE: 55

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac acatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780

ctggctggca tctctccgat gttccaacct tgcgtagttc ctcctaagcc gtggactggc     840

attactggtg gtggctattg ggctaacggt cgtcgtcctc tggcgctggt gcgtactcac     900

agtaagaaag cactgatgcg ctacgaagac gtttacatgc ctgaggtgta caaagcgatt     960

aacattgcgc aaaacaccgc atggaaaatc aacaagaaag tcctagcggt cgccaacgta    1020

atcaccaagt ggaagcattg tccggtcgag gacatccctg cgattgagcg tgaagaactc    1080

ccgatgaaac cggaagacat cgacatgaat cctgaggctc tcaccgcgtg gaaacgtgct    1140
```

```
gccgctgctg tgtaccgcaa ggacaaggct cgcaagtctc gccgtatcag ccttgagttc   1200

atgcttgagc aagccaataa gtttgctaac cataaggccg tctggttccc ttacaacatg   1260

gactggcgcg gtcgtgttta cgctgtgtca atgttcaacc cgcaaggtaa cgatatgacc   1320

aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

<210> SEQ ID NO 56
<211> LENGTH: 883
<212> TYPE: PRT
<213> ORGANISM: T7 bacteriophage

<400> SEQUENCE: 56

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95
```

```
Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
```

```
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 57
<211> LENGTH: 2652
<212> TYPE: DNA
<213> ORGANISM: T7 bacteriophage

<400> SEQUENCE: 57

atgaacacga ttaacatcgc taagaacgac ttctctgaca tcgaactggc tgctatcccg      60
```

-continued ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac acatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggccg tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagcgttcag tcatgacgct ggcttacggg 1920
tccaaagagt tcggcttccg tcaacaagtg ctggaagata ccattcagcc agctattgat 1980
tccggcaagg gtctgatgtt cactcagccg aatcaggctg ctggatacat ggctaagctg 2040
atttgggaat ctgtgagcgt gacggtggta gctgcggttg aagcaatgaa cgggcttaag 2100
tctgctgcta agctgctggc tgctgaggtc aaagataaga agactggaga gattcttcgc 2160
aagcgttgcg ctgtgcattg ggtaactcct gatggtttcc ctatgtggca ggaatacaag 2220
aagcctattc agacgcgctt gaacctgatg ttcctcggtc agttccgctt acagcctacc 2280
attaacacca acaaagatag cgagattgat gcacacaaac aggagtctgg tatcgctcct 2340
aactttgtac acagccaaga cggtagccac cttcgtaaga ctgtagtgtg ggcacacgag 2400

-continued aagtacggaa tcgaatcttt tgcactgatt cacgactcct tcggtaccat tccggctgac 2460
gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 58
<211> LENGTH: 883
<212> TYPE: PRT
<213> ORGANISM: T7 bacteriophage

<400> SEQUENCE: 58

Met Asn Thr Ile Asn Ile Ala Lys Asn Asp Phe Ser Asp Ile Glu Leu
1 5 10 15

Ala Ala Ile Pro Phe Asn Thr Leu Ala Asp His Tyr Gly Glu Arg Leu
20 25 30

Ala Arg Glu Gln Leu Ala Leu Glu His Glu Ser Tyr Glu Met Gly Glu
35 40 45

Ala Arg Phe Arg Lys Met Phe Glu Arg Gln Leu Lys Ala Gly Glu Val
50 55 60

Ala Asp Asn Ala Ala Ala Lys Pro Leu Ile Thr Thr Leu Leu Pro Lys
65 70 75 80

Met Ile Ala His Ile Asn Asp Trp Phe Glu Glu Val Lys Ala Lys Arg
85 90 95

Gly Lys Arg Pro Thr Ala Phe Gln Phe Leu Gln Glu Ile Lys Pro Glu
100 105 110

Ala Val Ala Tyr Ile Thr Ile Lys Thr Thr Leu Ala Cys Leu Thr Ser
115 120 125

Ala Asp Asn Thr Thr Val Gln Ala Val Ala Ser Ala Ile Gly Arg Ala
130 135 140

Ile Glu Asp Glu Ala Arg Phe Gly Arg Ile Arg Asp Leu Glu Ala Lys
145 150 155 160

His Phe Lys Lys Asn Val Glu Glu Gln Leu Asn Lys Arg Val Gly His
165 170 175

Val Tyr Lys Lys Ala Phe Met Gln Val Val Glu Ala Asp Met Leu Ser
180 185 190

Lys Gly Leu Leu Gly Gly Glu Ala Trp Ser Ser Trp His Lys Glu Asp
195 200 205

Ser Ile His Val Gly Val Arg Cys Ile Glu Met Leu Ile Glu Ser Thr
210 215 220

Gly Met Val Ser Leu His Arg Gln Asn Ala Gly Val Val Gly Gln Asp
225 230 235 240

Ser Glu Thr Ile Glu Leu Ala Pro Glu Tyr Ala Glu Ala Ile Ala Thr
245 250 255

Arg Ala Gly Ala Leu Ala Gly Ile Ser Pro Met Phe Gln Pro Cys Val
260 265 270

Val Pro Pro Lys Pro Trp Thr Gly Ile Thr Gly Gly Gly Tyr Trp Ala
275 280 285

Asn Gly Arg Arg Pro Leu Ala Leu Val Arg Thr His Ser Lys Lys Ala
290 295 300

Leu Met Arg Tyr Glu Asp Val Tyr Met Pro Glu Val Tyr Lys Ala Ile
305 310 315 320

Asn Ile Ala Gln Asn Thr Ala Trp Lys Ile Asn Lys Lys Val Leu Ala

-continued

```
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750
```

```
Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 59
<211> LENGTH: 2652
<212> TYPE: DNA
<213> ORGANISM: T7 bacteriophage

<400> SEQUENCE: 59

atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240

atgattgcac acatcaacga ctggtttgag gaagtgaaag ctaagcgcgg caagcgcccg     300

acagccttcc agttcctgca agaaatcaag ccggaagccg tagcgtacat caccattaag     360

accactctgg cttgcctaac cagtgctgac aatacaaccg ttcaggctgt agcaagcgca     420

atcggtcggg ccattgagga cgaggctcgc ttcggtcgta tccgtgacct tgaagctaag     480

cacttcaaga aaaacgttga ggaacaactc aacaagcgcg tagggcacgt ctacaagaaa     540

gcatttatgc aagttgtcga ggctgacatg ctctctaagg gtctactcgg tggcgaggcg     600

tggtcttcgt ggcataagga agactctatt catgtaggag tacgctgcat cgagatgctc     660

attgagtcaa ccggaatggt tagcttacac cgccaaaatg ctggcgtagt aggtcaagac     720

tctgagacta tcgaactcgc acctgaatac gctgaggcta tcgcaacccg tgcaggtgcg     780

ctggctggca tctctccgat gttccaacct tgcgtagttc ctcctaagcc gtggactggc     840

attactggtg gtggctattg ggctaacggt cgtcgtcctc tggcgctggt gcgtactcac     900

agtaagaaag cactgatgcg ctacgaagac gtttacatgc ctgaggtgta caaagcgatt     960

aacattgcgc aaaacaccgc atggaaaatc aacaagaaag tcctagcggt cgccaacgta    1020

atcaccaagt ggaagcattg tccggtcgag gacatccctg cgattgagcg tgaagaactc    1080

ccgatgaaac cggaagacat cgacatgaat cctgaggctc tcaccgcgtg gaaacgtgct    1140

gccgctgctg tgtaccgcaa ggacaaggct cgcaagtctc gccgtatcag ccttgagttc    1200

atgcttgagc aagccaataa gtttgctaac cataaggcca tctggttccc ttacaacatg    1260

gactggcgcg gtcgtgttta cgctgtgtca atgttcaacc cgcaaggtaa cgatatgacc    1320
```

-continued

```
aaaggactgc ttacgctggc gaaaggtaaa ccaatcggta aggaaggtta ctactggctg   1380

aaaatccacg gtgcaaactg tgcgggtgtc gataaggttc cgttccctga gcgcatcaag   1440

ttcattgagg aaaaccacga gaacatcatg gcttgcgcta agtctccact ggagaacact   1500

tggtgggctg agcaagattc tccgttctgc ttccttgcgt tctgctttga gtacgctggg   1560

gtacagcacc acggcctgag ctataactgc tcccttccgc tggcgtttga cgggtcttgc   1620

tctggcatcc agcacttctc cgcgatgctc cgagatgagg taggtggtcg cgcggttaac   1680

ttgcttccta gtgaaaccgt tcaggacatc tacgggattg ttgctaagaa agtcaacgag   1740

attctacaag cagacgcaat caatgggacc gataacgaag tagttaccgt gaccgatgag   1800

aacactggtg aaatctctga gaaagtcaag ctgggcacta aggcactggc tggtcaatgg   1860

ctggcttacg gtgttactcg cagtgtgact aagcgttcag tcatgacgct ggcttacggg   1920

tccaaagagt tcggcttccg tcaacaagtg ctggaaggta ccattcagcc agctattgat   1980

tccggcaagg gtctgatgtt cactcagccg aatcaggctg ctggatacat ggctaagctg   2040

atttgggaat ctgtgagcgt gacggtggta gctgcggttg aagcaatgaa cgggcttaag   2100

tctgctgcta agctgctggc tgctgaggtc aaagataaga agactggaga gattcttcgc   2160

aagcgttgcg ctgtgcattg ggtaactcct gatggtttcc ctatgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtaccat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                       2652
```

```
<210> SEQ ID NO 60
<211> LENGTH: 883
<212> TYPE: PRT
<213> ORGANISM: T7 bacteriophage

<400> SEQUENCE: 60

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala His Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
```

```
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560
```

```
Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 61
<211> LENGTH: 2652
<212> TYPE: DNA
<213> ORGANISM: T7 bacteriophage

<400> SEQUENCE: 61

```
atgaacacga ttaacatcgc taagaacgac ttctctgaca tcgaactggc tgctatcccg      60

ttcaacactc tggctgacca ttacggtgag cgtttagctc gcgaacagtt ggcccttgag     120

catgagtctt acgagatggg tgaagcacgc ttccgcaaga tgtttgagcg tcaacttaaa     180

gctggtgagg ttgcggataa cgctgccgcc aagcctctca tcactaccct actccctaag     240
```

-continued

```
atgattgcac acatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggccg tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaaggta ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa cgggcttaag   2100
tctgctgcta agctgctggc tgctgaggtc aaagataaga agactggaga gattcttcgc   2160
aagcgttgcg ctgtgcattg ggtaactcct gatggtttcc ctatgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
```

gcgttcgcgt aa 2652

<210> SEQ ID NO 62
<211> LENGTH: 883
<212> TYPE: PRT
<213> ORGANISM: T7 bacteriophage

<400> SEQUENCE: 62

Met Asn Thr Ile Asn Ile Ala Lys Asn Asp Phe Ser Asp Ile Glu Leu
1 5 10 15

Ala Ala Ile Pro Phe Asn Thr Leu Ala Asp His Tyr Gly Glu Arg Leu
20 25 30

Ala Arg Glu Gln Leu Ala Leu Glu His Glu Ser Tyr Glu Met Gly Glu
35 40 45

Ala Arg Phe Arg Lys Met Phe Glu Arg Gln Leu Lys Ala Gly Glu Val
50 55 60

Ala Asp Asn Ala Ala Ala Lys Pro Leu Ile Thr Thr Leu Leu Pro Lys
65 70 75 80

Met Ile Ala His Ile Asn Asp Trp Phe Glu Glu Val Lys Ala Lys Arg
85 90 95

Gly Lys Arg Pro Thr Ala Phe Gln Phe Leu Gln Glu Ile Lys Pro Glu
100 105 110

Ala Val Ala Tyr Ile Thr Ile Lys Thr Thr Leu Ala Cys Leu Thr Ser
115 120 125

Ala Asp Asn Thr Thr Val Gln Ala Val Ala Ser Ala Ile Gly Arg Ala
130 135 140

Ile Glu Asp Glu Ala Arg Phe Gly Arg Ile Arg Asp Leu Glu Ala Lys
145 150 155 160

His Phe Lys Lys Asn Val Glu Glu Gln Leu Asn Lys Arg Val Gly His
165 170 175

Val Tyr Lys Lys Ala Phe Met Gln Val Val Glu Ala Asp Met Leu Ser
180 185 190

Lys Gly Leu Leu Gly Gly Glu Ala Trp Ser Ser Trp His Lys Glu Asp
195 200 205

Ser Ile His Val Gly Val Arg Cys Ile Glu Met Leu Ile Glu Ser Thr
210 215 220

Gly Met Val Ser Leu His Arg Gln Asn Ala Gly Val Val Gly Gln Asp
225 230 235 240

Ser Glu Thr Ile Glu Leu Ala Pro Glu Tyr Ala Glu Ala Ile Ala Thr
245 250 255

Arg Ala Gly Ala Leu Ala Gly Ile Ser Pro Met Phe Gln Pro Cys Val
260 265 270

Val Pro Pro Lys Pro Trp Thr Gly Ile Thr Gly Gly Gly Tyr Trp Ala
275 280 285

Asn Gly Arg Arg Pro Leu Ala Leu Val Arg Thr His Ser Lys Lys Ala
290 295 300

Leu Met Arg Tyr Glu Asp Val Tyr Met Pro Glu Val Tyr Lys Ala Ile
305 310 315 320

Asn Ile Ala Gln Asn Thr Ala Trp Lys Ile Asn Lys Lys Val Leu Ala
325 330 335

Val Ala Asn Val Ile Thr Lys Trp Lys His Cys Pro Val Glu Asp Ile
340 345 350

Pro Ala Ile Glu Arg Glu Glu Leu Pro Met Lys Pro Glu Asp Ile Asp
355 360 365

```
Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Val Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Gly Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Gly Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Met Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780
```

-continued

```
Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 63
<211> LENGTH: 3075
<212> TYPE: DNA
<213> ORGANISM: Escherichia coli

<400> SEQUENCE: 63

atgaccatga ttacggattc actggccgtc gttttacaac gtcgtgactg ggaaaaccct     60

ggcgttaccc aacttaatcg ccttgcagca catccccctt tcgccagctg gcgtaatagc    120

gaagaggccc gcaccgatcg cccttcccaa cagttgcgca gcctgaatgg cgaatggcgc    180

tttgcctggt ttccggcacc agaagcggtg ccggaaagct ggctggagtg cgatcttcct    240

gaggccgata ctgtcgtcgt cccctcaaac tggcagatgc acggttacga tgcgcccatc    300

tacaccaacg tgacctatcc cattacggtc aatccgccgt ttgttcccac ggagaatccg    360

acgggttgtt actcgctcac atttaatgtt gatgaaagct ggctacagga aggccagacg    420

cgaattattt ttgatggcgt taactcggcg tttcatctgt ggtgcaacgg gcgctgggtc    480

ggttacggcc aggacagtcg tttgccgtct gaatttgacc tgagcgcatt tttacgcgcc    540

ggagaaaacc gcctcgcggt gatggtgctg cgctggagtg acggcagtta tctggaagat    600

caggatatgt ggcggatgag cggcattttc cgtgacgtct cgttgctgca taaaccgact    660

acacaaatca gcgatttcca tgttgccact cgctttaatg atgatttcag ccgcgctgta    720

ctggaggctg aagttcagat gtgcggcgag ttgcgtgact acctacgggt aacagtttct    780

ttatggcagg gtgaaacgca ggtcgccagc ggcaccgcgc ctttcggcgg tgaaattatc    840

gatgagcgtg gtggttatgc cgatcgcgtc acactacgtc tgaacgtcga aaacccgaaa    900

ctgtggagcg ccgaaatccc gaatctctat cgtgcggtgg ttgaactgca caccgccgac    960

ggcacgctga ttgaagcaga agcctgcgat gtcggtttcc gcgaggtgcg gattgaaaat   1020

ggtctgctgc tgctgaacgg caagccgttg ctgattcgag gcgttaaccg tcacgagcat   1080

catcctctgc atggtcaggt catggatgag cagacgatgg tgcaggatat cctgctgatg   1140

aagcagaaca actttaacgc cgtgcgctgt tcgcattatc cgaaccatcc gctgtggtac   1200

acgctgtgcg accgctacgg cctgtatgtg gtggatgaag ccaatattga aacccacggc   1260

atggtgccaa tgaatcgtct gaccgatgat ccgcgctggc taccggcgat gagcgaacgc   1320

gtaacgcgaa tggtgcagcg cgatcgtaat cacccgagtg tgatcatctg gtcgctgggg   1380

aatgaatcag gccacggcgc taatcacgac gcgctgtatc gctggatcaa atctgtcgat   1440

ccttcccgcc cggtgcagta tgaaggcggc ggagccgaca ccacggccac cgatattatt   1500

tgcccgatgt acgcgcgcgt ggatgaagac cagcccttcc cggctgtgcc gaaatggtcc   1560
```

```
atcaaaaaat ggctttcgct acctggagag acgcgcccgc tgatcctttg cgaatacgcc   1620
cacgcgatgg gtaacagtct tggcggtttc gctaaatact ggcaggcgtt tcgtcagtat   1680
ccccgtttac agggcggctt cgtctgggac tgggtggatc agtcgctgat taaatatgat   1740
gaaaacggca acccgtggtc ggcttacggc ggtgattttg gcgatacgcc gaacgatcgc   1800
cagttctgta tgaacggtct ggtctttgcc gaccgcacgc cgcatccagc gctgacggaa   1860
gcaaaacacc agcagcagtt tttccagttc cgtttatccg ggcaaaccat cgaagtgacc   1920
agcgaatacc tgttccgtca tagcgataac gagctcctgc actggatggt ggcgctggat   1980
ggtaagccgc tggcaagcgg tgaagtgcct ctggatgtcg ctccacaagg taaacagttg   2040
attgaactgc ctgaactacc gcagccggag agcgccgggc aactctggct cacagtacgc   2100
gtagtgcaac cgaacgcgac cgcatggtca gaagccgggc acatcagcgc ctggcagcag   2160
tggcgtctgg cggaaaacct cagtgtgacg ctccccgccg cgtcccacgc catcccgcat   2220
ctgaccacca gcgaaatgga tttttgcatc gagctgggta ataagcgttg gcaatttaac   2280
cgccagtcag gctttctttc acagatgtgg attggcgata aaaaacaact gctgacgccg   2340
ctgcgcgatc agttcacccg tgcaccgctg gataacgaca ttggcgtaag tgaagcgacc   2400
cgcattgacc ctaacgcctg ggtcgaacgc tggaaggcgg cgggccatta ccaggccgaa   2460
gcagcgttgt tgcagtgcac ggcagataca cttgctgatg cggtgctgat tacgaccgct   2520
cacgcgtggc agcatcaggg gaaaacctta tttatcagcc ggaaaaccta ccggattgat   2580
ggtagtggtc aaatggcgat taccgttgat gttgaagtgg cgagcgatac accgcatccg   2640
gcgcggattg gcctgaactg ccagctggcg caggtagcag agcgggtaaa ctggctcgga   2700
ttagggccgc aagaaaacta tcccgaccgc cttactgccg cctgttttga ccgctgggat   2760
ctgccattgt cagacatgta taccccgtac gtcttcccga gcgaaaacgg tctgcgctgc   2820
gggacgcgcg aattgaatta tggcccacac cagtggcgcg gcgacttcca gttcaacatc   2880
agccgctaca gtcaacagca actgatggaa accagccatc gccatctgct gcacgcggaa   2940
gaaggcacat ggctgaatat cgacggtttc catatgggga ttggtggcga cgactcctgg   3000
agcccgtcag tatcggcgga attccagctg agcgccggtc gctaccatta ccagttggtc   3060
tggtgtcaaa aataa                                                    3075
```

<210> SEQ ID NO 64
<211> LENGTH: 1024
<212> TYPE: PRT
<213> ORGANISM: Escherichia coli

<400> SEQUENCE: 64

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95
```

-continued

```
Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
    370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
        435                 440                 445

Arg Asn His Pro Ser Val Ile Ile Trp Ser Leu Gly Asn Glu Ser Gly
    450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
```

```
        515                 520                 525

Gly Glu Thr Arg Pro Leu Ile Leu Cys Glu Tyr Ala His Ala Met Gly
    530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
                565                 570                 575

Ile Lys Tyr Asp Glu Asn Gly Asn Pro Trp Ser Ala Tyr Gly Gly Asp
            580                 585                 590

Phe Gly Asp Thr Pro Asn Asp Arg Gln Phe Cys Met Asn Gly Leu Val
        595                 600                 605

Phe Ala Asp Arg Thr Pro His Pro Ala Leu Thr Glu Ala Lys His Gln
    610                 615                 620

Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
                645                 650                 655

Val Ala Leu Asp Gly Lys Pro Leu Ala Ser Gly Glu Val Pro Leu Asp
            660                 665                 670

Val Ala Pro Gln Gly Lys Gln Leu Ile Glu Leu Pro Glu Leu Pro Gln
        675                 680                 685

Pro Glu Ser Ala Gly Gln Leu Trp Leu Thr Val Arg Val Val Gln Pro
    690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
                725                 730                 735

Ala Ile Pro His Leu Thr Thr Ser Glu Met Asp Phe Cys Ile Glu Leu
            740                 745                 750

Gly Asn Lys Arg Trp Gln Phe Asn Arg Gln Ser Gly Phe Leu Ser Gln
        755                 760                 765

Met Trp Ile Gly Asp Lys Lys Gln Leu Leu Thr Pro Leu Arg Asp Gln
    770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
            820                 825                 830

Asp Ala Val Leu Ile Thr Thr Ala His Ala Trp Gln His Gln Gly Lys
        835                 840                 845

Thr Leu Phe Ile Ser Arg Lys Thr Tyr Arg Ile Asp Gly Ser Gly Gln
    850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
        915                 920                 925

Pro Tyr Val Phe Pro Ser Glu Asn Gly Leu Arg Cys Gly Thr Arg Glu
    930                 935                 940
```

```
Leu Asn Tyr Gly Pro His Gln Trp Arg Gly Asp Phe Gln Phe Asn Ile
945                 950                 955                 960

Ser Arg Tyr Ser Gln Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp  Ser Pro Ser Val Ser  Ala Glu Phe
        995                 1000                 1005

Gln Leu  Ser Ala Gly Arg Tyr  His Tyr Gln Leu Val  Trp Cys Gln
    1010                 1015                 1020

Lys
```

<210> SEQ ID NO 65
<211> LENGTH: 3075
<212> TYPE: DNA
<213> ORGANISM: Escherichia coli

<400> SEQUENCE: 65

```
atgactatga ttacagattc actggccgtc gttttacaac gtcgtgactg ggaaaaccct     60

ggcgttaccc aacttaatcg ccttgcagca catccccctt tcgccagctg gcgtaatagc    120

gaagaggccc gcaccaatcg cccttcccag cagttgcgca gcctgaatgg tgagtggcaa    180

tttgtctggt ttccggcacc agaagcggtt ccggaaagct ggctggagtg cgatcttcct    240

gacgccgata ctgtcgtcgt cccctcaaac tggcagatgc acggttacga cgcgcccatc    300

tacaccaacg tgacatatcc cattacggtc aatccgccat ttgttcccac ggagaatccg    360

acgggttgtt actcgctcac atttaatgtt gatgaaagct ggctacagga aggccagacg    420

cgaattattt ttgatggcgt taactcggcg tttcatctgt ggtgcaacgg gcgctgggtc    480

ggttacggcc aggacagtcg tttgctgtct gaatttgacc tgagcgcatt tttacgcgcc    540

ggagaaaacc gcctcgcggt gatggtgctg cgctggagtg acggcagtta tctggaagat    600

caggatatgt ggcggatgag cggcattttc cgtgacgtct cgttgctgca caaaccgacc    660

acacaaatca gcgatttcca tgttgccact ctctttaatg atgattttag ccgcgcggta    720

ctggaggcag aagttcagat gtacggcgag ctgcgcgatg agctgcgggt gacggtttct    780

ttgtggcagg gtgaaacgca ggtcgccagc ggcaccgcgc ctttcggcgg tgaaattatc    840

gatgagcgtg gcggttatgc cgatcgcgtc acactaggtc tgaacgtcga aaacccgaaa    900

ctgtggagcg ccgaaatccc gaatatctat cgtgcggtgg ttgaactgca caccgccgac    960

ggcacgctga ttgaagcaga agcctgcgat gtcggtttcc gcgaggtgcg gattgaaaat   1020

ggtctgctgc tgctgaacgg caagccgttg ctgattcgcg gcgttaaccg tcacgagcat   1080

catcctctgc atggtcaggt catggatgag cagacgatgg tgcaggatat cctgctaatg   1140

aagcagaaca actttaacgc cgtgcgctgt tcgcattatc cgaaccatcc gctgtggtac   1200

accctgtgcg accgctacgg cctgtatgtg gtggatgaag ccaatattga aacccacggc   1260

atggtgccaa tgaatcgtct gaccgatgat ccgcgctggt taccggccat gagcgaacga   1320

gtaacacgaa tggtacagcg cgatcgtaat cacccgagtg tgatcatctg gtcgctgggg   1380

aatgagtcag gccacggcgc taatcacgac gcactctatc gctggattaa atctgtcgat   1440

ccatcccgcc cggtgcagta tgaaggcggc ggagccgaca cctccgcaac cgatattatt   1500

tgcccgatgt acgcgcgcgt ggatgaagac cagcccttcc cggctgtgcc gaaatggtcc   1560

atcaaaaaat ggctttcgct gcctggagaa atgcgcccac tgatcctttg cgaatacgcc   1620
```

```
cacgcgatgg gtaacagtct tggcggcttc gctaaatact ggcaggcgtt tcgtcagtac   1680
ccccgtttac agggcggctt cgtctgggac ttggtggatc agtcgctgat taaatatgat   1740
gaaaatggca atccgtggtc ggcttacggc ggtgattttg gcgatacgcc gaatgatcgc   1800
cagttctgca tgaacggtct ggtctttgcc gaccgcacgc cgcatccggc gctgacggaa   1860
gcaaaacacc agcagcagtt tttccagttc cgtttatccg ggcgaaccat cgaagtgacc   1920
agcgaatacc tgttccgtca tagcgataac gagctcctgc actggacggt ggcgctggat   1980
ggtaagccgc tggcaagcgg tgaagtgcct ctggatgtcg ctccgcaagg taaacaggta   2040
attgaattgc ctgaactacc gcgactggag agcaccgggc aactctggct aacggtacac   2100
gtagtgcaac cgaacgcgac cgcatggtca gaagccggac acatcagcgc ctggcagcag   2160
tggcgtctgg cggaaaacct cagcgtgaca ctcccctccg cgccccacgc catcccgcaa   2220
ctgaccacca gcgaaacgga tttttgcatc gagctggata ataagcgttg gcaatttaac   2280
cgccagtcag gctttctttc acagatgtgg attggcgata aaaaacaact gctgacgccg   2340
ctgcgcgatc agttcacccg cgcaccgctg gataacgaca ttggcgtaag tgaagcgacc   2400
cgcattgacc ctaacgcctg ggtcgaacgc tggaaggctg cgggccatta ccaggcagaa   2460
gcggcgttgt tgcagtgcac ggcagataca cttgccgacg cggtgctgat taccactgtc   2520
cacgcatggc agcatcaggg aaaaacctta tttattagcc ggaaaaccta ccggattgat   2580
ggtagtggtc aaatggcgat taccgttgat gttgaagtag cgagcgatac accgcatccg   2640
gcacggattg gcctgacctg ccagctggcg caggtagcag agcgggtaaa ctggctcgga   2700
ttagggccgc aagaaaacta tcccgaccgc cttactgccg cctgttttga ccgctgggat   2760
ctgccattgt cagacatgta taccccgtac gtcttcccga gcgaaaacgg tctgcgctgc   2820
gggacgcgcg aattgaatta tggcccacac cagtggcgcg gcgacttcca gttcaacatc   2880
agccgctaca gccaacaaca actgatggaa accagccatc gccatctgct gcacgcggaa   2940
gaaggaacat ggctgaatat cgacggtttc catatgggga ttggtggcga cgactcctgg   3000
agcccgtcag tatcggcgga attccagctg agcgccggtc gctaccatta ccagttggtc   3060
tggtgtcaaa aataa                                                    3075
```

<210> SEQ ID NO 66
<211> LENGTH: 1024
<212> TYPE: PRT
<213> ORGANISM: Escherichia coli

<400> SEQUENCE: 66

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asn Arg Pro
        35                  40                  45

Ser Gln Gln Leu Arg Ser Leu Asn Gly Glu Trp Gln Phe Val Trp Phe
    50                  55                  60

Pro Ala Pro Glu Ala Val Pro Glu Ser Trp Leu Glu Cys Asp Leu Pro
65                  70                  75                  80

Asp Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110
```

-continued

```
Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Leu Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Leu Phe Asn Asp Asp Phe Ser Arg Ala Val
225                 230                 235                 240

Leu Glu Ala Glu Val Gln Met Tyr Gly Glu Leu Arg Asp Glu Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Gly Leu Asn Val Glu Asn Pro Lys Leu Trp Ser Ala
    290                 295                 300

Glu Ile Pro Asn Ile Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
    370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
        435                 440                 445

Arg Asn His Pro Ser Val Ile Ile Trp Ser Leu Gly Asn Glu Ser Gly
    450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Ser Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
        515                 520                 525
```

-continued

```
Gly Glu Met Arg Pro Leu Ile Leu Cys Glu Tyr Ala His Ala Met Gly
    530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Leu Val Asp Gln Ser Leu
                565                 570                 575

Ile Lys Tyr Asp Glu Asn Gly Asn Pro Trp Ser Ala Tyr Gly Gly Asp
            580                 585                 590

Phe Gly Asp Thr Pro Asn Asp Arg Gln Phe Cys Met Asn Gly Leu Val
        595                 600                 605

Phe Ala Asp Arg Thr Pro His Pro Ala Leu Thr Glu Ala Lys His Gln
    610                 615                 620

Gln Gln Phe Phe Gln Phe Arg Leu Ser Gly Arg Thr Ile Glu Val Thr
625                 630                 635                 640

Ser Glu Tyr Leu Phe Arg His Ser Asp Asn Glu Leu Leu His Trp Thr
                645                 650                 655

Val Ala Leu Asp Gly Lys Pro Leu Ala Ser Gly Glu Val Pro Leu Asp
            660                 665                 670

Val Ala Pro Gln Gly Lys Gln Val Ile Glu Leu Pro Glu Leu Pro Arg
        675                 680                 685

Leu Glu Ser Thr Gly Gln Leu Trp Leu Thr Val His Val Val Gln Pro
    690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ser Ala Pro His
                725                 730                 735

Ala Ile Pro Gln Leu Thr Thr Ser Glu Thr Asp Phe Cys Ile Glu Leu
            740                 745                 750

Asp Asn Lys Arg Trp Gln Phe Asn Arg Gln Ser Gly Phe Leu Ser Gln
        755                 760                 765

Met Trp Ile Gly Asp Lys Lys Gln Leu Leu Thr Pro Leu Arg Asp Gln
    770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
            820                 825                 830

Asp Ala Val Leu Ile Thr Thr Val His Ala Trp Gln His Gln Gly Lys
        835                 840                 845

Thr Leu Phe Ile Ser Arg Lys Thr Tyr Arg Ile Asp Gly Ser Gly Gln
    850                 855                 860

Met Ala Ile Thr Val Asp Val Glu Val Ala Ser Asp Thr Pro His Pro
865                 870                 875                 880

Ala Arg Ile Gly Leu Thr Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
        915                 920                 925

Pro Tyr Val Phe Pro Ser Glu Asn Gly Leu Arg Cys Gly Thr Arg Glu
    930                 935                 940

Leu Asn Tyr Gly Pro His Gln Trp Arg Gly Asp Phe Gln Phe Asn Ile
```

-continued

```
945                 950                 955                 960

Ser Arg Tyr Ser Gln Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp  Ser Pro Ser Val Ser  Ala Glu Phe
        995                 1000                1005

Gln Leu  Ser Ala Gly Arg Tyr  His Tyr Gln Leu Val  Trp Cys Gln
    1010                 1015                1020

Lys
```

<210> SEQ ID NO 67
<211> LENGTH: 1254
<212> TYPE: DNA
<213> ORGANISM: Escherichia coli

<400> SEQUENCE: 67

```
atgtactatt taaaaaacac aaacttttgg atgttcggtt tattcttttt cttttacttt     60

tttatcatgg gagcctactt cccgtttttc ccgatttggc tacatgacat caaccatatc    120

agcaaaagtg atacgggtat tatttttgcc gctatttctc tgttctcgct attattccaa    180

ccgctgtttg gtctgctttc tgacaaactc gggctgcgca aatacctgct gtggattatt    240

accggcatgt tagtgatgtt tgcgccgttc tttattttta tcttcgggcc actgttacaa    300

tacaacattt tagtaggatc gattgttggt ggtatttatc taggcttttg ttttaacgcc    360

ggtgcgccag cagtagaggc atttattgag aaagtcagcc gtcgcagtaa tttcgaattt    420

ggtcgcgcgc ggatgtttgg ctgtgttggc tgggcgctgt gtgcctcgat tgtcggcatc    480

atgttcacca tcaataatca gtttgttttc tggctgggct ctggctgtgc actcatcctc    540

gccgttttac tctttttcgc caaaacggat gcgccctctt ctgccacggt tgccaatgcg    600

gtaggtgcca accattcggc atttagcctt aagctggcac tggaactgtt cagacagcca    660

aaactgtggt ttttgtcact gtatgttatt ggcgtttcct gcacctacga tgtttttgac    720

caacagtttg ctaatttctt tacttcgttc tttgctaccg gtgaacaggg tacgcgggta    780

tttggctacg taacgacaat gggcgaatta cttaacgcct cgattatgtt ctttgcgcca    840

ctgatcatta atcgcatcgg tgggaaaaac gccctgctgc tggctggcac tattatgtct    900

gtacgtatta ttggctcatc gttcgccacc tcagcgctgg aagtggttat tctgaaaacg    960

ctgcatatgt ttgaagtacc gttcctgctg gtgggctgct ttaaatatat taccagccag   1020

tttgaagtgc gtttttcagc gacgatttat ctggtctgtt tctgcttctt taagcaactg   1080

gcgatgattt ttatgtctgt actggcgggc aatatgtatg aaagcatcgg tttccagggc   1140

gcttatctgg tgctgggtct ggtggcgctg ggcttcacct taatttccgt gttcacgctt   1200

agcggccccg gcccgctttc cctgctgcgt cgtcaggtga atgaagtcgc ttaa         1254
```

<210> SEQ ID NO 68
<211> LENGTH: 417
<212> TYPE: PRT
<213> ORGANISM: Escherichia coli

<400> SEQUENCE: 68

```
Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30
```

```
Trp Leu His Asp Ile Asn His Ile Ser Lys Ser Asp Thr Gly Ile Ile
        35                  40                  45

Phe Ala Ala Ile Ser Leu Phe Ser Leu Leu Phe Gln Pro Leu Phe Gly
    50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
                85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Phe Gly Arg Ala Arg
    130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Leu Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
        195                 200                 205

Ser Leu Lys Leu Ala Leu Glu Leu Phe Arg Gln Pro Lys Leu Trp Phe
    210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Ile Asn Arg Ile Gly Gly
        275                 280                 285

Lys Asn Ala Leu Leu Leu Ala Gly Thr Ile Met Ser Val Arg Ile Ile
    290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
            340                 345                 350

Cys Phe Cys Phe Phe Lys Gln Leu Ala Met Ile Phe Met Ser Val Leu
        355                 360                 365

Ala Gly Asn Met Tyr Glu Ser Ile Gly Phe Gln Gly Ala Tyr Leu Val
    370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala
```

<210> SEQ ID NO 69
<211> LENGTH: 1254
<212> TYPE: DNA

<213> ORGANISM: Escherichia coli

<400> SEQUENCE: 69

```
atgtactatt taaaaaacac aaacttttgg atgttcggtt tattcttttt cttttacttt     60
tttatcatgg gagcctactt cccgtttttc ccgatttggc tacatgacat caaccatatc    120
agcaaaagtg atacgggtat tatttttgct gctatttctc tgttctcgct attattccaa    180
ccgctgtttg gtctgctttc tgacaaactc gggctgcgca aatacctgct gtggattatt    240
accggcatgt tagtgatgtt tgcgccgttc tttattttta tcttcgggcc actgttacaa    300
tacaacattt tagtaggatc gattgttggt ggtatttatc ttggcttttg ttttaacgcc    360
ggtgcgcccg cagtagaggc atttatcgag aaagtcagcc gtcgcagtaa tttcgaattt    420
ggtcgcgcgc ggatgtttgg ctgtgttggc tgggcgctgt gtgcctcgat tgtcggcatc    480
atgttcacca tcaataatca gttcgttttc tggctgggtt ctggctgtgc actcatcctc    540
gccattttac tcttttcgc caaaacggat gcgccctctt ccgccacggt tgccaatgcg    600
gtaggtgcca accattcggc atttagcctt aaactggcgc tggaactgtt cagacagcca    660
aaactgtggt ttttgtcact gtatgttatt ggcgtttcct gcacctacga tgtttttgac    720
caacagtttg ctaatttctt tacttctttc tttgccaccg gtgaacaggg tacgcgggta    780
tttggctacg taacgacaat gggcgaatta cttaacgcct caattatgtt ctttgcgcca    840
ctgatcatta atcgcatcgg tgggaaaaat gccctgctgc tggctggcac tattatgtct    900
gtacgtatta ttggctcatc gttcgccacc tcagcgctgg aagtggttat tctgaaaacg    960
ctgcatatgt ttgaagtacc gttcctgctg gtgggctgct ttaaatatat taccagccag   1020
tttgaagtgc gtttttcagc gacgatttat ctggtctgtt tctgcttctt taagcaactg   1080
gcgatgattt ttatgtctgt actagcgggt aatatgtatg aaagcatcgg tttccagggc   1140
gcttatctgg tgctgggtct ggtggcgctg ggcttcacct taatttccgt gttcacgctt   1200
agcggccccg gcccgctttc tctactgcgt cgtcaggtga atgaagtcgc ttaa         1254
```

<210> SEQ ID NO 70
<211> LENGTH: 417
<212> TYPE: PRT
<213> ORGANISM: Escherichia coli

<400> SEQUENCE: 70

```
Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn His Ile Ser Lys Ser Asp Thr Gly Ile Ile
        35                  40                  45

Phe Ala Ala Ile Ser Leu Phe Ser Leu Leu Phe Gln Pro Leu Phe Gly
    50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
                85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Phe Gly Arg Ala Arg
```

130 135 140

Met Phe Gly Cys Val Gly Trp Ala Leu Cys Ala Ser Ile Val Gly Ile
145 150 155 160

Met Phe Thr Ile Asn Asn Gln Phe Val Phe Trp Leu Gly Ser Gly Cys
165 170 175

Ala Leu Ile Leu Ala Ile Leu Leu Phe Phe Ala Lys Thr Asp Ala Pro
180 185 190

Ser Ser Ala Thr Val Ala Asn Ala Val Gly Ala Asn His Ser Ala Phe
195 200 205

Ser Leu Lys Leu Ala Leu Glu Leu Phe Arg Gln Pro Lys Leu Trp Phe
210 215 220

Leu Ser Leu Tyr Val Ile Gly Val Ser Cys Thr Tyr Asp Val Phe Asp
225 230 235 240

Gln Gln Phe Ala Asn Phe Phe Thr Ser Phe Phe Ala Thr Gly Glu Gln
245 250 255

Gly Thr Arg Val Phe Gly Tyr Val Thr Thr Met Gly Glu Leu Leu Asn
260 265 270

Ala Ser Ile Met Phe Phe Ala Pro Leu Ile Ile Asn Arg Ile Gly Gly
275 280 285

Lys Asn Ala Leu Leu Leu Ala Gly Thr Ile Met Ser Val Arg Ile Ile
290 295 300

Gly Ser Ser Phe Ala Thr Ser Ala Leu Glu Val Val Ile Leu Lys Thr
305 310 315 320

Leu His Met Phe Glu Val Pro Phe Leu Leu Val Gly Cys Phe Lys Tyr
325 330 335

Ile Thr Ser Gln Phe Glu Val Arg Phe Ser Ala Thr Ile Tyr Leu Val
340 345 350

Cys Phe Cys Phe Phe Lys Gln Leu Ala Met Ile Phe Met Ser Val Leu
355 360 365

Ala Gly Asn Met Tyr Glu Ser Ile Gly Phe Gln Gly Ala Tyr Leu Val
370 375 380

Leu Gly Leu Val Ala Leu Gly Phe Thr Leu Ile Ser Val Phe Thr Leu
385 390 395 400

Ser Gly Pro Gly Pro Leu Ser Leu Leu Arg Arg Gln Val Asn Glu Val
405 410 415

Ala

<210> SEQ ID NO 71
<211> LENGTH: 122
<212> TYPE: DNA
<213> ORGANISM: Escherichia coli

<400> SEQUENCE: 71
gcgcaacgca attaatgtga gttagctcac tcattaggca ccccaggctt tacactttat 60
gcttccggct cgtatgttgt gtggaattgt gagcggataa caatttcaca caggaaacag 120
ct 122

<210> SEQ ID NO 72
<211> LENGTH: 122
<212> TYPE: DNA
<213> ORGANISM: Escherichia coli

<400> SEQUENCE: 72
gcgcaacgca attaatgtga gttagctcac tcattaggca ccccaggctt tacactttat 60

-continued

```
gcttccggct cgtatgttgt gtgaaattgt gagcggataa caatttcaca caggaaacag     120

ct                                                                    122
```